(12) United States Patent
Lerman et al.

(10) Patent No.: US 11,311,724 B2
(45) Date of Patent: Apr. 26, 2022

(54) TRANSCUTANEOUS AND TRANSCRANIAL NERVE STIMULATION

(71) Applicant: The Regents of the University of California, Oakland, CA (US)

(72) Inventors: Imanuel Lerman, La Jolla, CA (US); Ramesh Rao, La Jolla, CA (US); Donald Kimball, La Jolla, CA (US); Alan Simmons, La Jolla, CA (US); Dewleen Baker, La Jolla, CA (US); Mingxiong Huang, La Jolla, CA (US); Edward Zhong, La Jolla, CA (US); Bryan Davis, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 440 days.

(21) Appl. No.: 16/047,535

(22) Filed: Jul. 27, 2018

(65) Prior Publication Data

US 2019/0030334 A1 Jan. 31, 2019

Related U.S. Application Data

(60) Provisional application No. 62/538,444, filed on Jul. 28, 2017.

(51) Int. Cl.

| *A61B 5/00* | (2006.01) |
|---|---|
| *A61N 1/36* | (2006.01) |
| *A61B 5/0205* | (2006.01) |
| *A61B 5/16* | (2006.01) |
| *A61N 1/02* | (2006.01) |

(Continued)

(52) U.S. Cl.

CPC ...... *A61N 1/36025* (2013.01); *A61B 5/02055* (2013.01); *A61B 5/165* (2013.01); *A61B 5/4836* (2013.01); *A61B 5/4848* (2013.01); *A61B 5/7267* (2013.01); *A61N 1/025* (2013.01); *A61N 1/36031* (2017.08); *A61N 7/00* (2013.01); *A61B 5/01* (2013.01); *A61B 5/0261* (2013.01); *A61B 5/02405* (2013.01); *A61B 5/02438* (2013.01);

(Continued)

(58) Field of Classification Search
CPC .. A61B 5/00; A61B 5/02055; A61N 1/36025; A61N 1/36031
IPC .............................. A61B 5/00; A61N 1/36025
See application file for complete search history.

(56) References Cited

U.S. PATENT DOCUMENTS

| 2003/0135128 A1* | 7/2003 | Suffin | A61B 5/411 |
|---|---|---|---|
| | | | 600/544 |
| 2009/0234409 A1* | 9/2009 | Shuros | A61N 1/36514 |
| | | | 607/17 |

(Continued)

*Primary Examiner* — Joel F Brutus
(74) *Attorney, Agent, or Firm* — K&L Gates LLP; Louis C. Cullman; Georgia N. Kefallinos

(57) ABSTRACT

In an example, physiological signal(s) are received from physiological sensor(s) configured to measure at least one physiological property of a user. An arousal of at least one characteristic of at least one treatment resistant mood disorder is detected through employment of an estimation method based at least in part on at least one of the physiological signal(s). A value for at least one of a plurality of stimulation parameters is selected based at least in part on at least one of the physiological signal(s). An electric field based at least in part on the arousal is produced. The electric field is configured to stimulate at least a portion of a median nerve of the user transcutaneously. The electric field is based at least in part on at least some of the plurality of stimulation parameters.

17 Claims, 14 Drawing Sheets

(51) Int. Cl.
*A61N 7/00* (2006.01)
*A61B 5/024* (2006.01)
*A61B 5/0533* (2021.01)
*A61B 5/026* (2006.01)
*A61B 5/08* (2006.01)
*A61B 5/11* (2006.01)
*A61B 5/01* (2006.01)
*A61N 1/04* (2006.01)
*A61B 5/291* (2021.01)
*A61B 5/332* (2021.01)

(52) U.S. Cl.
CPC ........... *A61B 5/0533* (2013.01); *A61B 5/0809* (2013.01); *A61B 5/0816* (2013.01); *A61B 5/11* (2013.01); *A61B 5/291* (2021.01); *A61B 5/332* (2021.01); *A61B 5/4035* (2013.01); *A61B 2562/0209* (2013.01); *A61B 2562/0238* (2013.01); *A61B 2562/0276* (2013.01); *A61N 1/0456* (2013.01); *A61N 2007/0026* (2013.01); *A61N 2007/0078* (2013.01)

(56) References Cited

U.S. PATENT DOCUMENTS

| | | | | |
|---|---|---|---|---|
| 2010/0280336 | A1* | 11/2010 | Giftakis | A61B 5/4803 600/301 |
| 2011/0295335 | A1* | 12/2011 | Sharma | A61N 1/36139 607/40 |
| 2012/0116475 | A1* | 5/2012 | Nelson | A61N 1/0534 607/45 |

* cited by examiner

TRANSCUTANEOUS AND TRANSCRANIAL NERVE STIMULATION

PRIORITY

This application claims priority to and the benefit of U.S. Provisional Application Ser. No. 62/538,444, titled TRANSCUTANEOUS AND TRANSCRANIAL NERVE STIMULATION, filed Jul. 28, 2017, the entire contents of each of which are incorporated herein by reference and relied upon.

BACKGROUND

Both transcutaneous and transcranial nerve simulation may generally use electrical current produced by a device to stimulate the nerves for therapeutic purposes. Neurostimulation is the purposeful modulation of the nervous system's activity using invasive or non-invasive means. Transcranial nerve stimulation therapies can play a role in treating certain mood disorders.

Transcutaneous nerve stimulation therapy can play a role in treating acute and chronic pain, or certain mood disorders. Transcutaneous nerve stimulation therapy is typically applied through the skin using electrodes.

SUMMARY

The present disclosure provides new and innovative methods and systems for transcutaneous and transcranial nerve stimulation. An example method includes receiving a physiological signal, transmitted from a physiological sensor to measure a physiological property of a user. Then, detecting an arousal of a characteristic of a treatment resistant mood disorder by using an estimation method based on the physiological signal. A value is selected for a stimulation parameter based on the physiological signal, and an electric field is produced based on the arousal, the electric field stimulating least a portion of a nerve of the user transcutaneously based on the stimulation parameter.

An example system includes a storage device that stores stimulation parameters, and a physiological sensor that measures a physiological property of a user. The system further includes a receiving unit that receives a sensor signal communicated from the physiological sensor, and a stimulation device including an electric circuit that provides transcutaneous nerve stimulation. The system further includes a tangible non-transitory computer readable medium including instructions that cause a processing unit to receive a physiological signal from the receiving unit; detect an arousal of a characteristic of a treatment resistant mood disorder by using an estimation method based the physiological signal; select a value for the stimulation parameters, the value based on the physiological signal; and communicate stimulation instructions to the stimulation device, the stimulation instructions based on the arousal and the stimulation parameters.

Additional features and advantages of the disclosed methods and system are described in, and will be apparent from, the following Detailed Description and the Figures.

DETAILED DESCRIPTION OF EMBODIMENTS

Typically, many existing methods and systems for producing electrical fields, including ultrasonic pulses, for transcutaneous nerve stimulation may use physiological signals (e.g., heart rate variability) to trigger and/or adjust stimulation. However, typically, existing methods and systems may rely on physiological signals crossing a predetermined threshold to trigger stimulation. Unfortunately, some characteristics of moods may not be anticipated soon enough to enable stimulation prior to a user experiencing the characteristics. Furthermore, typical methods and systems for adaptively producing electrical fields may not adjust stimulation treatments quickly and/or effectively enough to impact the user prior to experiencing additional characteristics. Improved methods and systems for producing electrical fields for closed-loop transcutaneous nerve stimulation are an advantage of the present disclosure.

Typically, existing methods and systems for producing electrical fields, including transcutaneous ultrasonic nerve stimulation systems and transcranial neurostimulation systems, for transcutaneous nerve stimulation may require locating a target nerve manually since the location may vary for each user. Generally, existing methods and systems are not easily wearable by a user. Further, many existing methods may require too much power to be portable for long-term use. Improved methods and systems for producing electrical fields for transcutaneous nerve stimulation are an advantage of the present disclosure.

Closed-Loop Transcutaneous Median Nerve Stimulation

The exemplary embodiments disclosed in FIGS. 1 to 5 may disclose stimulating median nerve fibers transcutaneously.

Figure 1:
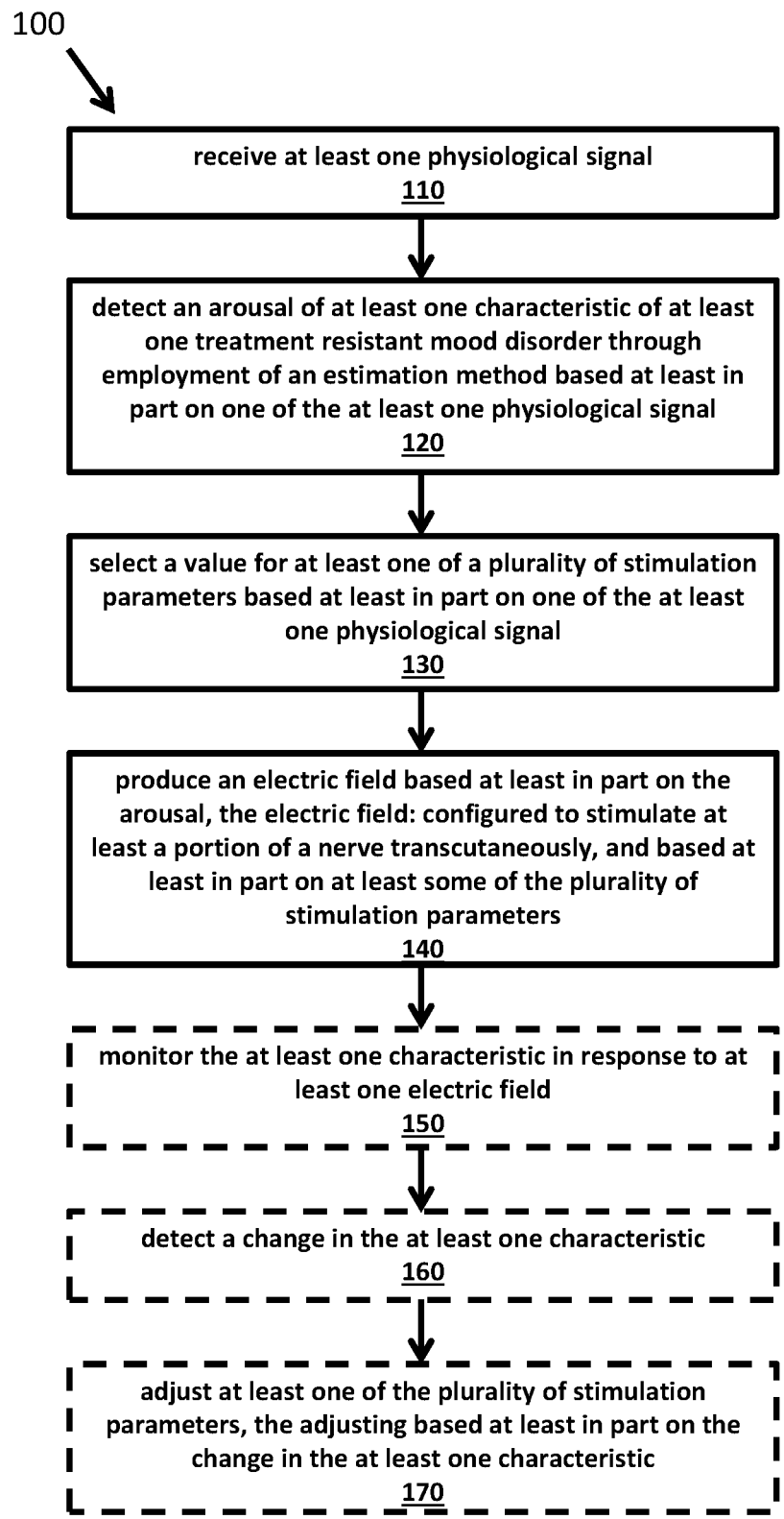
FIG. 1 is an example flow diagram of producing a closed-loop electric field for nerve stimulation according to an example of the present disclosure.

FIG. 1 is an example flow diagram 100 that may be used to produce a closed-loop electric field for transcutaneous median nerve stimulation according to an example of the present disclosure. Although the example flow diagram 100 is described with reference to the flowchart illustrated in FIG. 1, it will be appreciated that many other methods of performing the acts associated with the flow diagram may be used. For example, the order of some of the blocks may be changed, certain blocks may be combined with other blocks, and some of the blocks described are optional.

The flow diagram 100 begins by when at least one physiological signal may be received at block 110. Each of the at least one physiological signals may be transmitted from at least one physiological sensor. Each of the at least one physiological sensor may measure at least one physiological property of a user. By way of example and not limitation, the user may be a patient, a soldier, a consumer, an athlete, or any combinations thereof, and/or the like.

Next, an arousal of at least one characteristic of at least one treatment resistant mood disorder may be detected at block 120. The arousal may be detected through employment of an estimation method. The estimation method may be based at least in part on at least one of the at least one physiological signal. A value for at least one of a plurality of stimulation parameters may be selected at block 130. The value may be based at least in part on at least one of the at least one physiological signal. An electric field may be produced at block 140. The electric field may be based at least in part on the arousal and/or a change in the arousal. The electric field may stimulate at least a portion of a median nerve of the user transcutaneously. The electric field may be based at least in part on at least some of the plurality of stimulation parameters. The electric field may be based at least in part on the depth of at least a portion of a median nerve fiber under the skin of the user.

In an example of the present disclosure, the at least one characteristic may be monitored at block 150. The at least one characteristic may be monitored in response to at least one electric field. By way of example and not limitation, the at least one characteristic may be monitored throughout a day, throughout a night, for any number of days, combinations thereof, and/or the like. Block 150 may be an optional step in example method 100.

In an example of the present disclosure, a change in the at least one characteristic may be detected at block 160. Alternatively, a change in the arousal of the at least one characteristic may be detected. Block 160 may be an optional step in example method 100. At least one of the plurality of stimulation parameters may be adjusted at block 170. At least one of the plurality of stimulation parameters may be adjusted based at least in part on a change in the at least one characteristic. Stimulation parameters may be adjusted prior to the production of at least one additional electric field that stimulates at least a portion of a median nerve of the user transcutaneously. Block 170 may be an optional step in example method 100.

In an example of the present disclosure, the at least one characteristic may be confirmed by the user. Detecting an arousal of at least one characteristic of at least one treatment resistant mood disorder may be based at least in part on a first physiological signal and/or a plurality of physiological signals. Detecting an arousal may be verified by a second physiological signal and/or a plurality of additional physiological signals.

Figure 2:
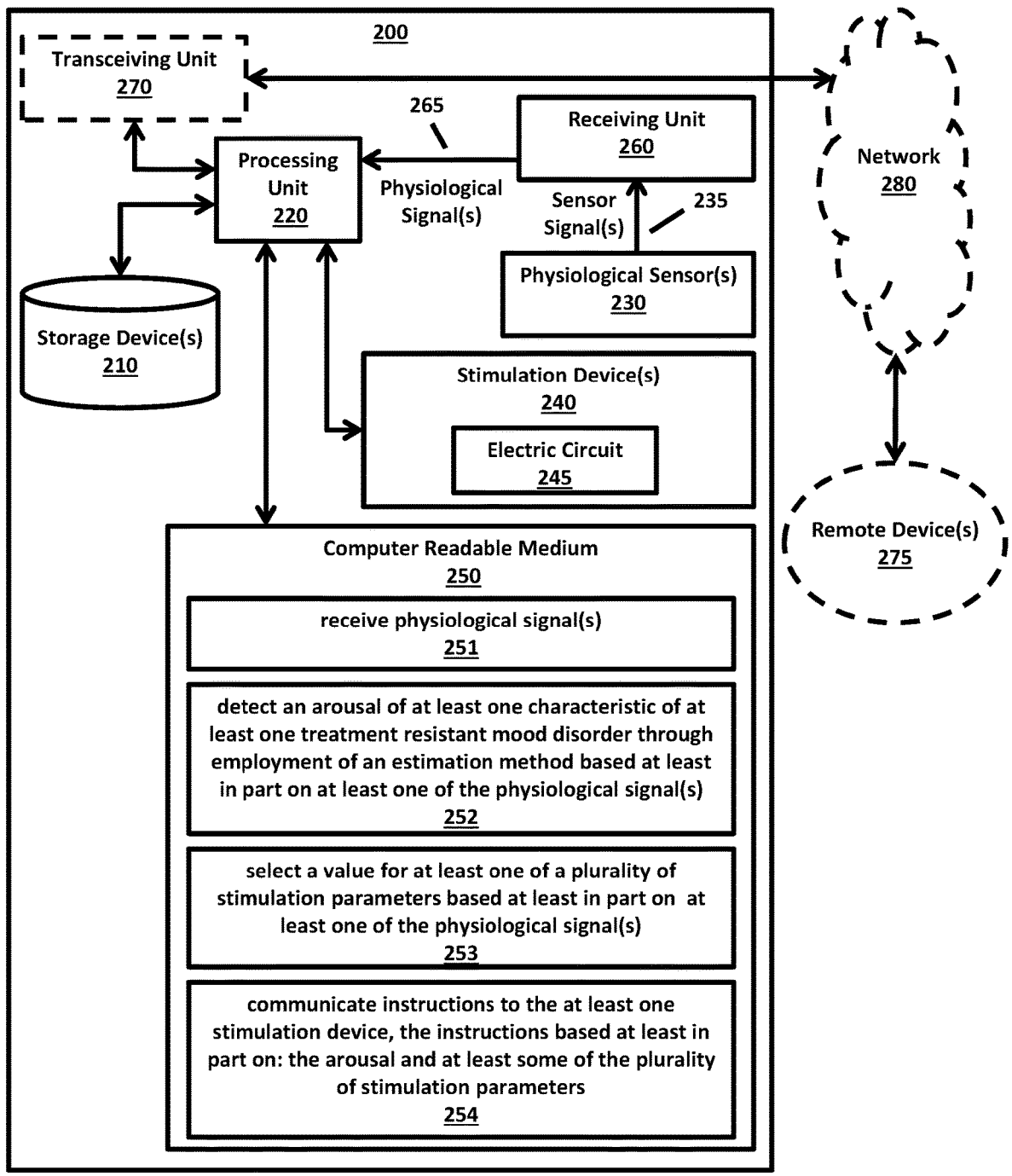
FIG. 2 is an example block diagram showing a system for electrical nerve stimulation according to an example of the present disclosure.

FIG. 2 is an example block diagram showing a system 200 for providing electrical nerve stimulation according to an example of the present disclosure. The system 200 may include at least one storage device 210. The at least one storage device 210 may store a plurality of stimulation parameters. The at least one storage device 210 may be a memory. As discussed herein, a memory device refers to a volatile or non-volatile memory device, such as RAM, ROM, EEPROM, or any other device capable of storing data.

The system 200 may include at least one physiological sensor 230. The at least one physiological sensor 230 may measure at least one physiological property of a user. The system 200 may include receiving unit 260. The receiving unit 260 may include at least one receiver. The receiving unit 260 may be receive at least one sensor signal 235. Each of the at least one sensor signal 235 may be communicated from one of the at least one physiological sensor 230. Alternatively, the receiving unit 260 may include at least one transceiver. The at least one transceiver may communicate with at least one of the at least one physiological sensor 230.

According to an example of the present disclosure, the system 200 may include at least one stimulation device 240. Each of the at least one stimulation device 240 may include an electric circuit 245. Each of the at least one stimulation device 240 may provide transcutaneous nerve stimulation. At least one of the at least one stimulation device 240 may stimulate a median nerve in the wrist of the user.

According to some of the various embodiments, the system 200 may include a processing unit 220 and a tangible non-transitory computer readable medium 250. The processing unit 220 may include at least one processor. As used herein, physical processor or processor refers to a device capable of executing instructions encoding arithmetic, logical, and/or I/O operations. In one illustrative example, a processor may follow Von Neumann architectural model and may include an arithmetic logic unit (ALU), a control unit, and a plurality of registers. In a further aspect, a processor may be a single core processor which is typically capable of executing one instruction at a time (or process a single pipeline of instructions), or a multi-core processor which may simultaneously execute multiple instructions. In another aspect, a processor may be implemented as a single integrated circuit, two or more integrated circuits, or may be a component of a multi-chip module (e.g., in which individual microprocessor dies are included in a single integrated circuit package and hence share a single socket). A processor may also be referred to as a central processing unit (CPU). In an example, the one or more physical processors may be in the system 200. In an example, all of the disclosed methods and procedures described herein can be implemented by the one or more processors. Further, the system 200 may be distributed over multiple processors, memories, and networks.

The computer readable medium 250 may include instructions that may cause the processing unit 220 to receive at least one physiological signal 265 at block 251. The at least one physiological signal 265 may be received from the receiving unit 260. The computer readable medium 250 may include instructions that may cause the processing unit 220 to detect an arousal of at least one characteristic of at least one treatment resistant mood disorder through employment of an estimation method at block 252. The estimation method may be based at least in part on at least one of the at least one physiological signal 265. The computer readable medium 250 may include instructions that may cause the processing unit 220 to select a value for at least one of the plurality of stimulation parameters at block 253. The value may be based at least in part on at least one of the at least one physiological signal 265. The computer readable medium 250 may include instructions that may cause the processing unit 220 to communicate stimulation instructions to at least one of the at least one stimulation device 240 at block 254. The stimulation instructions may be based at least in part on the arousal. The stimulation instructions may be based at least in part on at least some of the plurality of stimulation parameters.

According to some of the various embodiments, the system 200 may include a transceiving unit 270. The transceiving unit 270 may include at least one transceiver. The at least one transceiver may include at least one transmitter and at least one receiver. At least one of the at least one receiver may be the same as at least one of the at least one receiver associated with the receiving unit 260. Alternatively, at least one of the at least one transceiver may be the same as at least one of the at least one transceiver associated with the receiving unit 260. The transceiving unit 270 may communicate with at least one remote device 275 employing network 280. By way of example and not limitation, the remote device 275 may be employed by the user, a remote operator, a medical professional, combinations thereof, and/or the like. The system 200 may accept operational instructions from the remote device 275. The system 200 may communicate notifications to the remote device 275. In an alternate example, transceiving unit 270 may be directly communicatively connected to remote device 275.

According to some of the various embodiments, the at least one storage device 210 may be communicatively coupled to system 200 through employment of a wired and/or wireless network. The at least one storage device 210 may be managed through employment of a cloud service, a web-based electronic data capture system, a web application, a mobile device application, a mobile device operating system, a virtual machine, combinations thereof, and/or the like.

According to an example of the present disclosure, a sensor signal (e.g., 235) and a physiological signal (e.g., 265) may be the same. Alternatively, a physiological signal (e.g., 265) may be the baseband signal contained within a sensor signal (e.g., 235). The at least one physiological signal (e.g., 265) may include a heart rate signal, an electrocardiogram (ECG) signal, an electroencephalographic (EEG) signal, combinations thereof, and/or the like. The at least one physiological signal (e.g., 265) may include at least one data stream including measurements of heart beat, cortical potential, skin conductance response, laser Doppler shift, position, impedance pneumography potential, temperature, combinations thereof, and/or the like. By way of example and not limitation, position may include chest position, chest displacement, chest movement, combinations thereof, and/or the like.

According to an example of the present disclosure, the at least one physiological sensor (e.g., 230) may include a heart rate sensor, at least one scalp electrode, at least one skin conductance electrode, at least one photodetector, at least one avalanche photodiode, a respiration rate sensor, at least one thermistor, at least one thermometer, at least one thermocouple, combinations thereof, and/or the like. The heart rate sensor may measure heart rate electrically and/or optically. The heart rate sensor may measure Heart Rate Variability (HRV). Physiological sensors may measure HRV may be coupled to a chest strap and/or a wrist band. A chest strap and/or wrist band may be further coupled to at least one additional physiological sensor (e.g., 230) that may measure, for example, breathing rate, galvanic skin response, skin temperature, combinations thereof, and/or the like. The at least one photodetector may measure laser Doppler shift. Similarly, the at least one avalanche photodiode may measure laser Doppler shift. The at least one respiration rate sensor may include at least one impedance pneumography electrode, at least one capacitive sensor, at least one piezoelectric sensor, at least one servo, an acoustic transducer, an inclinometer, an accelerometer, combinations thereof, and/or the like. Alternatively, respiration rate may be estimated from HRV and/or a photoplethysmography (PPG). The physiological sensor (e.g., 230) may measure sympathetic tone. The sympathetic tone may be relative to previous measurements. The physiological sensor (e.g., 230) may measure parasympathetic tone. The parasympathetic tone may be relative to previous measurements. The physiological sensor (e.g., 230) may be wearable. The physiological sensor (e.g., 230) may transmit data in more than one time scale. Data transmitted from the physiological sensor (e.g., 230) may be recorded in a fixed time scale, in more than one time scale, in one adjustable time scale, in a plurality of adjustable time scales, combinations thereof, and/or the like. The physiological sensor (e.g., 230) may include a tattoo-based sensor or a skin-applied electrochemical sensor.

According to an example of the present disclosure, the at least one physiological property may be associated with the autonomic nervous system (ANS). The at least one physiological property may include heart rate, heart rate variability, brain activity, skin conductance, blood flow, respiration rate, core temperature, skin temperature, combinations thereof, and/or the like. Heart rate may, for example, be estimated or determined from an ECG signal and/or a PPG signal. HRV may, for example, be estimated or determined from an ECG signal. HRV may be estimated or determined through employment of at least one RR signal, at least one High Frequency (HF) signal, at least one Low Frequency (LF) signal, at least one LF/HF Ratio, combinations thereof, and/or the like. Brain activity may, for example, be estimated or determined from at least one EEG signal and/or at least one evoked potential. Skin conductance may, for example, be estimated or determined from a galvanic skin response. Blood flow may, for example, be estimated or determined from a laser Doppler velocimetry. Respiration rate may, for example, be estimated or determined from an impedance pneumograph.

In an example, the at least one characteristic may include stress, fear, pain, anxiety, depression, combinations thereof, and/or the like. An example of stress is a Post-Traumatic Stress Syndrome (PTSD) event experienced by the user. In an example, the at least one characteristic may be confirmed and/or associated with feedback from the user. A confirmation and/or feedback from the user may be associated with a distinct feature in at least one of the at least one physiological signal (e.g., 265). The confirmation and/or feedback may be associated with at least one result from the estimation method.

According to an example of the present disclosure, the estimation method may include at least one Orthogonal Matching Pursuit algorithm, at least one Basis Pursuit algorithm, at least one Bayesian statistical model, at least one Bayesian inference algorithm, at least one stochastic search algorithm, at least one hidden Markov model, at least one neural network, at least one kernel method algorithm, at least one particle filter, at least one deep learning algorithm, combinations thereof, and/or the like. The estimation method may be based at least in part on spectral analysis of at least one Fourier transform of at least one of the at least one physiological signal (e.g., 265). For example, HRV may be analyzed in the frequency domain. The frequencies of interest may be divided into three major bands: the very low frequency (VLF) may, for example, include a range of 0.003-0.04 Hz; the low frequency (LF) may, for example, include a range of 0.04-0.15 Hz; and the high frequency (HF) may, for example, include a range of 0.15-0.4 Hz. In an example, the estimation method may be based at least in part on at least one wavelet transform coefficient of at least one of the at least one physiological signal (e.g., 265). The at least one Fourier transform and the at least one wavelet transform coefficient may be based on the same physiological signal (e.g., 265).

According to an example of the present disclosure, the estimation method may include logistic regression. The estimation method may include binary prediction (e.g., Bayesian logistic regression) and/or at least one single index model. The estimation method may include full information for model-fitting. Model fitting may be employed to train prediction algorithms. Prediction algorithms may employ full information as a baseline or control for prediction and/or partial information. The partial information may be unobtrusive. The estimation method may include at least one inference engine. The estimation method may include at least one distribution estimator. The estimation method may include a state model including at least one unobservable process. The estimation method may include at least one filter that removes artifacts.

According to an example of the present disclosure, the estimation method may be based at least in part on at least one previous arousal, at least one previous physiological signal, at least one stimulation parameter, combinations thereof, and/or the like. The estimation method may be based at least in part on a history of arousal, a history of at least one physiological signal, a history of at least one stimulation parameter, combinations thereof, and/or the like. The estimation method may be based at least in part on at least one preference of the user. The preference may be based at least in part on characteristics that are physical, physiological, neurological, combinations thereof, and/or the like. The preference may be based at least in part on a history of arousal, a history of at least one physiological signal, a history of at least one stimulation parameter, combinations thereof, and/or the like. The estimation method may be based at least in part on a result of at least one previous estimation method.

In an example, the estimation method may be based at least in part on data from at least one training phase. The at least one training phase may include production of a plurality of distinct electric fields that stimulate at least a portion of a median nerve of the user transcutaneously. The at least one training phase may include monitoring the at least one characteristic. The data may include a history of arousal, a history of at least one physiological signal, a history of at least one stimulation parameter, combinations thereof, and/or the like. The data may include at least one feedback and/or at least one confirmation from the user.

According to some of the various embodiments, stimulation parameters may include a target location for stimulation on the body of the user, at least one stimulation pulse frequency, at least one stimulation pulse amplitude, a maximum open circuit voltage, at least one stimulation pulse width, a maximum allowable skin temperature, at least one stimulation pulse repetition rate for a number of stimulation pulses, at least one duty cycle of the stimulation pulses, a number of stimulation pulses in a group, a number of stimulation pulse groups each including consistent pulse repetition rates, a number of stimulation pulse groups wherein at least two of the stimulation pulse groups include distinct pulse repetition rates, stimulation pulse group ramp up time, duration of stimulation treatment, frequency of stimulation treatment, combinations thereof, and/or the like. Stimulation pulse frequency may include a carrier frequency. An example of a stimulation pulse frequency includes a sine wave including a frequency in the range of 1 kHz to 2 kHz with a 1 percent resolution. In an example, the carrier frequency may be varied. The carrier frequency may be varied to avoid electromagnetic interference. Stimulation pulse amplitude may, for example, include a range of 10 µA to 10 mA with a 10 percent resolution. The maximum open circuit voltage may, for example, include a range of 100 mV to 10 V with 10 percent resolution. According to some of the various embodiments, the maximum open circuit voltage may be designed for safety and performance during mechanical shock and vibration environments. Stimulation pulse width may be employed to limit current.

In an example, a plurality of stimulation pulses may be regulated. The plurality of stimulation pulses may be employed to determine a total stimulation level. Stimulation pulse width may include a resolution of 2 ms. The stimulation pulse repetition rate may be selectable and/or sweepable in, for example, 1 Hz steps. According to some of the various embodiments, the stimulation pulse repetition and/or the number of stimulation pulses may be based on the user's response to stimulation. In an example, the user's response may be determined through employment of at least one physiological signal (e.g., 265), at least one user feedback, at least one user confirmation, combinations thereof, and/or the like. The at least one duty cycle of stimulation pulses may be adjustable from 50 percent to 10 percent. The at least one duty cycle of stimulation pulses may be based on skin conductance. The number of stimulation pulses in a group may, for example, include a range of 2 to 2000. An example of at least two of the stimulation pulse groups including distinct pulse repetition rates is a 25 Hz group followed by a 10 Hz group. Stimulation pulse group ramp up time may, for example, include a range of 500 ms to 5 seconds. Duration of stimulation treatment may, for example, include a range of 1 to 10 minutes for at least one group of pulses.

In an example, the frequency of stimulation treatment may include seconds, minutes, hours, days, combinations thereof, and/or the like. The value for at least one of a plurality of stimulation parameters may be based at least in part on at least one physical attribute of the user. In the example, the at least one physical attribute may include gender, age, height, weight, wrist girth, at least one baseline autonomic tone, at least one baseline inflammation level, combinations thereof, and/or the like. The at least one baseline inflammation level may, for example, be based at least in part on a blood sample from a blood draw. In an alternate example, the at least one baseline inflammation level may, for example, be based at least in part on at least one measurement received from a wearable sensor such as a wristband, a tattoo-based sensor, a skin-applied electrochemical sensor, combinations thereof, and/or the like. At least one inflammation level may be employed to confirm reduction in stress, fear, pain, anxiety, depression, combinations thereof, and/or the like.

In an example, at least a portion of the system 200 may be a System on a Chip (SoC). The system 200 may further include signal conditioning circuitry. The system 200 may further include integrated power management circuitry.

Figure 3:
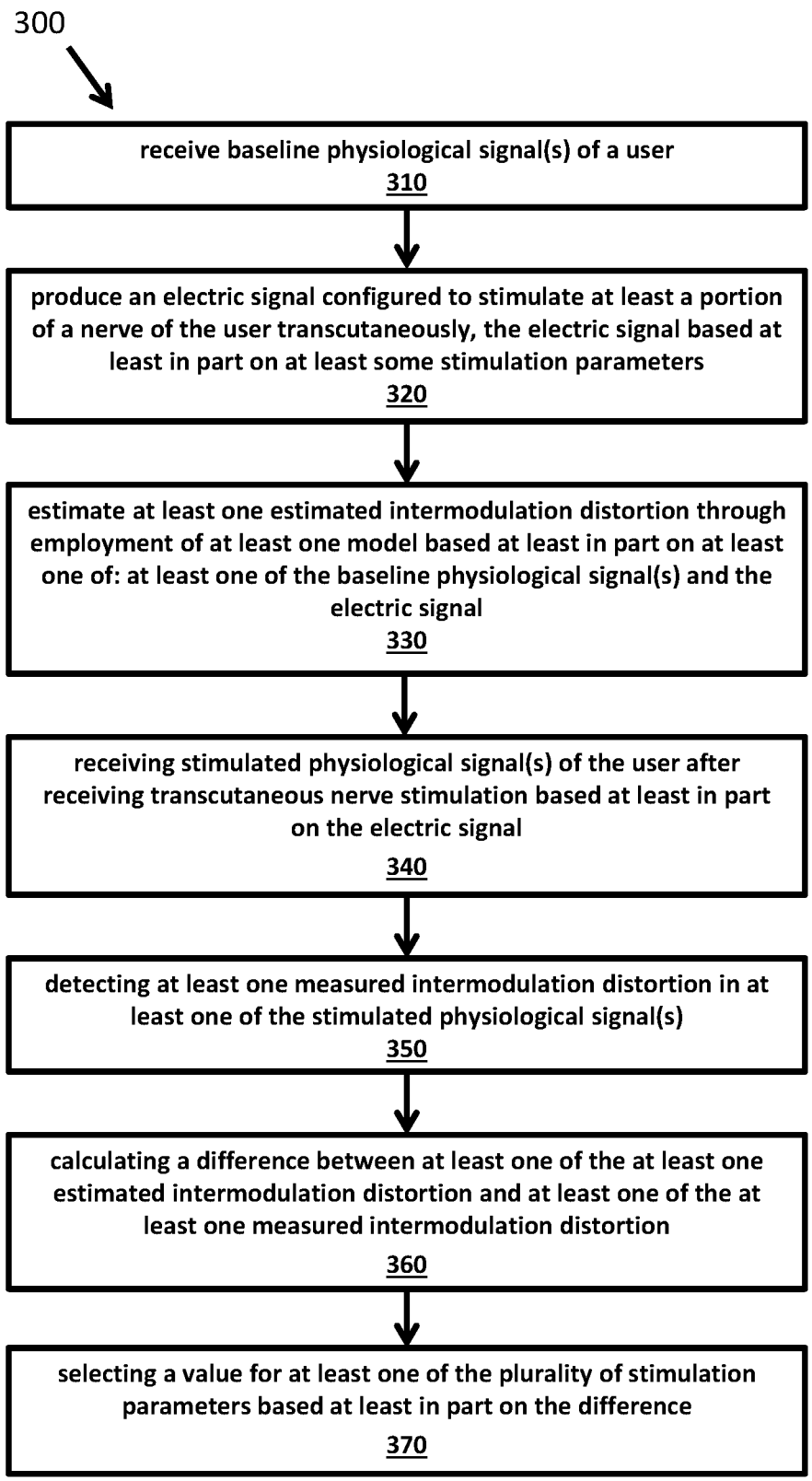
FIG. 3 is an example flow diagram of producing a closed-loop electric field for nerve stimulation according to an example of the present disclosure.

FIG. 3 is an example flow diagram 300 that may be used to produce a closed-loop electric field for transcutaneous median nerve stimulation according to an example of the present disclosure. Although the example flow diagram 300 is described with reference to the flowchart illustrated in FIG. 3, it will be appreciated that many other methods of performing the acts associated with the flow diagram may be used. For example, the order of some of the blocks may be changed, certain blocks may be combined with other blocks, and some of the blocks described are optional.

The flow diagram 300 begins when at least one baseline physiological signal may be received at block 310. Each of the at least one baseline physiological signal may be transmitted from at least one physiological sensor. Each of the at least one physiological sensor may measure at least one physiological property of a user. The baseline physiological signal may include a physiological signal captured prior to stimulation of at least a portion of a median nerve of the user. The physiological signal may be captured prior to recent stimulation or stimulation received within a predetermined historical timeframe.

Next, an electric signal to stimulate at least a portion of a median nerve of the user transcutaneously may be produced at block 320. The electric signal may be based at least in part on at least some of a plurality of stimulation parameters. By way of example and not limitation, the electric signal may include a pulse modulated signal.

Next, at least one estimated intermodulation distortion may be estimated through employment of at least one model for non-linear behavior at block 330. The at least one model may be based at least in part on the at least one baseline physiological signal, the electric signal, combination thereof, and/or the like. An example of a model for non-linear behavior is a Volterra series.

Next, at least one stimulated physiological signal may be received at block 340. Each of the at least one stimulated physiological signal may be transmitted from the physiological sensor to measure the at least one physiological property of the user. The at least one stimulated physiological signal may be received after the user receives transcutaneous nerve stimulation based at least in part on the electric signal. Each of the at least one baseline physiological signal may originate from the same sensor as one of the at least one stimulated physiological signal. The at least one stimulated physiological signal may be filtered. A filter may be based at least in part on at least one frequency component of the electric signal. For example, at least one filter may pass sidebands of the electric signal in the at least one stimulated physiological signal. By way of example and not limitation, nerve signals of the user may include a range of 4 Hz to 40 Hz. An electrical signal may, for example, include a pulse modulated signal of 1 kHz±100 Hz. In this example, at least one filter may pass 900 Hz to 1.1 kHz from at least one of the at least one stimulated physiological signal. According to some of the various embodiments, at least one of the at least one stimulated physiological signal may include artifacts. By way of example and not limitation, an artifact may include a frequency of 400 Hz to 4 kHz.

Next, at least one measured intermodulation distortion in at least one of the at least one stimulated physiological signal may be detected at block 350. At least one electronic filter may be employed to detect the at least one measured intermodulation distortion. The at least one electronic filter may be based at least in part on at least one of the at least one estimated intermodulation distortion. A difference between at least one of the at least one estimated intermodulation distortion and at least one of the at least one measured intermodulation distortion may be calculated at block 360. The difference may be calculated based at least in part on frequency offset (e.g., 10 Hz), modulation bandwidth (e.g., +/−2 Hz), carrier to side-band amplitude difference (e.g., −100 dB), amplitude modulation (e.g., +/−1 dB), carrier to side-band phase difference (e.g., +15 deg), phase modulation (e.g., +/−2 deg), combinations thereof, and/or the like. A value for at least one of the plurality of stimulation parameters may be selected at block 370. The value may be based at least in part on the difference. The value may be based at least in part on at least one of the at least one measured intermodulation distortion.

In the example, the at least one baseline physiological signal and the at least one stimulated physiological signal may each include a heart rate signal, an electrocardiogram signal, an electroencephalographic signal, combinations thereof, and/or the like. The at least one baseline physiological signal and the at least one stimulated physiological signal may each include at least one data stream including measurements of heart beat, cortical potential, skin conductance response, laser Doppler shift, position, impedance pneumography potential, temperature, combinations thereof, and/or the like.

In the example, the at least one of the at least one measured intermodulation distortion may be associated with characteristics of a treatment resistant mood disorder. The characteristics may include stress, fear, pain, anxiety, depression, combinations thereof, and/or the like.

In the example, at least a portion of the at least one electric signal may be removed from the at least one stimulated physiological signal through employment of a signal processing method, a signal analysis method, combinations thereof, and/or the like. By way of example and not limitation, the signal processing method may include at least one filter. The signal analysis method may, for example, include at least one frequency-domain analysis, at least one time-domain analysis, combinations thereof, and/or the like.

In the example, detecting at least one measured intermodulation distortion may include employment of an analog to digital converter (ADC). Detecting at least one measured intermodulation distortion may include employment of a low noise pre-amplifier (LNA). The ADC and the LNA may operate in at least one audio band. For example, the ADC may operate at a resolution of 24 bits at a sampling rate of 192 kSPS. In this example, the ADC may produce 144 dB in dynamic range and a flat frequency response from 20 Hz to 20 kHz. The LNA may, for example, produce a noise figure of 3 dB at normal skin temperatures. Output from the combination of the LNA to ADC may, for example, be employed as input into a Fast Fourier Transform (FFT) analyzer. The FFT analyzer may, for example, operate at a 1 Hz resolution from 20 Hz to 20 kHz. Employment of the LNA and ADC may be out-of-phase with employment of the electric signal. The LNA and ADC may be controlled through employment of at least one time gate.

According to some of the various embodiments, selecting the value for at least one of the plurality of stimulation parameters may be based on a goal of maximizing or minimizing a desired response in at least one of the at least one physiological property of the user. By way of example and not limitation, the desired response may include a reduction in sympathetic tone. In this example, at least one of the plurality of stimulation parameters may be adjusted based on a goal of minimizing sympathetic tone prior to an onset of an undesired response (e.g., muscle twitching). With a stimulation pulse frequency of 1 kHz, for example, the at least one estimated intermodulation distortion may be associated with a plurality of offsets ranging from 4 to 40 Hz, for example, from the stimulation pulse frequency. In this example, the value may be adjusted when at least one measured intermodulation distortion is detected 4 to 40 Hz offset from 1 kHz.

Figure 4:
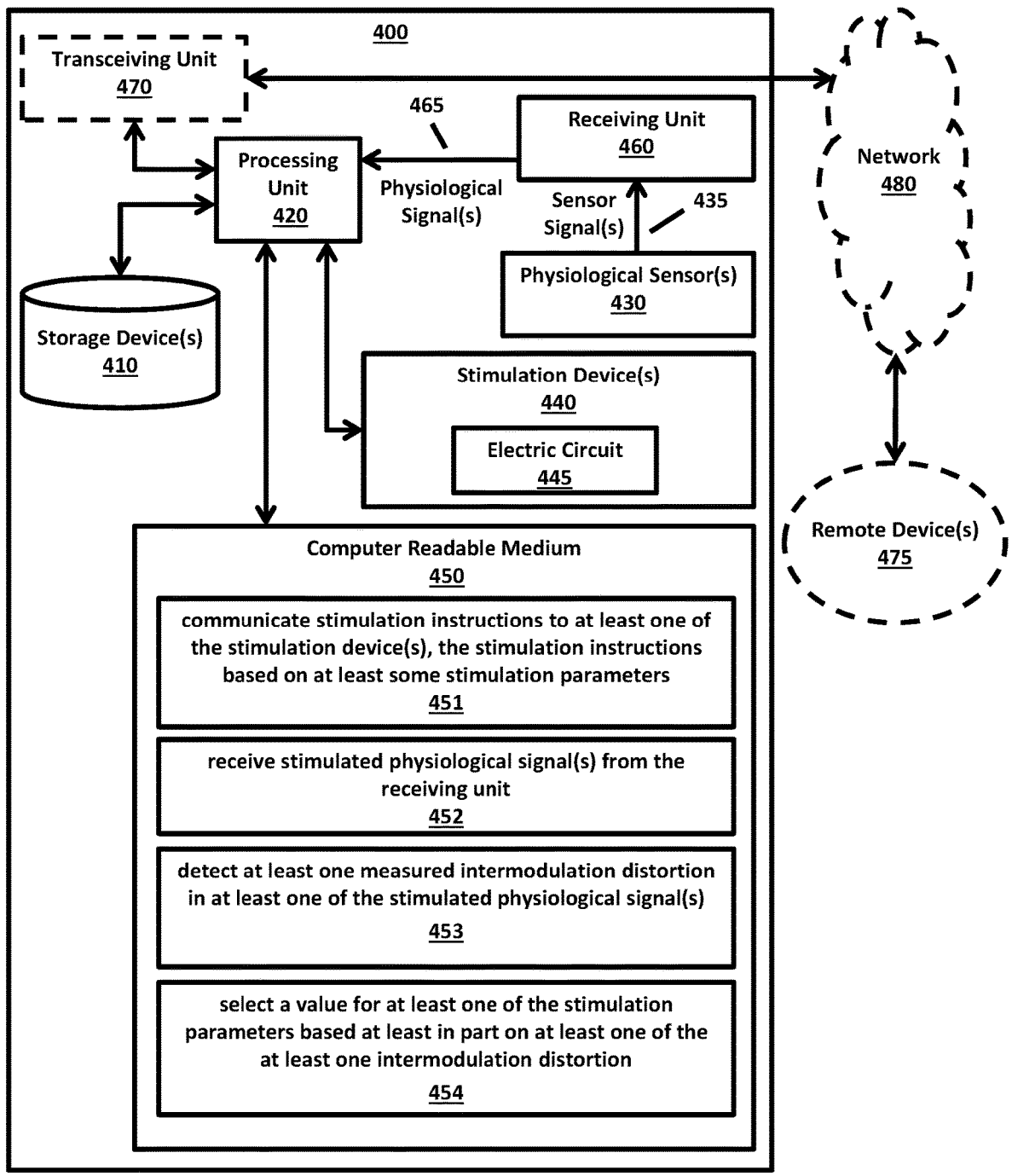
FIG. 4 is an example block diagram showing a system for providing electrical nerve stimulation according to an example of the present disclosure.

FIG. 4 is an example block diagram showing a system 400 for providing electrical nerve stimulation as per an example of the present disclosure. The system 400 may include at least one storage device 410. The at least one storage device 410 may store a plurality of stimulation parameters. The system 400 may include at least one physiological sensor 430. The at least one physiological sensor 430 may measure at least one physiological property of a user. The system 400 may include receiving unit 460. The receiving unit 460 may include at least one receiver. The receiving unit 460 may receive at least one stimulated sensor signal 435. Each of the at least one stimulated sensor signal 435 may be communicated from one of the at least one physiological sensor 430. Alternatively, the receiving unit 460 may include at least one transceiver. The at least one transceiver may communicate with the at least one physiological sensor 430.

In an example, the system 400 may include at least one stimulation device 440. Each of the at least one stimulation device 440 may include an electric circuit 445. Each of the at least one stimulation device 440 may provide transcutaneous nerve stimulation. At least one of the at least one stimulation device 440 may stimulate a median nerve in the wrist of the user.

In an example, the system 400 may include a processing unit 420 and a tangible non-transitory computer readable medium 450. The processing unit 420 may include at least one processor. The computer readable medium 450 may include instructions that cause the processing unit 420 to communicate stimulation instructions to at least one of the at least one stimulation device 440 at block 451. The stimulation instructions may be based at least in part on at least some of the plurality of stimulation parameters. The computer readable medium 450 may include instructions that cause the processing unit 420 to receive at least one stimulated physiological signal 465 from the receiving unit 460 at block 452. The computer readable medium 450 may include instructions that cause the processing unit 420 to detect at least one measured intermodulation distortion in at least one of the at least one stimulated physiological signal 465 at block 453. The computer readable medium 450 may include instructions that cause the processing unit 420 to select a value for at least one of the plurality of stimulation parameters based at least in part on at least one of the at least one measured intermodulation distortion at block 454.

In an example, the system 400 may include a transceiving unit 470. The transceiving unit 470 may include at least one transceiver. The at least one transceiver may include at least one transmitter and at least one receiver. At least one of the at least one receiver may be the same as at least one of the at least one receiver associated with the receiving unit 460. Alternatively, at least one of the at least one transceiver may be the same as at least one of the at least one transceiver associated with the receiving unit 460. The transceiving unit 470 may communicate with at least one remote device 475 employing network 480. By way of example and not limitation, the remote device 475 may be employed by the user, a remote operator, a medical professional, combinations thereof, and/or the like. The system 400 may accept operational instructions from the remote device 475. The system 400 may communicate notifications to the remote device 475. In an alternate example, transceiving unit 470 may be communicatively coupled directly to remote device 475.

In an example, the at least one storage device 410 may be communicatively coupled to system 400 through employment of a wired and/or wireless network. The at least one storage device 410 may be managed through employment of a cloud service, a web-based electronic data capture system, a web application, a mobile device application, a mobile device operating system, a virtual machine, combinations thereof, and/or the like.

Figure 5:
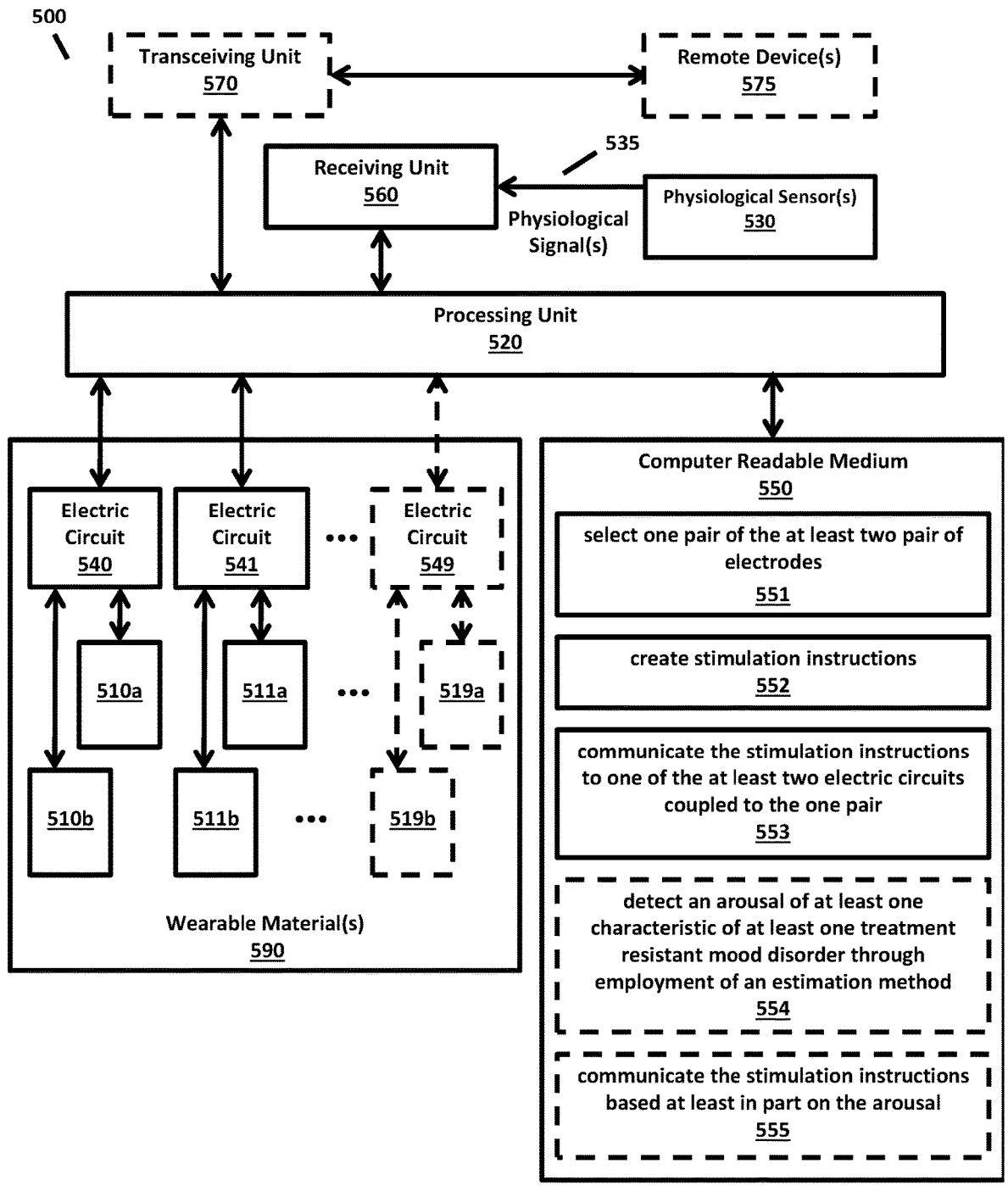
FIG. 5 is an example block diagram showing a system for selecting a pair of electrodes for electrical nerve stimulation according to an example of the present disclosure.

FIG. 5 is an example block diagram showing a system 500 for selecting a pair of electrodes for electrical nerve stimulation according to an example of the present disclosure. The system 500 may include at least one physiological sensor 530 and a receiving unit 560. The at least one physiological sensor 530 may communicate at least one physiological signal 535 to receiving unit 560. At least one of the at least one physiological signal 535 may be communicated directly from at least one of the at least one physiological sensor 530. Alternatively, at least one of the at least one physiological signal 535 may be embedded in a carrier signal communicated from the at least one physiological sensor 530. The receiving unit 560 may include a plurality of receivers, each for receiving at least one of the at least one physiological signal 535 from at least one of the at least one physiological sensor 530. The at least one physiological sensor 530 may measure at least one physiological property of a user. The system 500 may include at least two pair of electrodes (e.g., 510a and 510b, 511a and 511b . . . 519a and 519b) attached to at least one wearable material 590. The system 500 may include at least two electric circuits (e.g., 540, 541 . . . 549). Each of the at least two electric circuits (e.g., 540, 541 . . . 549) may be coupled to one pair of the at least two pair of electrodes (e.g., 510a and 510b, 511a and 511b . . . 519a and 519b). Each of the at least two electric circuits (e.g., 540, 541 . . . 549) may be for transcutaneous nerve stimulation. The system 500 may include a processing unit 520 and a tangible non-transitory computer readable medium 550.

In an example, the computer readable medium 550 may include instructions that cause processing unit 520 to select one pair (e.g., 510a and 510b) of the at least two pair of electrodes (e.g., 510a and 510b, 511a and 511b . . . 519a and 519b) based at least in part on at least one of the at least one physiological signal 535 at block 551. The at least one physiological signal 535 may include a response to at least one previous stimulation. The computer readable medium 550 may include instructions that cause processing unit 520 to create stimulation instructions at block 552. The stimulation instructions may be based at least in part on a plurality of stimulation parameters. The computer readable medium 550 may include instructions that cause processing unit 520 to communicate the stimulation instructions to one (e.g., 540) of the at least two electric circuits (e.g., 540, 541 . . . 549) coupled to the one pair (e.g., 510a and 510b) of the at least two pair of electrodes (e.g., 510a and 510b, 511a and 511b . . . 519a and 519b) at block 553. The computer readable medium 550 may include instructions that cause processing unit 520 to detect an arousal of at least one characteristic of at least one treatment resistant mood disorder through employment of an estimation method at block 554. The estimation method may be based at least in part on at least one of the at least one physiological signal 535. Alternatively, the instructions may cause processing unit 520 to detect a change in an arousal of at least one characteristic of at least one treatment resistant mood disorder. The computer readable medium 550 may include instructions that cause processing unit 520 to communicate the stimulation instructions based at least in part on the arousal at block 555. For example, stimulation may be started after detection of an arousal or an increase in an existing arousal. Similarly, stimulation may, for example, be altered or ceased after conclusion of an arousal or a decrease in an existing arousal. The system 500 may further include transceiving unit 570. The transceiving unit 570 may communicate with at least one remote device 575.

In an example, the at least one physiological signal (e.g., 535) may include a heart rate signal, an ECG signal, an EEG signal, an evoked potential, combinations thereof, and/or the like. The at least one physiological signal (e.g., 535) may include at least one data stream including measurements of heart beat, cortical potential, skin conductance response, laser Doppler shift, position, impedance pneumography potential, temperature, combinations thereof, and/or the like.

In an example, the at least two pair of electrodes (e.g., 510a and 510b, 511a and 511b . . . 519a and 519b) may include an array of pairs of electrodes. For example, an array of 64 electrodes includes 32 pair of electrodes. In the example, each pair of the at least two pair of electrodes (e.g., 510a and 510b, 511a and 511b . . . 519a and 519b) may be associated with one of a plurality of distinct locations on the body of the user. At least some of the plurality of distinct locations may change with adjustment, donning, or removal of the at least one wearable material (e.g., 590). At least one of the plurality of distinct locations may be in close proximity to at least a portion of at least one median nerve fiber of the user.

In an example, system 500 may further include a wristband, bracelet, watch band, combinations thereof, and/or the like including the at least one wearable material 590. The system 500 may, for example, be integrated into standard issue wrist-gear for a soldier, agent, officer, and/or the like.

Closed-Loop Transcutaneous Vagus Nerve Stimulation

The exemplary embodiments disclosed in FIGS. 1 to 5 may disclose stimulating vagus nerve fibers transcutaneously.

FIG. 1 is an example flow diagram 100 that may be used to produce a closed-loop electric field for transcutaneous vagus nerve stimulation according to an aspect of the present disclosure. Although the example flow diagram 100 is described with reference to the flowchart illustrated in FIG. 1, it will be appreciated that many other methods of performing the acts associated with the flow diagram may be used. For example, the order of some of the blocks may be changed, certain blocks may be combined with other blocks, and some of the blocks described are optional.

The flow diagram 100 begins when at least one physiological signal may be received at block 110. Each of the at least one physiological signal may be transmitted from at least one physiological sensor. Each of the at least one physiological sensor may measure at least one physiological property of a user. By way of example and not limitation, the user may be a patient, a soldier, a consumer, an athlete, combinations thereof, and/or the like.

In an example, an arousal of at least one characteristic of at least one treatment resistant mood disorder may be detected at block 120. The arousal may be detected through employment of an estimation method. The estimation method may be based at least in part on at least one of the at least one physiological signal. A value for at least one of a plurality of stimulation parameters may be selected at block 130. The value may be based at least in part on at least one of the at least one physiological signal. An electric field may be produced at block 140. The electric field may be based at least in part on the arousal and/or a change in the arousal. The electric field may stimulate at least a portion of a vagus nerve of the user transcutaneously. The electric field may be based at least in part on at least some of the plurality of stimulation parameters. The electric field may be based at least in part on the depth of at least a portion of a vagus nerve fiber under the skin of the user.

In an example, the at least one characteristic may be monitored at block 150. The at least one characteristic may be monitored in response to at least one electric field. By way of example and not limitation, the at least one characteristic may be monitored throughout a day, throughout a night, for a number of days, combinations thereof, and/or the like. In an example, a change in the at least one characteristic may be detected at block 160. Alternatively, a change in the arousal of the at least one characteristic may be detected. At least one of the plurality of stimulation parameters may be adjusted at block 170. At least one of the plurality of stimulation parameters may be adjusted based at least in part on a change in the at least one characteristic. Stimulation parameters may be adjusted prior to the production of at least one additional electric field stimulates at least a portion of a vagus nerve of the user transcutaneously.

In an example, the at least one characteristic may be confirmed by the user. Detecting an arousal of at least one characteristic of at least one treatment resistant mood disorder may be based at least in part on a first physiological signal and/or a plurality of physiological signals. Detecting an arousal may be verified by a second physiological signal and/or a plurality of additional physiological signals.

FIG. 2 is an example block diagram showing a system 200 for providing electrical nerve stimulation according to an example of the present disclosure. The system 200 may include at least one storage device 210. The at least one storage device 210 may store a plurality of stimulation parameters. The system 200 may include at least one physiological sensor 230. The at least one physiological sensor 230 may measure at least one physiological property of a user. The system 200 may include receiving unit 260. The receiving unit 260 may include at least one receiver. The receiving unit 260 may receive at least one sensor signal 235. Each of the at least one sensor signal 235 may be communicated from one of the at least one physiological sensor 230. Alternatively, the receiving unit 260 may include at least one transceiver. The at least one transceiver may communicate with the at least one physiological sensor 230.

In an example, the system 200 may include at least one stimulation device 240. Each of the at least one stimulation device 240 may include an electric circuit 245. Each of the at least one stimulation device 240 may provide transcutaneous nerve stimulation. At least one of the at least one stimulation device 240 may stimulate a vagus nerve in the neck of the user. In an alternate example, at least one of the at least one stimulation device 240 may stimulate a vagus nerve in the ear of the user.

In an example, the system 200 may include a processing unit 220 and a tangible non-transitory computer readable medium 250. The processing unit 220 may include at least one processor. The computer readable medium 250 may include instructions that cause the processing unit 220 to receive at least one physiological signal 265 at block 251. The at least one physiological signal 265 may be received from the receiving unit 260. The computer readable medium 250 may include instructions that cause the processing unit 220 to detect an arousal of at least one characteristic of at least one treatment resistant mood disorder through employment of an estimation method at block 252. The estimation method may be based at least in part on at least one of the at least one physiological signal 265. The computer readable medium 250 may include instructions that cause the processing unit 220 to select a value for at least one of the plurality of stimulation parameters at block 253. The value may be based at least in part on at least one of the at least one physiological signal 265. The computer readable medium 250 may include instructions that cause the processing unit 220 to communicate stimulation instructions to at least one of the at least one stimulation device 240 at block 254. The stimulation instructions may be based at least in part on the arousal. Additionally or alternatively, the stimulation instructions may be based at least in part on at least some of the plurality of stimulation parameters.

In an example, the system 200 may include a transceiving unit 270. The transceiving unit 270 may include at least one transceiver. The at least one transceiver may include at least one transmitter and at least one receiver. At least one of the at least one receiver may be the same as at least one of the at least one receiver associated with the receiving unit 260. Alternatively, at least one of the at least one transceiver may be the same as at least one of the at least one transceiver associated with the receiving unit 260. The transceiving unit 270 may communicate with at least one remote device 275 by employing network 280. By way of example and not limitation, the remote device 275 may be employed by the user, a remote operator, a medical professional, combinations thereof, and/or the like. The system 200 may accept operational instructions from the remote device 275. The system 200 may communicate notifications to the remote device 275. In an alternate example, the at least one remote device 275 may be communicatively coupled to transceiving unit 270 directly.

In an example, the at least one storage device 210 may be communicatively coupled to system 200 through employment of a wired and/or wireless network. The at least one storage device 210 may be managed through employment of a cloud service, a web-based electronic data capture system, a web application, a mobile device application, a mobile device operating system, a virtual machine, combinations thereof, and/or the like.

In an example, a sensor signal (e.g., 235) and a physiological signal (e.g., 265) may be the same. Alternatively, a physiological signal (e.g., 265) may be the baseband signal contained within a sensor signal (e.g., 235). The at least one physiological signal (e.g., 265) may include a heart rate signal, an electrocardiogram (ECG) signal, an electroencephalographic (EEG) signal, an evoked potential, combinations thereof, and/or the like. The at least one physiological signal (e.g., 265) may include at least one data stream including measurements of heart beat, cortical potential, skin conductance response, laser Doppler shift, position, impedance pneumography potential, temperature, combinations thereof, and/or the like. By way of example and not limitation, position may include chest position, chest displacement, chest movement, combinations thereof, and/or the like.

According to some of the various embodiments, the at least one physiological sensor (e.g., 230) may include a heart rate sensor, at least one scalp electrode, at least one skin conductance electrode, at least one photodetector, at least one avalanche photodiode, a respiration rate sensor, at least one thermistor, at least one thermometer, at least one thermocouple, combinations thereof, and/or the like. The heart rate sensor may measure heart rate electrically and/or optically. The heart rate sensor may measure Heart Rate Variability (HRV). Physiological sensors that measure HRV may be coupled to a chest strap and/or a wrist band. A chest strap and/or wrist band may be further coupled to at least one additional physiological sensor (e.g., 230) that measures, for example, breathing rate, galvanic skin response, skin temperature, combinations thereof, and/or the like. The at least one photodetector may measure laser Doppler shift. Similarly, the at least one avalanche photodiode may measure laser Doppler shift. The at least one respiration rate sensor may include at least one impedance pneumography electrode, at least one capacitive sensor, at least one piezoelectric sensor, at least one servo, an acoustic transducer, an inclinometer, an accelerometer, combinations thereof, and/or the like. Alternatively, respiration rate may be estimated from HRV and/or a photoplethysmography (PPG). The physiological sensor (e.g., 230) may measure sympathetic tone. The sympathetic tone may be relative to previous measurements. The physiological sensor (e.g., 230) may measure parasympathetic tone. The parasympathetic tone may be relative to previous measurements. The physiological sensor (e.g., 230) may be wearable. The physiological sensor (e.g., 230) may transmit data in more than one time scale. Data transmitted from the physiological sensor (e.g., 230) may be recorded in a fixed time scale, in more than one time scale, in one adjustable time scale, in a plurality of adjustable time scales, combinations thereof, and/or the like. At least two of a plurality of physiological sensors may transmit data in distinct time scales. Alternatively, at least two of a plurality of physiological sensors may transmit data in the same time scale. The physiological sensor (e.g., 230) may include a tattoo-based sensor or a skin-applied electrochemical sensor.

In an example, the at least one physiological property may be associated with the autonomic nervous system (ANS). The at least one physiological property may include heart rate, heart rate variability, brain activity, skin conductance, blood flow, respiration rate, core temperature, skin temperature, combinations thereof, and/or the like. Heart rate may, for example, be estimated or determined from an ECG signal and/or a PPG signal. HRV may, for example, be estimated or determined from an ECG signal. HRV may be estimated or determined through employment of at least one RR signal, at least one High Frequency (HF) signal, at least one Low Frequency (LF) signal, at least one LF/HF Ratio, combinations thereof, and/or the like. Brain activity may, for example, be estimated or determined from at least one EEG signal and/or at least one evoked potential. Skin conductance may, for example, be estimated or determined from a galvanic skin response. Blood flow may, for example, be estimated or determined from a laser Doppler velocimetry. Respiration rate may, for example, be estimated or determined from an impedance pneumograph.

In an example, the at least one characteristic may include stress, fear, pain, anxiety, depression, combinations thereof, and/or the like. An example of stress is a Post-Traumatic Stress Syndrome (PTSD) event experienced by the user. In the example, the at least one characteristic may be confirmed and/or associated with feedback from the user. A confirmation and/or feedback from the user may be associated with a distinct feature in at least one of the at least one physiological signal (e.g., 265). The confirmation and/or feedback may be associated with at least one result from the estimation method.

In an example, the estimation method may include at least one Orthogonal Matching Pursuit algorithm, at least one Basis Pursuit algorithm, at least one Bayesian statistical model, at least one Bayesian inference algorithm, at least one stochastic search algorithm, at least one hidden Markov model, at least one neural network, at least one kernel method algorithm, at least one particle filter, at least one deep learning algorithm, combinations thereof, and/or the like. The estimation method may be based at least in part on spectral analysis of at least one Fourier transform of at least one of the at least one physiological signal (e.g., 265). For example, HRV may be analyzed in the frequency domain. The frequencies of interest may be divided into three major bands: the very low frequency (VLE) may, for example, include a range of 0.003-0.04 Hz, the low frequency (LF) may, for example, include a range of 0.04-0.15 Hz, and the high frequency (HF) may, for example, include a range of 0.15-0.4 Hz. According to some of the various embodiments, the estimation method may be based at least in part on at least one wavelet transform coefficient of at least one of the at least one physiological signal (e.g., 265). The at least one Fourier transform and the at least one wavelet transform coefficient may be based on the same physiological signal (e.g., 265).

In an example, the estimation method may include logistic regression. The estimation method may include binary prediction (e.g., Bayesian logistic regression) and/or at least one single index model. The estimation method may include full information for model-fitting. Model fitting may be employed to train prediction algorithms. Prediction algorithms may employ full information as a baseline or control for prediction and/or partial information. The partial information may be unobtrusive. The estimation method may include at least one inference engine. The estimation method may include at least one distribution estimator. The estimation method may include a state model including at least one unobservable process. The estimation method may include at least one filter to remove artifacts from at least one of the at least one physiological signal (e.g., 265).

In an example, the estimation method may be based at least in part on at least one previous arousal, at least one previous physiological signal, at least one stimulation parameter, combinations thereof, and/or the like. The estimation method may be based at least in part on a history of arousal, a history of at least one physiological signal, a history of at least one stimulation parameter, combinations thereof, and/or the like. Additionally or alternatively, the estimation method may be based at least in part on at least one preference of the user. The preference may be based at least in part on characteristics that are physical, physiological, neurological, combinations thereof, and/or the like. Additionally or alternatively, the preference may be based at least in part on a history of arousal, a history of at least one physiological signal, a history of at least one stimulation parameter, combinations thereof, and/or the like. Additionally or alternatively, the estimation method may be based at least in part on a result of at least one previous estimation method.

In an example, the estimation method may be based at least in part on data from at least one training phase. The at least one training phase may include production of a plurality of distinct electric fields that stimulate at least a portion of a vagus nerve of the user transcutaneously. The at least one training phase may include monitoring the at least one characteristic. The data may include a history of arousal, a history of at least one physiological signal, a history of at least one stimulation parameter, combinations thereof, and/or the like. The data may include at least one feedback and/or at least one confirmation from the user.

In an example, stimulation parameters may include a target location for stimulation on the body of the user, at least one stimulation pulse frequency, at least one stimulation pulse amplitude, a maximum open circuit voltage, at least one stimulation pulse width, a maximum allowable skin temperature, at least one stimulation pulse repetition rate for a number of stimulation pulses, at least one duty cycle of the stimulation pulses, a number of stimulation pulses in a group, a number of stimulation pulse groups each including consistent pulse repetition rates, a number of stimulation pulse groups wherein at least two of the stimulation pulse groups include distinct pulse repetition rates, stimulation pulse group ramp up time, duration of stimulation treatment, frequency of stimulation treatment, combinations thereof, and/or the like. Stimulation pulse frequency may include a carrier frequency. An example of a stimulation pulse frequency includes a sine wave including a frequency in the range of 1 kHz to 2 kHz with a 1 percent resolution. In the example, the carrier frequency may be varied. The carrier frequency may be varied to avoid electromagnetic interference. Stimulation pulse amplitude may, for example, include a range of 10 µA to 10 mA with a 10 percent resolution. The maximum open circuit voltage may, for example, include a range of 100 mV to 10 V with 10 percent resolution. In the example, the maximum open circuit voltage may be for safety and performance during mechanical shock and vibration environments. Stimulation pulse width may be employed to limit current.

In an example, a plurality of stimulation pulses may be regulated. The plurality of stimulation pulses may be employed to determine a total stimulation level. Stimulation pulse width may include a resolution of 2 ms. The stimulation pulse repetition rate may be selectable and/or sweepable in, for example, 1 Hz steps. In the example, the stimulation pulse repetition and/or the number of stimulation pulses may be based on the user's response to stimulation. The user's response may be determined through employment of at least one physiological signal (e.g., 265), at least one user feedback, at least one user confirmation, combinations thereof, and/or the like. The at least one duty cycle of stimulation pulses may be adjustable from 50 percent to 10 percent. The at least one duty cycle of stimulation pulses may be based on skin conductance. The number of stimulation pulses in a group may, for example, include a range of 2 to 2000. An example of at least two of the stimulation pulse groups including distinct pulse repetition rates is a 25 Hz group followed by a 10 Hz group. Stimulation pulse group ramp up time may, for example, include a range of 500 ms to 5 seconds. Duration of stimulation treatment may, for example, include a range of 1 to 10 minutes for at least one group of pulses.

In an example, the frequency of stimulation treatment may include seconds, minutes, hours, any number of days, combinations thereof, and/or the like. The value for at least one of a plurality of stimulation parameters may be based at least in part on at least one physical attribute of the user. The at least one physical attribute may include gender, age, height, weight, neck girth, at least one baseline autonomic tone, at least one baseline inflammation level, combinations thereof, and/or the like. The at least one baseline inflammation level may, for example, be based at least in part on a blood sample from a blood draw. Alternatively, the at least one baseline inflammation level may, for example, be based at least in part on at least one measurement received from a wearable sensor such as a wristband, a tattoo-based sensor, a skin-applied electrochemical sensor, combinations thereof, and/or the like. At least one inflammation level may be employed to confirm reduction in stress, fear, pain, anxiety, depression, combinations thereof, and/or the like.

In an example, the system 200 may stimulate at least one A fiber of a vagus nerve. Vagus nerve A fibers may include myelinated, somatic, afferent, and efferent fibers. The system 200 may be further avoid stimulating B and C fibers of a vagus nerve. Vagus nerve B fibers may include moderately myelinated, efferent, and mainly preganglionic autonomic fibers. Vagus nerve C fibers may include un-myelinated afferent sensory and preganglionic efferent autonomic fibers.

In an example, at least one of the plurality of stimulation parameters may be based at least in part on an estimated diameter of one or more vagus nerve fibers. By way of example and not limitation, a minimum electric field for excitation of myelinated A fibers may include 6.2 V/m for a 20 μm diameter Aα fiber. In an alternate example, 12.3 V/m may be required for excitation of a 10 μm diameter Aβ fiber. In an alternate example, 24.6 V/m may be required for excitation of a 5 μm diameter Aδ fiber. In an alternate example, 49.2 V/m may be required for excitation of a 2.5 μm diameter B fiber. In an alternate example, 240 V/m may be required for excitation of very small C fibers including diameters of 0.1-1 μm. These examples may assume 1 ms stimulation pulse width.

In an example, at least a portion of the system 200 may be a System on a Chip (SoC). The system 200 may further include signal conditioning circuitry. The system 200 may further include integrated power management circuitry.

FIG. 3 is an example flow diagram 300 that may be used to produce a closed-loop electric field for transcutaneous vagus nerve stimulation according to an example of the present disclosure. Although the example flow diagram 300 is described with reference to the flowchart illustrated in FIG. 3, it will be appreciated that many other methods of performing the acts associated with the flow diagram may be used. For example, the order of some of the blocks may be changed, certain blocks may be combined with other blocks, and some of the blocks described are optional.

The flow diagram 300 begins when at least one baseline physiological signal may be received at block 310. Each of the at least one baseline physiological signal may be transmitted from at least one physiological sensor. Each of the at least one physiological sensor may measure at least one physiological property of a user. The baseline physiological signal may include a physiological signal captured prior to stimulation of at least a portion of a vagus nerve of the user. The physiological signal may be captured prior to recent stimulation or stimulation received within a predetermined historical timeframe.

Next, an electric signal that stimulates at least a portion of a vagus nerve of the user transcutaneously may be produced at block 320. The electric signal may be based at least in part on at least some of a plurality of stimulation parameters. By way of example and not limitation, the electric signal may include a pulse modulated signal.

Next, at least one estimated intermodulation distortion may be estimated through employment of at least one model for non-linear behavior at block 330. The at least one model may be based at least in part on the at least one baseline physiological signal, the electric signal, combination thereof, and/or the like. An example of a model for non-linear behavior is a Volterra series.

Next, at least one stimulated physiological signal may be received at block 340. Each of the at least one stimulated physiological signal may be transmitted from the physiological sensor to measure the at least one physiological property of the user. The at least one stimulated physiological signal may be received after the user receives transcutaneous nerve stimulation based at least in part on the electric signal. Each of the at least one baseline physiological signal may originate from the same sensor as one of the at least one stimulated physiological signal. The at least one stimulated physiological signal may be filtered. A filter may be based at least in part on at least one frequency component of the electric signal. For example, at least one filter may pass sidebands of the electric signal in the at least one stimulated physiological signal. By way of example and not limitation, nerve signals of the user may include a range of 4 Hz to 40 Hz. An electrical signal may, for example, include a pulse modulated signal of 1 kHz±100 Hz. In this example, at least one filter may pass 900 Hz to 1.1 kHz from at least one of the at least one stimulated physiological signal. In the example, at least one of the at least one stimulated physiological signal may include artifacts. By way of example and not limitation, an artifact may include a frequency of 400 Hz to 4 kHz.

Next, at least one measured intermodulation distortion in at least one of the at least one stimulated physiological signal may be detected at block 350. At least one electronic filter may be employed to detect the at least one measured intermodulation distortion. The at least one electronic filter may be based at least in part on at least one of the at least one estimated intermodulation distortion. A difference between at least one of the at least one estimated intermodulation distortion and at least one of the at least one measured intermodulation distortion may be calculated at block 360. The difference may be calculated based at least in part on frequency offset (e.g., 10 Hz), modulation bandwidth (e.g., +/−2 Hz), carrier to side-band amplitude difference (e.g., −100 dB), amplitude modulation (e.g., +/−1 dB), carrier to side-band phase difference (e.g., +15 deg), phase modulation (e.g., +/−2 deg), combinations thereof, and/or the like. A value for at least one of the plurality of stimulation parameters may be selected at block 370. The value may be based at least in part on the difference. The value may be based at least in part on at least one of the at least one measured intermodulation distortion.

In an example, the at least one baseline physiological signal and the at least one stimulated physiological signal may each include a heart rate signal, an electrocardiogram signal, an electroencephalographic signal, combinations thereof, and/or the like. The at least one baseline physiological signal and the at least one stimulated physiological signal may each include at least one data stream including measurements of heart beat, cortical potential, skin conductance response, laser Doppler shift, position, impedance pneumography potential, temperature, combinations thereof, and/or the like.

In an example, the at least one of the at least one measured intermodulation distortion may be associated with characteristics of a treatment resistant mood disorder. The characteristics may include stress, fear, pain, anxiety, depression, combinations thereof, and/or the like.

In an example, at least a portion of the at least one electric signal may be removed from the at least one stimulated physiological signal through employment of a signal processing method, a signal analysis method, combinations thereof, and/or the like. By way of example and not limitation, the signal processing method may include at least one filter. The signal analysis method may, for example, include at least one frequency-domain analysis, at least one time-domain analysis, combinations thereof, and/or the like.

In an example, detecting at least one measured intermodulation distortion may include employment of an analog to digital converter (ADC). Detecting at least one measured intermodulation distortion may include employment of a low noise pre-amplifier (LNA). The ADC and the LNA may operate in at least one audio band. For example, the ADC may be for a resolution of 24 bits at a sampling rate of 192 kSPS. In this example, the ADC may produce 144 dB in dynamic range and a flat frequency response from 20 Hz to 20 kHz. The LNA may, for example, produce a noise figure of 3 dB at normal skin temperatures. Output from the combination of the LNA to ADC may, for example, be employed as input into a Fast Fourier Transform (FFT) analyzer. The FFT analyzer may, for example, be for a 1 Hz resolution from 20 Hz to 20 kHz. Employment of the LNA and ADC may be out-of-phase with employment of the electric signal. The LNA and ADC may be controlled through employment of at least one time gate.

In an example, selecting the value for at least one of the plurality of stimulation parameters may be based on a goal of maximizing or minimizing a desired response in at least one of the at least one physiological property of the user. By way of example and not limitation, the desired response may include a reduction in sympathetic tone. In this example, at least one of the plurality of stimulation parameters may be adjusted based on a goal of minimizing sympathetic tone prior to an onset of an undesired response (e.g., muscle twitching). With a stimulation pulse frequency of 1 kHz, for example, the at least one estimated intermodulation distortion may be associated with a plurality of offsets ranging from 4 to 40 Hz, for example, from the stimulation pulse frequency. In this example, the value may be adjusted when at least one measured intermodulation distortion is detected 4 to 40 Hz offset from 1 kHz.

FIG. 4 is an example block diagram showing a system 400 for providing electrical nerve stimulation according to an example of the present disclosure. The system 400 may include at least one storage device 410. The at least one storage device 410 may store a plurality of stimulation parameters. The system 400 may include at least one physiological sensor 430. The at least one physiological sensor 430 may measure at least one physiological property of a user. The system 400 may include a receiving unit 460. The receiving unit 460 may include at least one receiver. The receiving unit 460 may receive at least one stimulated sensor signal 435. Each of the at least one stimulated sensor signal 435 may be communicated from one of the at least one physiological sensor 430. Alternatively, the receiving unit 460 may include at least one transceiver. The at least one transceiver may communicate with the at least one physiological sensor 430.

In an example, the system 400 may include at least one stimulation device 440. Each of the at least one stimulation device 440 may include an electric circuit 445. Each of the at least one stimulation device 440 may provide transcutaneous nerve stimulation. At least one of the at least one stimulation device 440 may stimulate a vagus nerve in the neck of the user. In an alternate example, a least one of the at least one stimulation device 440 may stimulate a vagus nerve in the ear of the user.

In an example, the system 400 may include a processing unit 420 and a tangible non-transitory computer readable medium 450. The processing unit 420 may include at least one processor. The computer readable medium 450 may include instructions that cause the processing unit 420 to communicate stimulation instructions to at least one of the at least one stimulation device 440 at block 451. The stimulation instructions may be based at least in part on at least some of the plurality of stimulation parameters. The computer readable medium 450 may include instructions that cause the processing unit 420 to receive at least one stimulated physiological signal 465 from the receiving unit 460 at block 452. The computer readable medium 450 may include instructions that cause the processing unit 420 to detect at least one measured intermodulation distortion in at least one of the at least one stimulated physiological signal 465 at block 453. The computer readable medium 450 may include instructions that cause the processing unit 420 to select a value for at least one of the plurality of stimulation parameters based at least in part on at least one of the at least one measured intermodulation distortion at block 454.

In an example, the system 400 may include a transceiving unit 470. The transceiving unit 470 may include at least one transceiver. The at least one transceiver may include at least one transmitter and at least one receiver. At least one of the at least one receiver may be the same as at least one of the at least one receiver associated with the receiving unit 460. Alternatively, at least one of the at least one transceiver may be the same as at least one of the at least one transceiver associated with the receiving unit 460. The transceiving unit 470 may communicate with at least one remote device 475 employing network 480. By way of example and not limitation, the remote device 475 may be employed by the user, a remote operator, a medical professional, combinations thereof, and/or the like. The system 400 may accept operational instructions from the remote device 475. The system 400 may communicate notifications to the remote device 475. In an alternate example, the remote device 475 and transceiving unit 470 may be directly communicatively coupled.

In an example, the at least one storage device 410 may be communicatively coupled to system 400 through employment of a wired and/or wireless network. The at least one storage device 410 may be managed through employment of a cloud service, a web-based electronic data capture system, a web application, a mobile device application, a mobile device operating system, a virtual machine, combinations thereof, and/or the like.

FIG. 5 is an example block diagram showing a system 500 for selecting a pair of electrodes for electrical nerve stimulation according to an embodiment of the present disclosure. The system 500 may include at least one physiological sensor 530 and a receiving unit 560. The at least one physiological sensor 530 may communicate at least one physiological signal 535 to receiving unit 560. At least one of the at least one physiological signal 535 may be communicated directly from at least one of the at least one physiological sensor 530. Alternatively, at least one of the at least one physiological signal 535 may be embedded in a carrier signal communicated from the at least one physiological sensor 530. The receiving unit 560 may include a plurality of receivers, each receiving at least one of the at least one physiological signal 535 from at least one of the at least one physiological sensor 530. The at least one physiological sensor 530 may measure at least one physiological property of a user. The system 500 may include at least two pair of electrodes (e.g., 510a and 510b, 511a and 511b . . . 519a and 519b) attached to at least one wearable material 590. The system 500 may include at least two electric circuits (e.g., 540, 541 . . . 549). Each of the at least two electric circuits (e.g., 540, 541 . . . 549) may be coupled to one pair of the at least two pair of electrodes (e.g., 510a and 510b, 511a and 511b . . . 519a and 519b). Each of the at least two electric circuits (e.g., 540, 541 . . . 549) may be for transcutaneous nerve stimulation. The system 500 may include a processing unit 520 and a tangible non-transitory computer readable medium 550.

In an example, the computer readable medium 550 may include instructions that cause processing unit 520 to select one pair (e.g., 510a and 510b) of the at least two pair of electrodes (e.g., 510a and 510b, 511a and 511b . . . 519a and 519b) based at least in part on at least one of the at least one physiological signal 535 at block 551. The at least one physiological signal 535 may include a response to at least one previous stimulation. The computer readable medium 550 may include instructions that cause processing unit 520 to create stimulation instructions at block 552. The stimulation instructions may be based at least in part on a plurality of stimulation parameters. The computer readable medium 550 may include instructions that cause processing unit 520 to communicate the stimulation instructions to one (e.g., 540) of the at least two electric circuits (e.g., 540, 541 . . . 549) coupled to the one pair (e.g., 510a and 510b) of the at least two pair of electrodes (e.g., 510a and 510b, 511a and 511b . . . 519a and 519b) at block 553. The computer readable medium 550 may include instructions that cause processing unit 520 to detect an arousal of at least one characteristic of at least one treatment resistant mood disorder through employment of an estimation method at block 554. The estimation method may be based at least in part on at least one of the at least one physiological signal 535. Alternatively, the instructions may cause processing unit 520 to detect a change in an arousal of at least one characteristic of at least one treatment resistant mood disorder. The computer readable medium 550 may include instructions that cause processing unit 520 to communicate the stimulation instructions based at least in part on the arousal at block 555. For example, stimulation may be started after detection of an arousal or an increase in an existing arousal. Similarly, stimulation may, for example, be altered or ceased after conclusion of an arousal or a decrease in an existing arousal. The system 500 may further include transceiving unit 570. The transceiving unit 570 may communicate directly or indirectly with at least one remote device 575.

In an example, the at least one physiological signal (e.g., 535) may include a heart rate signal, an ECG signal, an EEG signal, an evoked potential, combinations thereof, and/or the like. The at least one physiological signal (e.g., 535) may include at least one data stream including measurements of heart beat, cortical potential, skin conductance response, laser Doppler shift, position, impedance pneumography potential, temperature, combinations thereof, and/or the like.

In an example, the at least two pair of electrodes (e.g., 510a and 510b, 511a and 511b . . . 519a and 519b) may include an array of pairs of electrodes. For example, an array of 64 electrodes includes 32 pair of electrodes. In an example, each pair of the at least two pair of electrodes (e.g., 510a and 510b, 511a and 511b . . . 519a and 519b) may be associated with one of a plurality of distinct locations on the body of the user. At least some of the plurality of distinct locations may change with adjustment, donning, or removal of the at least one wearable material (e.g., 590). At least one of the plurality of distinct locations may be in close proximity to at least a portion of at least one vagus nerve fiber of the user.

In an example, system 500 may further include at least one biofuel cell. The at least one biofuel cell may power system 500. At least a portion of the system 500 may be a System on a Chip (SoC). The system 500 may include signal conditioning circuitry. The system 500 may include integrated power management circuitry.

In an example, system 500 may further include a scarf, collar, tie, combinations thereof, and/or the like including the at least one wearable material 590. The system 500 may, for example, be integrated into standard issue neck-gear for a soldier, agent, officer, and/or the like.

Figure 6:
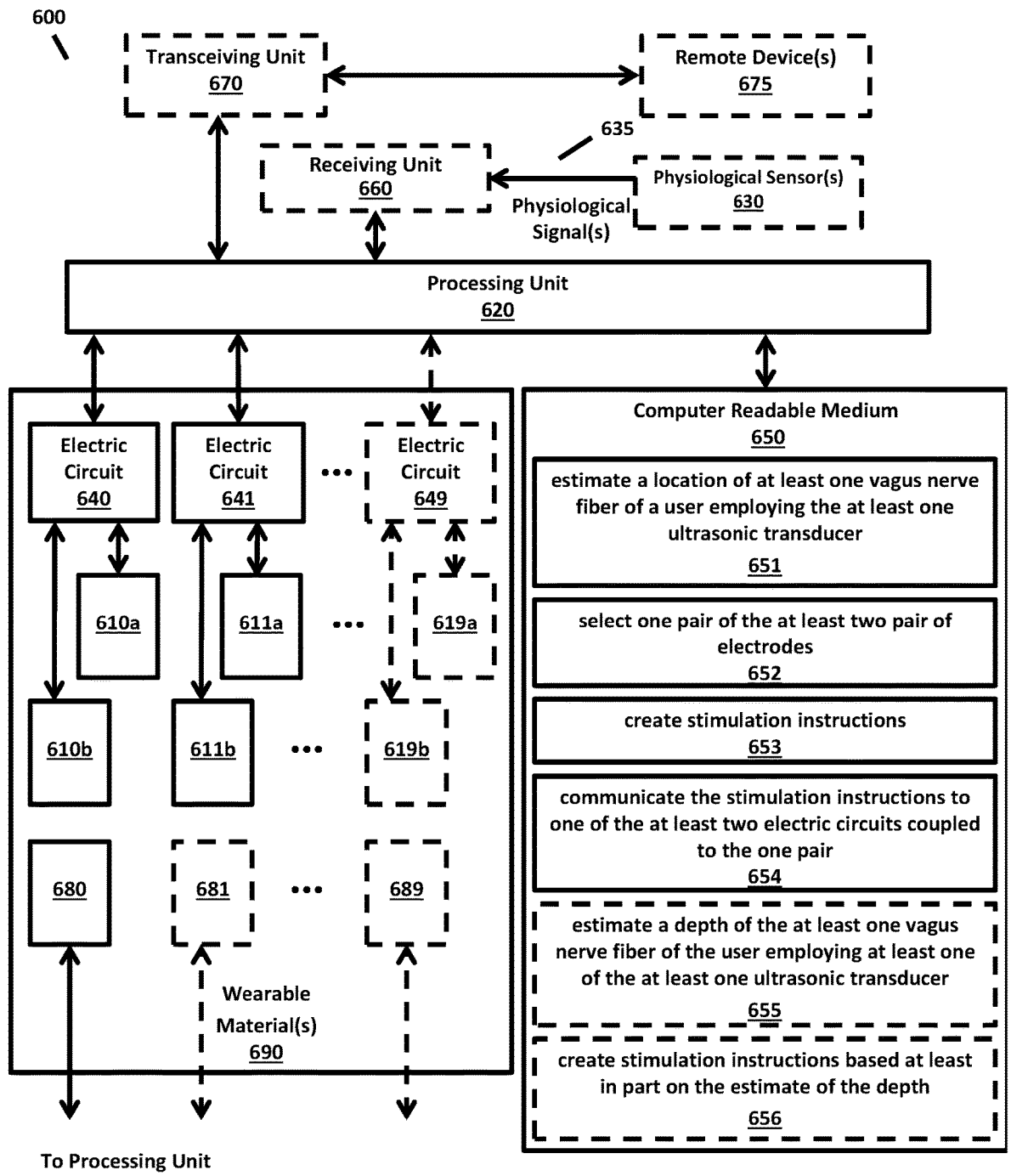
FIG. 6 is an example block diagram showing a system employing at least one ultrasonic transducer for selecting a pair of electrodes for electrical nerve stimulation according to an example of the present disclosure.

FIG. 6 is an example block diagram showing a system 600 employing at least one ultrasonic transducer (e.g., 680, 681 . . . 689) for selecting a pair of electrodes (e.g., 610a and 610b) for electrical nerve stimulation according to an example of the present disclosure. The system 600 may include at least one physiological sensor 630 and a receiving unit 660. The at least one physiological sensor 630 may communicate at least one physiological signal 635 to receiving unit 660. Receiving unit 660 may include a plurality of receivers, each receiving at least one of the at least one physiological signal 635 from at least one of the at least one physiological sensor 630. The at least one physiological sensor 630 may measure at least one physiological property of a user. The system 600 may include at least two pair of electrodes (e.g., 610a and 610b, 611a and 611b . . . 619a and 619b) attached to at least one wearable material 690. The system 600 may include at least two electric circuits (e.g., 640, 641 . . . 649). Each (e.g., 640) of the at least two electric circuits (e.g., 640, 641 . . . 649) may be coupled to one pair (e.g., 610a and 610b) of the at least two pair of electrodes (e.g., 610a and 610b, 611a and 611b . . . 619a and 619b). Each of the at least two electric circuits (e.g., 640, 641 . . . 649) may be for transcutaneous nerve stimulation.

According to some of the various embodiments, the system 600 may include at least one ultrasonic transducer (e.g., 680, 681 . . . 689). The at least one ultrasonic transducer (e.g., 680, 681 . . . 689) may be attached to the at least one wearable material 690. The at least one ultrasonic transducer may, for example, operate under 100 μW. The system 600 may include a processing unit 620 and a tangible non-transitory computer readable medium 650. The computer readable medium 650 may include instructions that cause processing unit 620 to estimate a location of at least a portion of at least one vagus nerve fiber of a user employing the at least one ultrasonic transducer (e.g., 680, 681 . . . 689) at block 651. For example, the system 600 may estimate a location of at least one A fiber of a vagus nerve. Vagus nerve group A fibers consist of myelinated, somatic, afferent, and efferent fibers. The system 600 may further avoid stimulating B and C fibers of a vagus nerve. Vagus nerve group B fibers are moderately myelinated, efferent, and mainly preganglionic autonomic fibers, and C fibers are un-myelinated afferent sensory and preganglionic efferent autonomic fibers. In an example, the computer readable medium 650 may include instructions that cause processing unit 620 to select one pair (e.g., 610a and 610b) of the at least two pair of electrodes (e.g., 610a and 610b, 611a and 611b . . . 619a and 619b) based at least in part on the estimate of the location at block 652.

In an example, the computer readable medium 650 may include instructions that cause processing unit 620 to create stimulation instructions at block 653. The stimulation instructions may be based at least in part on a plurality of stimulation parameters. The computer readable medium 650 may include instructions that cause processing unit 620 to communicate the stimulation instructions to one (e.g., 640) of the at least two electric circuits (e.g., 640, 641 . . . 649) coupled to the one pair (e.g., 610a and 610b) of the at least two pair of electrodes (e.g., 610a and 610b, 611a and 611b . . . 619a and 619b) at block 654. Each of the at least two electric circuits (e.g., 640, 641 . . . 649) may produce an electric field. The electric field may stimulate at least a portion of the at least one vagus nerve fiber of the user transcutaneously. The computer readable medium 650 may include instructions that cause processing unit 620 to estimate a depth of at least a portion of the at least one vagus nerve fiber of the user employing at least one of the at least one ultrasonic transducer (e.g., 680, 681 . . . 689) at block 655. The system 600 may detect vagal nerve fibers within the carotid sheath. The computer readable medium 650 may include instructions that cause processing unit 620 to create stimulation instructions based at least in part on the estimate of the depth at block 656. A value for at least one of the plurality of stimulation parameters may be based at least in part on the estimate of the depth.

In an example, the at least one ultrasonic transducer (e.g., 680, 681 . . . 689) may be flexible. The at least one ultrasonic transducer (e.g., 680, 681 . . . 689) may include at least one array of ultrasonic transducers.

In an example, system 600 may include at least one biofuel cell. The at least one biofuel cell may power system 600. At least a portion of the system 600 may be a System on a Chip (SoC). The system 600 may further include signal conditioning circuitry. The system 600 may further include integrated power management circuitry. The system 600 may further include transceiving unit 670. The transceiving unit 670 may communicate directly or indirectly with at least one remote device 675.

In an example, system 600 may include a scarf, collar, tie, combinations thereof, and/or the like including the at least one wearable material 690. The system 600 may, for example, be integrated into standard issue neck-gear for a soldier, agent, officer, and/or the like.

Figure 7:
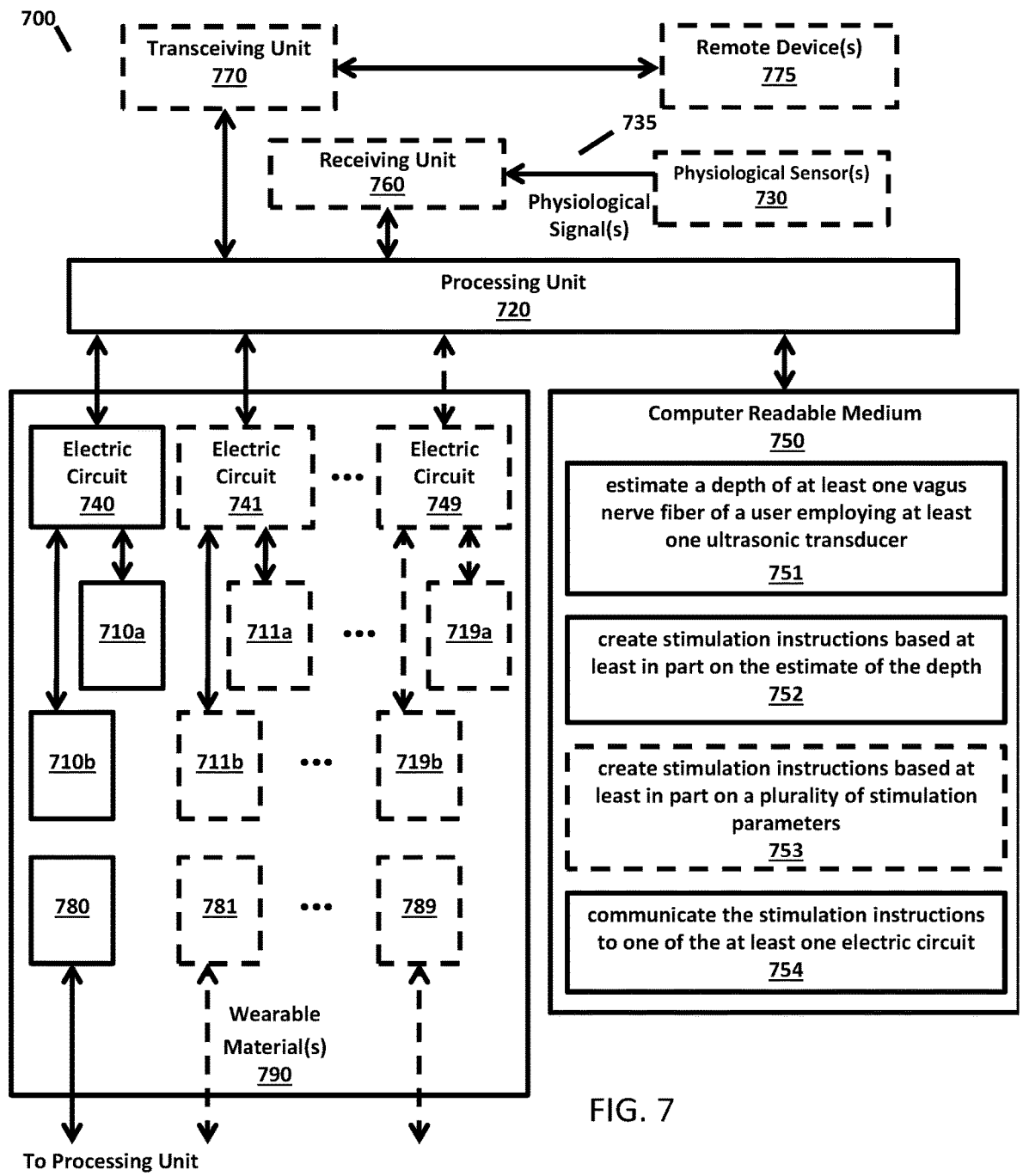
FIG. 7 is an example block diagram showing a system for electrical nerve stimulation based on estimated depth of at least one vagus nerve fiber according to an example of the present disclosure.

FIG. 7 is an example block diagram showing a system 700 for electrical nerve stimulation based on estimated depth of at least a portion of at least one vagus nerve fiber according to an example of the present disclosure. The system 700 may include at least one physiological sensor 730 and a receiving unit 760. The at least one physiological sensor 730 may communicate at least one physiological signal 735 to receiving unit 760. Receiving unit 760 may include a plurality of receivers, each receiving at least one of the at least one physiological signal 735 from at least one of the at least one physiological sensor 730. The at least one physiological sensor 730 may measure at least one physiological property of a user. The system 700 may include at least one pair of electrodes (e.g., 710a and 710b, 711a and 711b . . . 719a and 719b) attached to at least one wearable material 790. The system 700 may include at least one electric circuit (e.g., 740, 741 . . . 749). Each (e.g., 740) of the at least one electric circuit (e.g., 740, 741 . . . 749) may be coupled to one pair (e.g., 710a and 710b) of the at least one pair of electrodes (e.g., 710a and 710b, 711a and 711b . . . 719a and 719b). Each of the at least one electric circuit (e.g., 740, 741 . . . 749) may be for transcutaneous nerve stimulation. The system 700 may include at least one ultrasonic transducer (e.g., 780, 781 . . . 789). The at least one ultrasonic transducer (e.g., 780, 781 . . . 789) may be attached to the at least one wearable material 790. The system 700 may include a processing unit 720 and a tangible non-transitory computer readable medium 750. The computer readable medium 750 may include instructions that cause processing unit 720 to estimate a depth of at least a portion of at least one vagus nerve fiber of a user employing the at least one ultrasonic transducer (e.g., 780, 781 . . . 789) at block 751. The computer readable medium 750 may include instructions that cause processing unit 720 to create stimulation instructions based at least in part on the estimate of the depth at block 752. The computer readable medium 750 may include instructions that cause processing unit 720 to create stimulation instructions based at least in part on a plurality of stimulation parameters at block 753. A value for at least one of the plurality of stimulation parameters may be based at least in part on the estimate of the depth. The computer readable medium 750 may include instructions that cause processing unit 720 to communicate the stimulation instructions to one (e.g., 740) of the at least one electric circuit (e.g., 740, 741 . . . 749) at block 754. Each of the at least one electric circuit (e.g., 740, 741 . . . 749) may produce an electric field. The electric field may stimulate at least a portion of the at least one vagus nerve fiber of the user transcutaneously.

In an example, the at least one ultrasonic transducer (e.g., 780, 781 . . . 789) may be flexible. The at least one ultrasonic transducer (e.g., 780, 781 . . . 789) may include at least one array of ultrasonic transducers.

In an example, the system 700 may further include at least one biofuel cell. The at least one biofuel cell may power the system 700. At least a portion of the system 700 may be a System on a Chip (SoC). The system 700 may further include signal conditioning circuitry. The system 700 may further include integrated power management circuitry. The system 700 may further include a transceiving unit 770. The transceiving unit 770 may communicate directly or indirectly with at least one remote device 775.

In an example, the system 700 may further include a scarf, collar, tie, combinations thereof, and/or the like including the at least one wearable material 790. The system 700 may, for example, be integrated into standard issue neck-gear for a soldier, agent, officer, and/or the like.

Ultrasound Stimulation

Examples of the present disclosure provide transcutaneous nerve stimulation through employment of at least one ultrasonic transducer, or transcranial neurostimulation through employment of at least one ultrasonic transducer.

Figure 8:
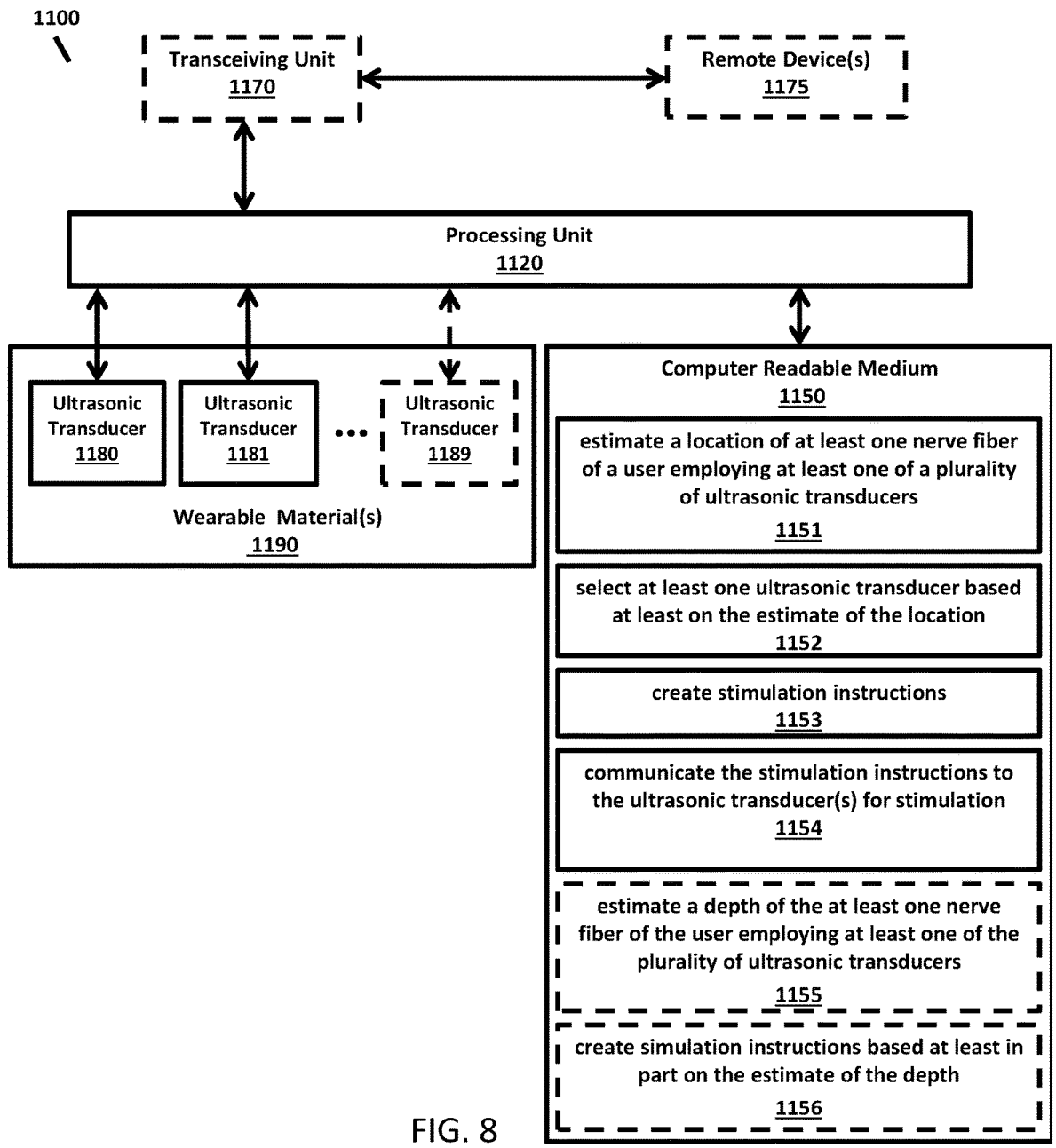
FIG. 8 is an example block diagram showing a system for selecting an ultrasonic transducer for ultrasonic nerve stimulation according to an example of the present disclosure.

FIG. 8 is an example block diagram showing a system 1100 for selecting an ultrasonic transducer for ultrasonic nerve stimulation as per an aspect of various embodiments. The system 1100 may include a plurality of ultrasonic transducers (e.g., 1180, 1181 . . . 1189). The plurality of ultrasonic transducers (e.g., 1180, 1181 . . . 1189) may be attached to the at least one wearable material 1190. The plurality of ultrasonic transducers (e.g., 1180, 1181 . . . 1189) may be for dry stimulation.

In an example, the system 1100 may include a processing unit 1120 and a tangible non-transitory computer readable medium 1150. The processing unit 1120 may include at least one processor. The computer readable medium 1150 may include instructions that cause the processing unit 1120 to estimate a location of at least one nerve fiber of a user employing at least one of the plurality of ultrasonic transducers (e.g., 1180, 1181 . . . 1189) at block 1151. The at least one nerve fiber may include at least one vagus nerve fiber, at least one median nerve fiber, at least one splanchnic and or nerve fiber, at least one splenic nerve fiber, combinations thereof, and/or the like. By way of example and not limitation, the user may be a patient, a soldier, a consumer, an athlete, combinations thereof, and/or the like. The computer readable medium 1150 may include instructions that cause the processing unit 1120 to select at least one ultrasonic transducer for stimulation from the at least one of the plurality of ultrasonic transducers based at least in part on the estimate of the location at block 1152. The computer readable medium 1150 may include instructions that cause the processing unit 1120 to create stimulation instructions at block 1153. The stimulation instructions may be based at least in part on a plurality of stimulation parameters. The computer readable medium 1150 may include instructions that cause the processing unit 1120 to communicate the stimulation instructions to the at least one ultrasonic transducer for stimulation at block 1154. The computer readable medium 1150 may include instructions that cause the processing unit 1120 to estimate a depth of the at least one nerve fiber of the user employing at least one of the plurality of ultrasonic transducers at block 1155. The computer readable medium 1150 may include instructions that cause the processing unit 1120 to create simulation instructions based at least in part on the estimate of the depth of the at least one nerve fiber at 1156.

In an example, the system 1100 may include a transceiving unit 1170. The transceiving unit 1170 may include at least one transceiver. The at least one transceiver may include at least one transmitter and at least one receiver. The transceiving unit 1170 may communicate directly or indirectly with at least one remote device 1175. By way of example and not limitation, the remote device 1175 may be employed by the user, a remote operator, a medical professional, combinations thereof, and/or the like. The system 1100 may accept operational instructions from the remote device 1175. The system 1100 may communicate notifications to the remote device 1175.

In an example, the plurality of ultrasonic transducers (e.g., 1180, 1181 . . . 1189) may be flexible. The plurality of ultrasonic transducers (e.g., 1180, 1181 . . . 1189) may be at least a part of at least one array of transducers. The plurality of ultrasonic transducers (e.g., 1180, 1181 . . . 1189) may produce a Focused Ultrasound (FUS) beam. Each of the plurality of ultrasonic transducers (e.g., 1180, 1181 . . . 1189) may be spherically curved. For example, at least one of the plurality of ultrasonic transducers (e.g., 1180, 1181 . . . 1189) may include up to 10 cm diameter and up to a 8 cm radius of curve. The transducers may include randomly placed elements up to a number of 256 to improve the focus density without allowing for a target focal spot or grating lobes. Using the random array transducer may allow for electronic steering of the focus spot in the r direction up to a range of 1 cm. This rapid cycling of a steered focus spot in the r direction may potentially decrease additive heat and mechanical damage effects to the target nerve. In an example, relative phases of waveforms produced by at least some of the plurality of ultrasonic transducers (e.g., 1180, 1181 . . . 1189) may be adjusted. By way of example and not limitation, at least one of the plurality of ultrasonic transducers (e.g., 1180, 1181 . . . 1189) may individually and/or collectively produce an acoustic focus of 1-5 mm$^2$. The plurality of ultrasonic transducers (e.g., 1180, 1181 . . . 1189) may, for example, deliver a range of up to 6-10 MPa pressure to a target nerve. The plurality of ultrasonic transducers (e.g., 1180, 1181 . . . 1189) may be calibrated, for example, for a pressure of 1-20 Mega Pascal (MPa) in a shallow water tank. The Peak positive and negative pressure may be equivalent to continuous sine wave power density. In an example, the system 1100 may produce a plurality of ultrasonic pulses. The plurality of ultrasonic pulses may stimulate at least one nerve fiber. The plurality of ultrasonic pulses may avoid stimulation of at least one off-target nerve fiber.

In an example, the plurality of stimulation parameters may include a target location for stimulation on the body of the user, ultrasonic pulse center frequency, ultrasonic pulse amplitude, ultrasonic pulse intensity, ultrasonic pulse duration, local ultrasonic pulse repetition frequency, global ultrasonic pulse repetition frequency, duty cycle of the ultrasonic pulses, ultrasonic spatial pulse length, a number of ultrasonic pulses in a group, a number of ultrasonic pulse groups each with consistent pulse repetition rates, a number of ultrasonic pulse groups at least two of the ultrasonic pulse groups including distinct pulse repetition rates, ultrasonic pulse ramp up time, ultrasonic pulse damping, relative phase of at least one ultrasonic pulse, relative amplitude of at least one ultrasonic pulse, duration of ultrasonic treatment, frequency of ultrasonic treatment, deactivation pulse center frequency, deactivation pulse amplitude, deactivation pulse intensity, deactivation pulse duration, deactivation pulse repetition frequency, duration of deactivation treatment, combinations thereof, and/or the like.

According to some of the various embodiments, the ultrasonic pulse center frequency may, for example, include 2-3.5 MHz for focused ultrasound. The ultrasonic pulse intensity may be determined at a spatial maximum or over a spatial average. The ultrasonic pulse intensity may be calculated as a temporal peak, temporal average, pulse average, and/or the like. The local ultrasonic pulse repetition frequency may, for example, include a frequency in the range of 1 Khz to 5 Khz. A signal modulated by the local ultrasonic pulse repetition frequency may be modulated by the global ultrasonic pulse repetition frequency. The global ultrasonic pulse repetition frequency may, for example, include a frequency in the range of 1 Hz to 50 Hz. The duty cycle of the ultrasonic pulses may, for example, be adjustable from 10% to 90%. The stimulation duration, for example, can range from 0.8 ms to 10 ms. The pulse repetition frequency may be altered during the stimulation duration with either increase or decrease in frequency, for example from 1-50 Hz resulting in a chirp type of signal. The center frequency may be altered during the stimulation duration with either increase or decrease in frequency, for example from 1-4 MHz resulting in a chirp type of signal. The duty cycle of the ultrasonic pulses may be applied to the local ultrasonic pulse repetition frequency and/or the global ultrasonic pulse repetition frequency.

In an example, system 1100 may further include at least one biofuel cell. The at least one biofuel cell may power system 1100. At least a portion of the system 1100 may be a System on a Chip (SoC). The system 1100 may include signal conditioning circuitry. The system 1100 may include integrated power management circuitry.

In an example, system 1100 may further include a scarf, collar, tie, wristband, article of clothing, wrap, adhesive patch, combinations thereof, and/or the like including the at least one wearable material 1190. The system 1100 may, for example, be integrated into standard issue neck-gear for a soldier, agent, officer, and/or the like.

Figure 9:
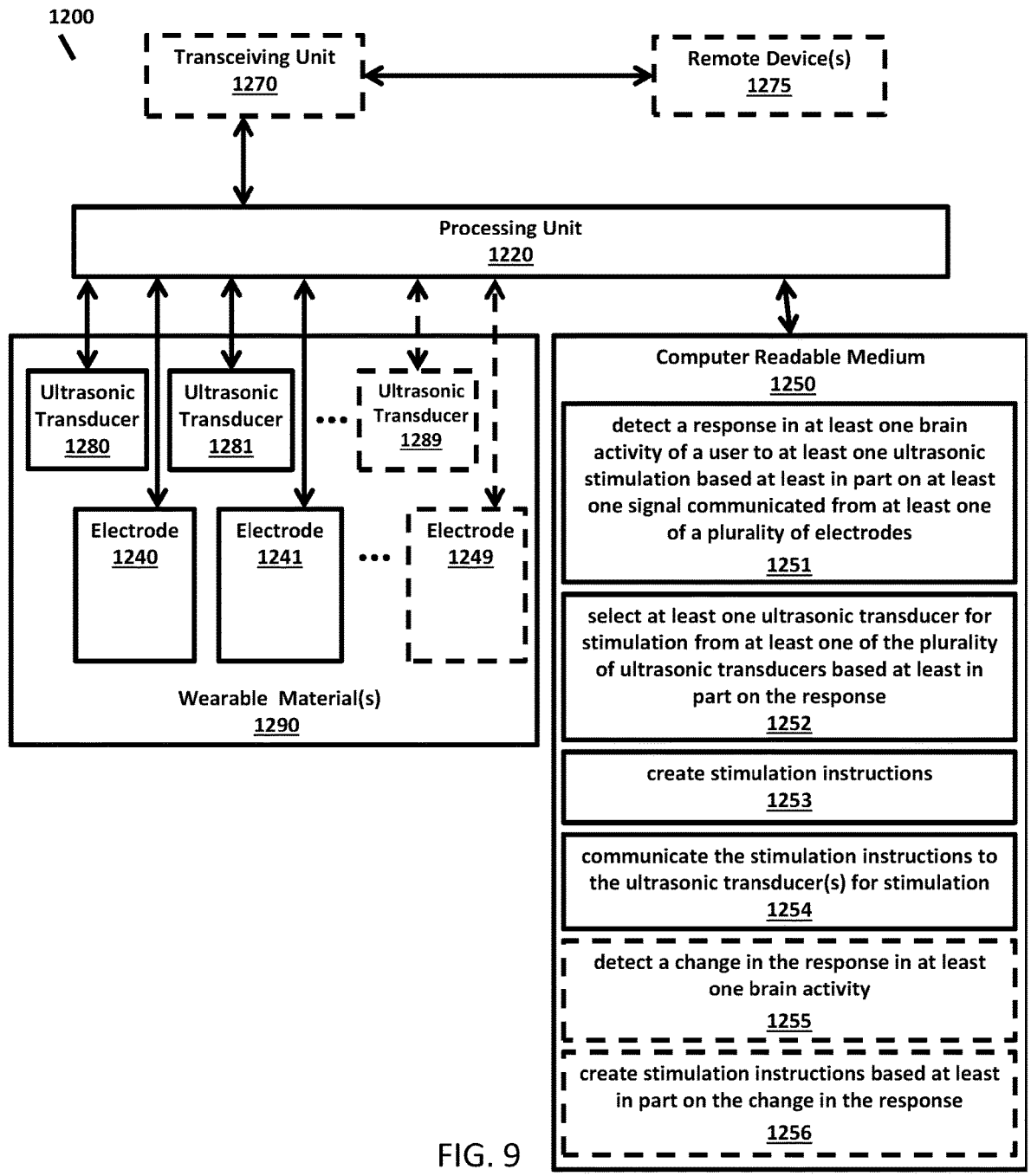
FIG. 9 is an example block diagram showing a system for selecting an ultrasonic transducer for ultrasonic transcranial neurostimulation according to an example of the present disclosure.

FIG. 9 is an example block diagram showing a system 1200 for selecting an ultrasonic transducer for ultrasonic transcranial neurostimulation according to an example of the present disclosure. The system 1200 may include a plurality of electrodes (e.g., 1240, 1241 . . . 1249). The plurality of electrodes (e.g., 1240, 1241 . . . 1249) may be attached to at least one wearable material 1290. The plurality of electrodes (e.g., 1240, 1241 . . . 1249) may be for dry sensing. The plurality of electrodes (e.g., 1240, 1241 . . . 1249) may be for electroencephalography (EEG) recording and/or evoked potential. Each of the plurality of electrodes (e.g., 1240, 1241 . . . 1249) may include a pair of electrodes. Alternatively, each of the plurality of electrodes (e.g., 1240, 1241 . . . 1249) may be coupled to at least one common reference electrode.

In an example, the system 200 may include a plurality of ultrasonic transducers (e.g., 1280, 1281 . . . 1289). The plurality of ultrasonic transducers (e.g., 1280, 1281 . . . 1289) may be attached to the at least one wearable material 1290. The plurality of ultrasonic transducers (e.g., 1280, 1281 . . . 1289) may be for dry stimulation. The plurality of ultrasonic transducers (e.g., 1280, 1281 . . . 1289) may be flexible. The plurality of ultrasonic transducers (e.g., 1280, 1281 . . . 1289) may be at least a part of at least one array of transducers. The plurality of ultrasonic transducers (e.g., 1280, 1281 . . . 1289) may produce a Focused Ultrasound (FUS) beam. Each of the plurality of ultrasonic transducers (e.g., 1280, 1281 . . . 1289) may be spherically curved. For example, at least one of the plurality of ultrasonic transducers (e.g., 1280, 1281 . . . 1289) may include a 20 cm diameter and an 8 cm radius of curve. According to some of the various embodiments, relative phases of waveforms produced by at least some of the plurality of ultrasonic transducers (e.g., 2180, 1281 . . . 1289) may be adjusted. By way of example and not limitation, at least one of the plurality of ultrasonic transducers (e.g., 1280, 1281 . . . 1289) may individually and/or collectively produce an acoustic focus of 1-5 mm in diameter and/or 1-18 mm in length. The plurality of ultrasonic transducers may, for example, deliver a PeP of less than 500 mW/cm$^2$ to a target tissue. In an example, the system 1200 may produce a plurality of ultrasonic pulses.

In an example, the system 1200 may include a processing unit 1220 and a tangible non-transitory computer readable medium 1250. The processing unit 1220 may include at least one processor. The computer readable medium 1250 may include instructions that cause the processing unit 1220 to detect a response in at least one brain activity of a user to at least one ultrasonic stimulation, the response based at least in part on at least one signal communicated from at least one of the plurality of electrodes (e.g., 1240, 1241 . . . 1249) at block 1251. The at least one signal may be received by the processing unit 1220. The at least one signal may be amplified, digitized, filtered, combinations thereof, and/or the like. The computer readable medium 1250 may include instructions that cause the processing unit 1220 to select at least one ultrasonic transducer for stimulation from at least one of the plurality of ultrasonic transducers (e.g., 1280, 1281 . . . 1289) based at least in part on the response at block 1252. The computer readable medium 1250 may include instructions that cause the processing unit 1220 to create stimulation instructions at block 1253. The stimulation instructions may be based at least in part on the response and/or the at least one signal. The computer readable medium 1250 may include instructions that cause the processing unit 1220 to communicate the stimulation instructions to the at least one ultrasonic transducer for stimulation at block 1254. The computer readable medium 1250 may include instructions that cause the processing unit 1220 to detect a change in the response in at least one of the at least one brain activity at bock 1255. The computer readable medium 1250 may include instructions that cause the processing unit 1220 to create stimulation instructions based at least in part on the change in the response at 1256.

In an example, the system 1200 may include a transceiving unit 1270. The transceiving unit 1270 may include at least one transceiver. The at least one transceiver may include at least one transmitter and at least one receiver. The transceiving unit 1270 may communicate directly or indirectly with at least one remote device 1275. By way of example and not limitation, the remote device 1275 may be employed by the user, a remote operator, a medical professional, combinations thereof, and/or the like. The system 1200 may accept operational instructions from the remote device 1275. The system 1200 may communicate notifications to the remote device 1275.

In an example, the system 1200 may include a helmet liner, a hat liner, a cap liner, combinations thereof, and/or the like including the at least one wearable material.

In an example, the response in at least one brain activity of a user may be detected through employment of an estimation method. The estimation method may be based at least in part on at least one of the at least one signal. The estimation method may include at least one Orthogonal Matching Pursuit algorithm, at least one Basis Pursuit algorithm, at least one Bayesian statistical model, at least one Bayesian inference algorithm, at least one stochastic search algorithm, at least one hidden Markov model, at least one neural network, at least one kernel method algorithm, at least one particle filter, at least one deep learning algorithm, combinations thereof, and/or the like. The estimation method may be based at least in part on spectral analysis of at least one Fourier transform of at least one of the at least one signal. For example, at least one of the at least one signal may be analyzed in the frequency domain. Frequencies of interest may be associated with brain waveform bandwidths such as those defined by alpha, beta, theta, delta, gamma, mu, combinations thereof, and/or the like. Frequencies of interest may be associated with intermodulation between physiological signals and stimulation signals. In an example, the estimation method may be based at least in part on at least one wavelet transform coefficient of at least one of the at least one signal. The at least one Fourier transform and the at least one wavelet transform coefficient may be based on the same signal.

In an example, the estimation method may include logistic regression. The estimation method may include binary prediction (e.g., Bayesian logistic regression) and/or at least one single index model. The estimation method may include full information for model-fitting. Model fitting may be employed to train prediction algorithms. Prediction algorithms may employ full information as a baseline or control for prediction and/or partial information. The partial information may be unobtrusive. The estimation method may include at least one inference engine. The estimation method may include at least one distribution estimator. The estimation method may include a state model including at least one unobservable process. The estimation method may include at least one filter to remove artifacts.

In an example, the estimation method may be based at least in part on at least one preference of the user. The preference may be based at least in part on characteristics that are physical, physiological, neurological, combinations thereof, and/or the like. The preference may be based at least in part on a history of at least one of the at least one signal. The estimation method may be based at least in part on a result of at least one previous estimation method.

In an example, the estimation method may be based at least in part on data from at least one training phase. The at least one training phase may include production of a plurality of ultrasonic stimulations. The at least one training phase may include monitoring the at least one brain activity. The data may include at least one feedback and/or at least one verification from the user.

In an example, the plurality of ultrasonic transducers may stimulate at least a portion of a vagus nerve of the user transcutaneously, at least a portion of a median nerve of the user transcutaneously, at least a portion of a splanchnic nerve of the user transcutaneously, at least a portion of a splenic nerve of the user transcutaneously, at least a portion of a dorsolateral prefrontal cortex transcranially, at least a portion of an anterior cingulate transcranially, at least a portion of a ventromedial prefrontal cortex transcranially, at least a portion of an amygdala transcranially, combinations thereof, and/or the like.

In an example, the system 1200 may be powered by energy harvested from the at least one brain activity. The system 1200 may include at least one biofuel cell. The at least one biofuel cell may power system 1200. At least a portion of the system 1200 may be a System on a Chip (SoC). The system 1200 may include signal conditioning circuitry. The system 1200 may include integrated power management circuitry.

Figure 10:
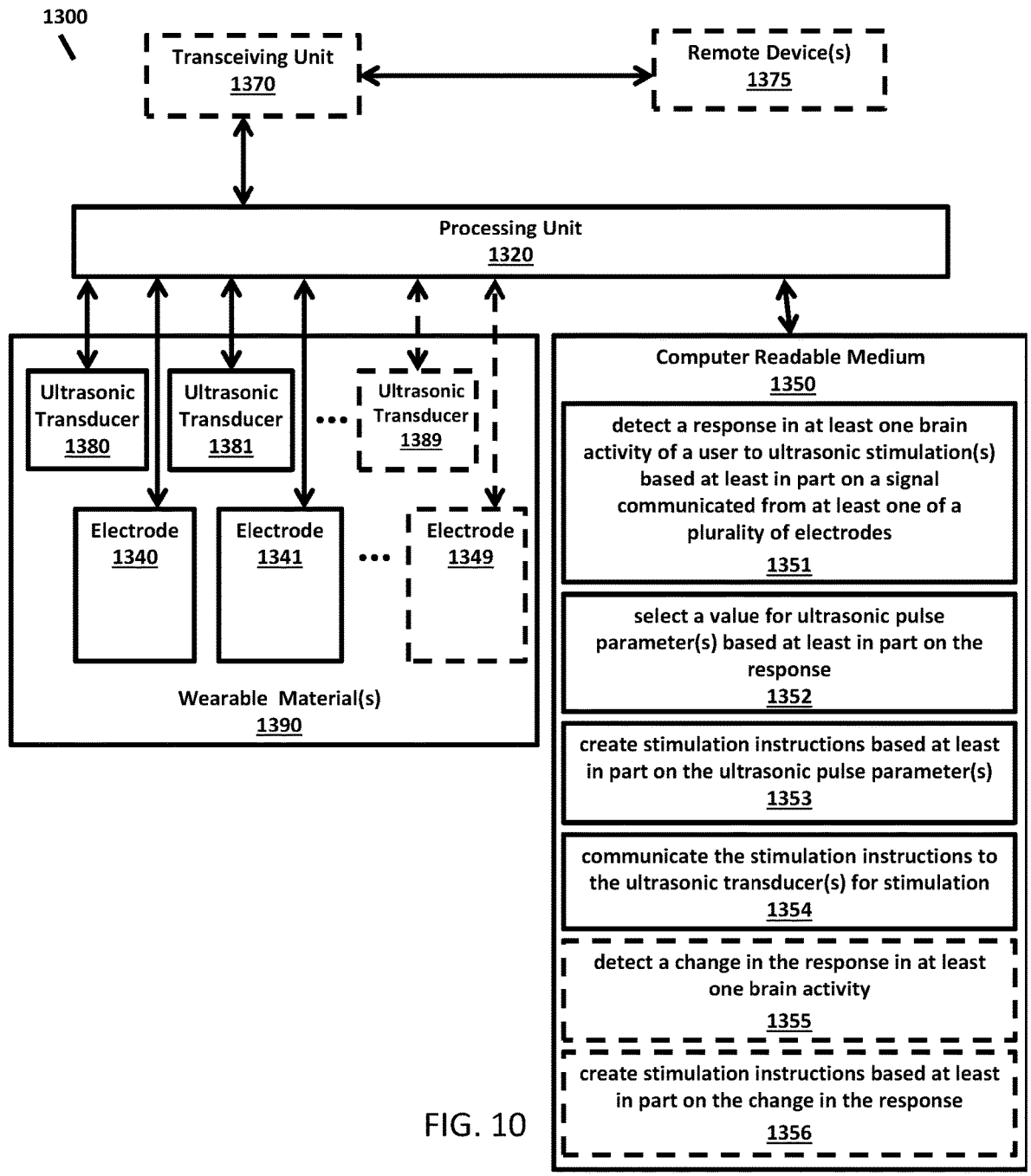
FIG. 10 is an example block diagram showing a system for ultrasonic stimulation according to an example of the present disclosure.

FIG. 10 is an example block diagram showing a system for ultrasonic stimulation according to an example of the present disclosure. The system 1300 may include a plurality of electrodes (e.g., 1340, 1341 . . . 1349). The plurality of electrodes (e.g., 1340, 1341 . . . 1349) may be attached to at least one wearable material 1390. The plurality of electrodes (e.g., 1340, 1341 . . . 1349) may be for dry sensing. The plurality of electrodes (e.g., 1340, 1341 . . . 1349) may be for electroencephalography (EEG) recording. Each of the plurality of electrodes (e.g., 1340, 1341 . . . 1349) may include a pair of electrodes. Alternatively, each of the plurality of electrodes (e.g., 1340, 1341 . . . 1349) may be coupled to at least one common reference electrode. The system 1300 may include a plurality of ultrasonic transducers (e.g., 1380, 1381 . . . 1389). The plurality of ultrasonic transducers (e.g., 1380, 1381 . . . 1389) may be attached to the at least one wearable material 1390. The plurality of ultrasonic transducers (e.g., 1380, 1381 . . . 1389) may be for dry stimulation. The plurality of ultrasonic transducers (e.g., 1380, 1381 . . . 1389) may be flexible. The plurality of ultrasonic transducers may, for example, deliver a PeP of less than 500 mW/cm$^2$ to a target tissue. The plurality of ultrasonic transducers (e.g., 1380, 1381 . . . 1389) may be at least a part of at least one array of transducers.

In an example, the system 1300 may include a processing unit 1320 and a tangible non-transitory computer readable medium 1350. The processing unit 1320 may include at least one processor. The computer readable medium 1350 may include instructions that cause the processing unit 1320 to detect a response in at least one brain activity of a user to at least one ultrasonic stimulation at block 1351. The response may be based at least in part on at least one signal communicated from at least one of the plurality of electrodes (e.g., 1340, 1341 . . . 1349). The at least one signal may be received by the processing unit 1320. The at least one signal may be amplified, digitized, filtered, combinations thereof, and/or the like. The computer readable medium 1350 may include instructions that cause the processing unit 1320 to select a value for at least one of a plurality of ultrasonic pulse parameters based at least in part on the response at block 1352. The computer readable medium 1350 may include instructions that cause the processing unit 1320 to create stimulation instructions based at least in part on the at least one of the plurality of ultrasonic pulse parameters at block 1353. The stimulation instructions may also be based at least in part on the at least one signal. The computer readable medium 1350 may include instructions that cause the processing unit 1320 to communicate the stimulation instructions to at least one of the plurality of ultrasonic transducers (e.g., 1380, 1381 . . . 1389) for stimulation at block 1354. The computer readable medium 1350 may include instructions that cause the processing unit 1320 to detect a change in the response in at least one of the at least one brain activity at block 1355. The computer readable medium 1350 may include instructions that cause the processing unit 1320 to create stimulation instructions based at least in part on the change in the response at block 1356.

In an example, the plurality of ultrasonic pulse parameters may include a target location for stimulation on the body of the user, ultrasonic pulse center frequency, ultrasonic pulse amplitude, ultrasonic pulse intensity, ultrasonic pulse duration, local ultrasonic pulse repetition frequency, global ultrasonic pulse repetition frequency, duty cycle of the ultrasonic pulses, ultrasonic spatial pulse length, a number of ultrasonic pulses in a group, a number of ultrasonic pulse groups each with consistent pulse repetition rates, a number of ultrasonic pulse groups at least two of the ultrasonic pulse groups including distinct pulse repetition rates, ultrasonic pulse ramp up time, ultrasonic pulse damping, relative phase of at least one ultrasonic pulse, relative amplitude of at least one ultrasonic pulse, duration of ultrasonic treatment, frequency of ultrasonic treatment, deactivation pulse center frequency, deactivation pulse amplitude, deactivation pulse intensity, deactivation pulse duration, deactivation pulse repetition frequency, duration of deactivation treatment, combinations thereof, and/or the like.

In an example, the ultrasonic pulse center frequency may, for example, include 2-3.5 MHz for focused ultrasound. The ultrasonic pulse intensity may be determined at a spatial maximum or over a spatial average. The ultrasonic pulse intensity may be calculated as a temporal peak, temporal average, pulse average, and/or the like. For example, the ultrasonic pulse intensity may include up to 500 mW/cm$^2$ for Intensity Spatial Peak Pulse Average (ISPPA). The ultrasonic pulse intensity may, for example, include 190 mW/cm$^2$ for focused ultrasound. The ultrasonic pulse duration may, for example, include 90 ms. An off time may, for example, include 10 ms. The local ultrasonic pulse repetition frequency may, for example, include a frequency in the range of 1 kHz to 5 kHz for focused ultrasound. The global ultrasonic pulse repetition frequency may include selectable or sweepable frequencies. The selectable or sweepable frequencies may be based at least in part on a response in at least one brain activity of a user.

In an example, the duty cycle of the ultrasonic pulses may, for example, be adjustable from 10% to 90%. The number of ultrasonic pulses in a group may, for example, include 2-2000 pulses. The ultrasonic pulse ramp up time may, for example, include 1 ms to 3000 ms. The ultrasonic pulse ramp up time may apply to each pulse or to each group of pulses in a plurality of groups of pulses. The ultrasonic pulse damping may decrease pulse amplitude or intensity over a time period including at least one pulse. The relative phase of at least one ultrasonic pulse may be unique to each of at least some of the ultrasonic transducers. The relative phase of at least one ultrasonic pulse may be employed for beam forming. The relative phase of at least one ultrasonic pulse may be relative to the phase of the pulse produced from at least one other ultrasonic transducer. The duration of ultrasonic treatment may, for example, include a time in the range of 1 second to 10 minutes for groups of pulses. The duration of ultrasonic treatment may include the time required to complete at least one activation period and at least one deactivation period. The duration of ultrasonic treatment may, for example, include at least one activation period of 1 second or longer for focused ultrasound. For example, an ultrasonic treatment may include at least one activation period in the range of 2 to 10 seconds for at least one activated pulse. The ultrasonic treatment may include at least one deactivation period of 1 second or longer. For example, an ultrasonic treatment may include at least one activation period in the range of 2 seconds to 5 minutes. The ultrasonic treatment may, for example, include a plurality of activation periods, each of the plurality of activation periods followed by a deactivation period. The frequency of ultrasonic treatment may, for example, include a time period on the order of seconds, hours, minutes, days, combinations thereof, and/or the like.

In an example, the deactivation pulse center frequency may, for example, include 2-3.5 MHz for focused ultrasound. The deactivation pulse intensity may be determined at spatial maximum or over a spatial average. The deactivation pulse intensity may be calculated as a temporal peak, temporal average, pulse average, and/or the like. For example, the deactivation pulse intensity may include 6.4 W/cm$^2$ ISPPA. The deactivation pulse duration may, for example, include 10 ms. The deactivation pulse repetition frequency may, for example, include a frequency in the range of 10 Hz to 500 Hz for focused ultrasound. The duration of deactivation treatment may, for example, include a duration in the range of 10 ms to 7-8 seconds or longer for focused ultrasound. Employment of pulsed ultrasound (e.g., a pulse modulated with a local ultrasonic pulse repetition frequency of 1 kHz) may provide significantly less intensity than the <190 mW/cm2 currently recommended by the Food and Drug Administration (FDA). The computer readable medium 1350 may include instructions that cause the processing unit 1320 to detect inactivation of at least one neuronal activity. Inactivation of at least one neuronal activity may be detected by alteration in evoked potential stimulation employing at least one of the plurality of ultrasonic transducers (e.g., 1380, 1381 . . . 1389) and at least one of the plurality of electrodes (e.g., 1340, 1341 . . . 1349).

In an example, the value for at least one of a plurality of ultrasonic pulse parameters may be based at least in part on at least one physical attribute of the user. The at least one physical attribute may include gender, age, height, weight, neck girth, wrist girth, chest girth, waist girth, at least one baseline autonomic tone, at least one baseline inflammation level, combinations thereof, and/or the like. The at least one baseline inflammation level may, for example, be based at least in part on a blood sample from a blood draw. Alternatively, the at least one baseline inflammation level may, for example, be based at least in part on at least measurement received from a wearable sensor such as a wristband, a tattoo-based sensor, a skin-applied electrochemical sensor, combinations thereof, and/or the like. At least one inflammation level may be employed to confirm reduction in stress, fear, pain, anxiety, depression, combinations thereof, and/or the like.

In an example, the system 1300 may include a transceiving unit 1370. The transceiving unit 1370 may include at least one transceiver. The at least one transceiver may include at least one transmitter and at least one receiver. The transceiving unit 1370 may communicate with at least one remote device 1375. By way of example and not limitation, the remote device 1375 may be employed by the user, a remote operator, a medical professional, combinations thereof, and/or the like. The system 1300 may accept operational instructions from the remote device 1375. The system 1300 may communicate notifications to the remote device 1375.

In an example, the system 1300 may include a helmet liner, a hat liner, a cap liner, combinations thereof, and/or the like including the at least one wearable material 1390.

In an example, the system 1300 may be powered by energy harvested from the at least one brain activity. The system 1300 may include at least one biofuel cell. The at least one biofuel cell may power system 1300. At least a portion of the system 1300 may be a System on a Chip (SoC). The system 1300 may include signal conditioning circuitry. The system 1300 may include integrated power management circuitry.

Figure 11:
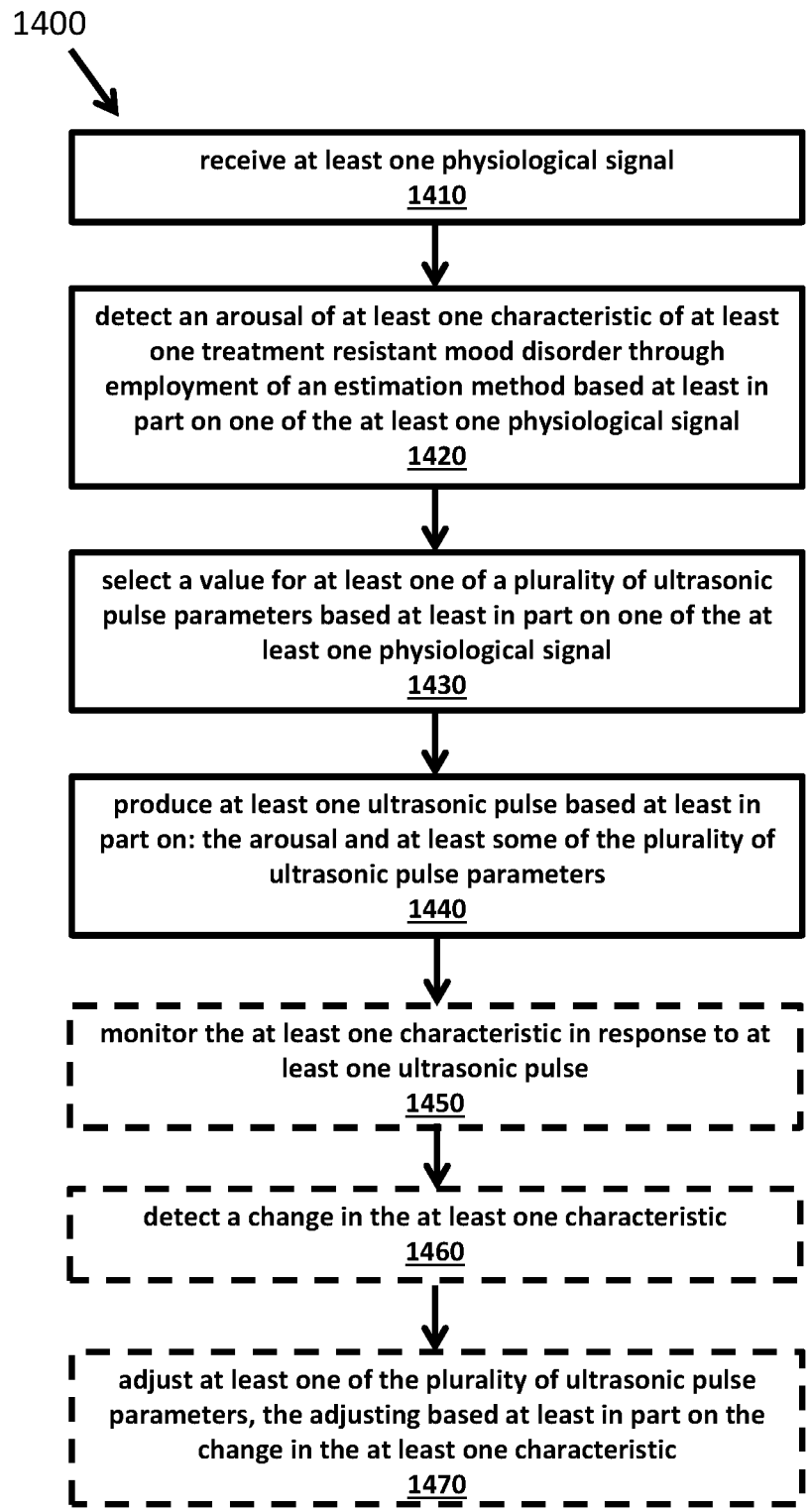
FIG. 11 is an example flow diagram of producing an ultrasonic pulse according to an example of the present disclosure.

FIG. 11 is an example flow diagram 1400 of producing an ultrasonic pulse according to an example of the present disclosure. Although the example flow diagram is described with reference to the flowchart illustrated in FIG. 11, it will be appreciated that many other methods of performing the acts associated with the flow diagram may be used. For example, the order of some of the blocks may be changed, certain blocks may be combined with other blocks, and some of the blocks described are optional.

The flow diagram 1400 of FIG. 11 begins when at least one physiological signal may be received at block 1410. Each of the at least one physiological signal may be transmitted from at least one physiological sensor. The at least one physiological sensor may measure at least one physiological property of a user.

Next, an arousal of at least one characteristic of at least one treatment resistant mood disorder may be detected at block 1420. The arousal may be detected through employment of an estimation method. The estimation method may be based at least in part on at least one of the at least one physiological signal.

Next, a value may be selected for at least one of a plurality of ultrasonic pulse parameters at block 1430. The value may be based at least in part on at least one of the at least one physiological signal.

Next, at least one ultrasonic pulse may be produced at block 1440. The at least one ultrasonic pulse may be based at least in part on the arousal. The at least one ultrasonic pulse may be based at least in part on at least some of the plurality of ultrasonic pulse parameters.

In an example, the at least one characteristic may be monitored in response to at least one ultrasonic pulse at block 1450. By way of example and not limitation, the at least one characteristic may be monitored throughout a day, throughout a night, for any number of days, combinations thereof, and/or the like. In an example, a change in the at least one characteristic may be detected at block 1460. Alternatively, a change in the arousal of the at least one characteristic may be detected. In an example, at least one of the plurality of ultrasonic pulse parameters may be adjusted based at least in part on the change in the at least one characteristic at block 1470. Alternatively, at least one of the plurality of ultrasonic pulse parameters may be adjusted based at least in part on the change in the arousal of the at least one characteristic. The at least one of the plurality of ultrasonic pulse parameters may be adjusted prior to production of at least one additional ultrasonic pulse. At least one ultrasonic pulse may be based at least in part on the change in the at least one characteristic. At least one ultrasonic pulse may be based at least in part on the change in the arousal of the at least one characteristic. In an example, blocks 1450, 1460 and 1470 are optional.

In an example, the at least one physiological signal may include a heart rate signal, an electrocardiogram (ECG) signal, an electroencephalographic (EEG) signal, an evoked potential, combinations thereof, and/or the like. The at least one physiological signal may include at least one data stream including measurements of heart beat, cortical potential, skin conductance response, laser Doppler shift, position, impedance pneumography potential, temperature, combinations thereof, and/or the like. The at least one physiological signal may include a response to at least one previous stimulation. By way of example and not limitation, position may include chest position, chest displacement, chest movement, combinations thereof, and/or the like.

In an example, the at least one physiological sensor may include a heart rate sensor, at least one scalp electrode, at least one skin conductance electrode, at least one photodetector, at least one avalanche photodiode, a respiration rate sensor, at least one thermistor, at least one thermometer, at least one thermocouple, combinations thereof, and/or the like. The heart rate sensor may measure heart rate electrically and/or optically. The heart rate sensor may measure Heart Rate Variability (HRV). Physiological sensors may measure HRV, and may, for example, be coupled to a chest strap and/or a wrist band. A chest strap and/or wrist band may be further coupled to at least one additional physiological sensor to measure, for example, breathing rate, galvanic skin response, skin temperature, combinations thereof, and/or the like. The at least one photodetector may measure laser Doppler shift. Similarly, the at least one avalanche photodiode may measure laser Doppler shift. The at least one respiration rate sensor may include at least one impedance pneumography electrode, at least one capacitive sensor, at least one piezoelectric sensor, at least one servo, an acoustic transducer, an inclinometer, an accelerometer, combinations thereof, and/or the like. Alternatively, respiration rate may be estimated from HRV and/or a photoplethysmography (PPG). The physiological sensor may measure sympathetic tone. The sympathetic tone may be relative to previous measurements. The physiological sensor may measure parasympathetic tone. The parasympathetic tone may be relative to previous measurements. The physiological sensor may be wearable. The physiological sensor may transmit data in more than one time scale. Data transmitted from the physiological sensor may be recorded in a fixed time scale, in more than one time scale, in one adjustable time scale, in a plurality of adjustable time scales, combinations thereof, and/or the like. At least two of a plurality of physiological sensors may transmit data in distinct time scales. Alternatively, at least two of a plurality of physiological sensors may transmit data in the same time scale. The physiological sensor may include a tattoo-based sensor or a skin-applied electrochemical sensor.

In an example, the at least one physiological property may be associated with the autonomic nervous system (ANS). The at least one physiological property may include heart rate, heart rate variability, brain activity, skin conductance, blood flow, respiration rate, core temperature, skin temperature, combinations thereof, and/or the like. Heart rate may, for example, be estimated or determined from an ECG signal and/or a PPG signal. HRV may, for example, be estimated or determined from an ECG signal. HRV may be estimated or determined through employment of at least one RR signal, at least one High Frequency (HF) signal, at least one Low Frequency (LF) signal, at least one LF/HF Ratio, combinations thereof, and/or the like. Brain activity may, for example, be estimated or determined from at least one EEG signal and/or at least one evoked potential. Skin conductance may, for example, be estimated or determined from a galvanic skin response. Blood flow may, for example, be estimated or determined from a laser Doppler velocimetry. Respiration rate may, for example, be estimated or determined from an impedance pneumograph.

In an example, the at least one characteristic may be verified by the user. Detecting an arousal of at least one characteristic of at least one treatment resistant mood disorder may be based at least in part on a first physiological signal and/or a plurality of physiological signals. Detecting an arousal may be verified by a second physiological signal and/or a plurality of additional physiological signals.

In an example, the estimation method may be based at least in part on at least one of the at least one physiological signal. The estimation method may be based at least in part on spectral analysis of at least one Fourier transform of at least one of the at least one physiological signal. For example, at least one of the at least one physiological signal may be analyzed in the frequency domain. According to some of the various embodiments, the estimation method may be based at least in part on at least one wavelet transform coefficient of at least one of the at least one physiological signal. The at least one Fourier transform and the at least one wavelet transform coefficient may be based on the same physiological signal.

In an example, the estimation method may be based at least in part on data from at least one training phase. The at least one training phase may include production of a plurality of ultrasonic pulses. The at least one training phase may include monitoring the at least one characteristic. The data may include at least one feedback and/or at least one verification from the user.

In an example, selecting a value for at least one of a plurality of ultrasonic pulse parameters may be based at least in part on at least one physical attribute of the user. The at least one ultrasonic pulse may stimulate at least a portion of a vagus nerve of the user transcutaneously, at least a portion of a median nerve of the user transcutaneously, at least a portion of a splanchnic nerve of the user transcutaneously, at least a portion of a splenic nerve of the user transcutaneously, at least a portion of a dorsolateral prefrontal cortex transcranially, at least a portion of an anterior cingulate transcranially, at least a portion of a ventromedial prefrontal cortex transcranially, at least a portion of an amygdala transcranially, combinations thereof, and/or the like.

Figure 12:
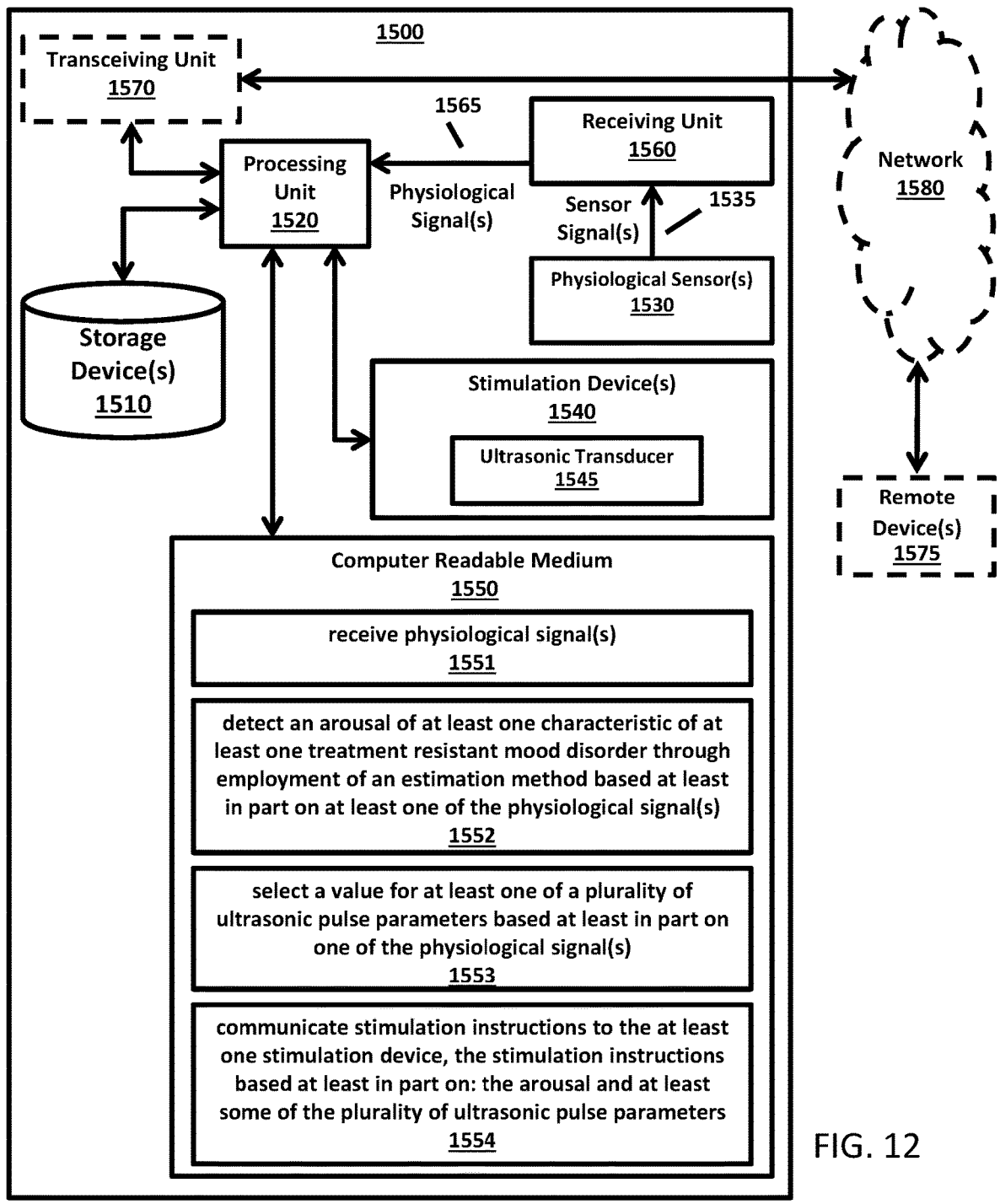
FIG. 12 is an example block diagram showing a system for ultrasonic stimulation according to an example of the present disclosure.

FIG. 12 is an example block diagram showing a system 1500 for ultrasonic stimulation according to an example of the present disclosure. The system 1500 may include at least one storage device 1510. The at least one storage device 1510 may store a plurality of ultrasonic pulse parameters. The system 1500 may include at least one physiological sensor 1530 and a receiving unit 1560. The at least one physiological sensor 1530 may communicate at least one sensor signal 1535 to receiving unit 1560. Receiving unit 1560 may include at least one receiver. Each of the at least one receiver may receive at least one of the at least one sensor signal 1535 communicated from at least one of the at least one physiological sensor 1530. Alternatively, the receiving unit 1560 may include at least one transceiver. The at least one transceiver may communicate with the at least one physiological sensor 1530. The at least one physiological sensor 1530 may measure at least one physiological property of a user.

In an example, the system 1500 may include at least one stimulation device 1540. Each of the at least one stimulation device 1540 may include an ultrasonic transducer 1545. At least one of the at least one stimulation device 1540 may provide transcutaneous nerve stimulation. At least one of the at least one stimulation device 1540 may provide transcranial neurostimulation. The at least one stimulation device 1540 may be for dry stimulation. The at least one stimulation device may stimulate at least a portion of a vagus nerve of the user transcutaneously, at least a portion of a median nerve of the user transcutaneously, at least a portion of a splanchnic nerve of the user transcutaneously, at least a portion of a splenic nerve of the user transcutaneously, at least a portion of a dorsolateral prefrontal cortex transcranially, at least a portion of an anterior cingulate transcranially, at least a portion of a ventromedial prefrontal cortex transcranially, at least a portion of an amygdala transcranially, combinations thereof, and/or the like. The at least one stimulation device 540 may produce a focused ultrasound beam.

In an example, the system 1500 may include a processing unit 1520 and a tangible non-transitory computer readable medium 1550. The processing unit 1520 may include at least one processor. The computer readable medium 1550 may include instructions that cause the processing unit 1520 to receive at least one physiological signal 1565 at block 1551. The at least one physiological signal 1565 may be received from the receiving unit 1560. The computer readable medium 1550 may include instructions that cause the processing unit 1520 to detect an arousal of at least one characteristic of at least one treatment resistant mood disorder at block 1552. The arousal may be detected through employment of an estimation method. The estimation method may be based at least in part on at least one of the at least one physiological signal 1565. The computer readable medium 1550 may include instructions that cause the processing unit 1520 to select a value for at least one of the plurality of ultrasonic pulse parameters at block 1553. The value may be based at least in part on at least one of the at least one physiological signal 1565. The computer readable medium 1550 may include instructions that cause the processing unit 1520 to communicate stimulation instructions to at least one of the at least one stimulation device 1540 at block 1554. The stimulation instructions may be based at least in part on the arousal. The stimulation instructions may be based at least in part on at least some of the plurality of ultrasonic pulse parameters. The stimulation instructions may produce at least one focused ultrasound beam.

In an example, the system 1500 may include a transceiving unit 1570. The transceiving unit 1570 may include at least one transceiver. The at least one transceiver may include at least one transmitter and at least one receiver. At least one of the at least one receiver may be the same as at least one of the at least one receiver associated with the receiving unit 1560. Alternatively, at least one of the at least one transceiver may be the same as at least one of the at least one transceiver associated with the receiving unit 1560. The transceiving unit 1570 may communicate with at least one remote device 1575 employing network 1580. By way of example and not limitation, the at least one remote device 1575 may be employed by the user, a remote operator, a medical professional, combinations thereof, and/or the like. The system 1500 may accept operational instructions from at least one of the at least one remote device 1575. The system 1500 may communicate notifications to at least one of the at least one remote device 1575.

In an example, the at least one storage device 1510 may be communicatively coupled to system 1500 through employment of a wired and/or wireless network. The at least one storage device 1510 may be managed through employment of a cloud service, a web-based electronic data capture system, a web application, a mobile device application, a mobile device operating system, a virtual machine, combinations thereof, and/or the like.

In an example, a sensor signal (e.g., 1535) and a physiological signal (e.g., 1565) may be the same. Alternatively, a physiological signal (e.g., 1565) may be the baseband signal contained within a sensor signal (e.g., 1535). The at least one physiological signal (e.g., 1565) may include a heart rate signal, an electrocardiogram (ECG) signal, an electroencephalographic (EEG) signal, an evoked potential, combinations thereof, and/or the like. The at least one physiological signal (e.g., 1565) may include at least one data stream including measurements of heart beat, cortical potential, skin conductance response, laser Doppler shift, position, impedance pneumography potential, temperature, combinations thereof, and/or the like. By way of example and not limitation, position may include chest position, chest displacement, chest movement, combinations thereof, and/or the like.

In an example, the system 1500 may include at least one biofuel cell. The at least one biofuel cell may power system 1500. At least a portion of the system 1500 may be a System on a Chip (SoC). The system 1500 may include signal conditioning circuitry. The system 1500 may include integrated power management circuitry.

Mood Detection and Notification

Typically, many existing mood detection and notification systems and methods may use physiological signals (e.g., heart rate variability) to trigger notifications. However, generally, most existing mood detection and notification systems and methods may rely on physiological signals crossing a predetermined threshold. Unfortunately, some characteristics of moods may not be anticipated soon enough to enable action prior to a user experiencing the characteristics. Improved mood detection and notification systems and methods are an advantage of the present disclosure.

Examples of the present disclosure may detect mood characteristic(s) and communicate notification(s).

Figure 13:
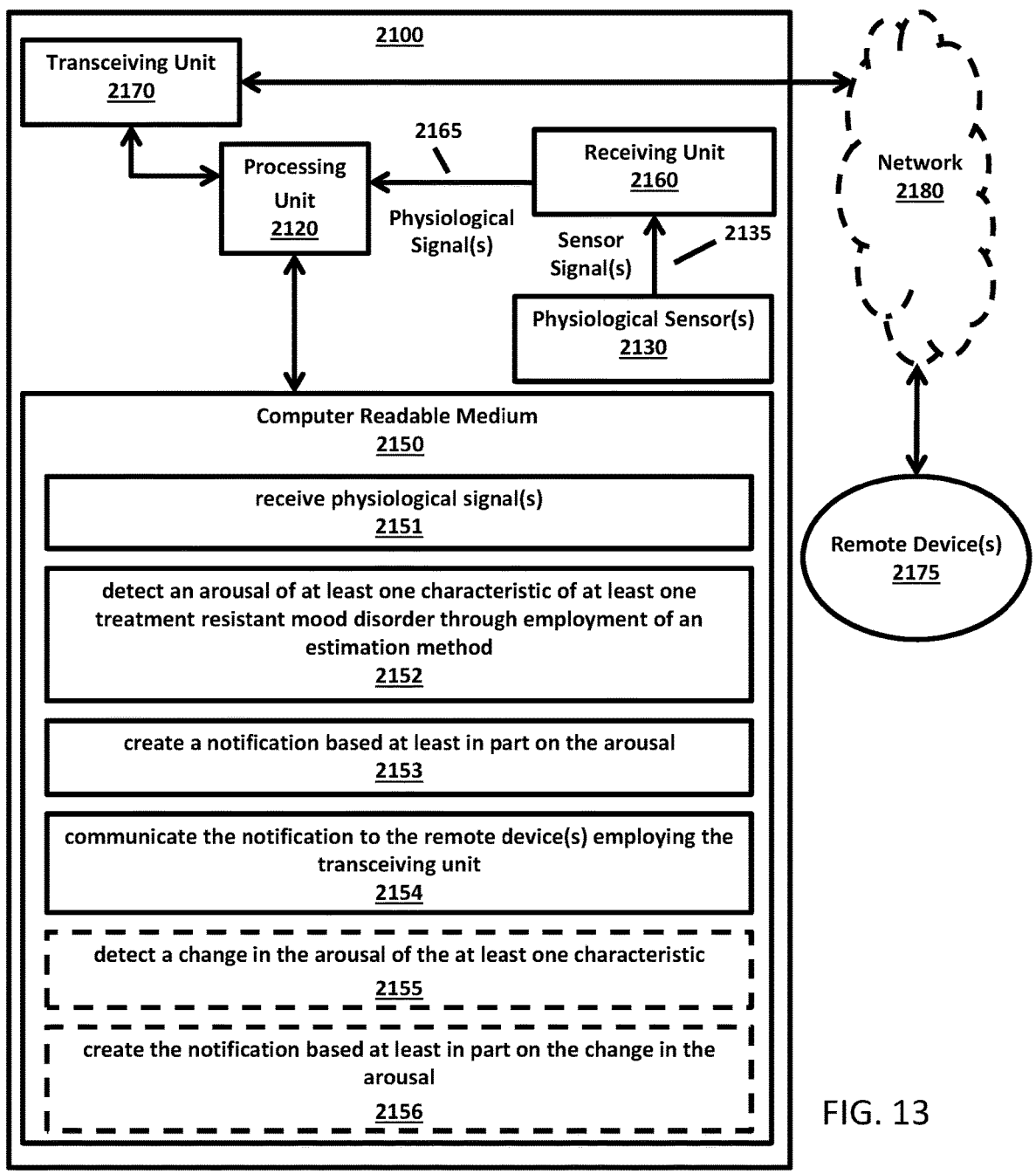
FIG. 13 is an example block diagram showing a system for mood detection and notification according to an example of the present disclosure.

FIG. 13 is an example block diagram showing a system for mood detection and notification according to an example of the present disclosure. The system 2100 may include at least one physiological sensor 2130. The at least one physiological sensor 2130 may measure at least one physiological property of a user. The system 2100 may include receiving unit 2160. The receiving unit 2160 may include at least one receiver. The receiving unit 2160 may receive at least one sensor signal 2135. Each of the at least one sensor signal 2135 may be communicated from one of the at least one physiological sensor 2130. Alternatively, the receiving unit 2160 may include at least one transceiver. The at least one transceiver may communicate with at least one of the at least one physiological sensor 2130.

In an example, the system 2100 may include a transceiving unit 2170. The transceiving unit 2170 may include at least one transceiver. The at least one transceiver may include at least one transmitter and at least one receiver. At least one of the at least one receiver may be the same as at least one of the at least one receiver associated with the receiving unit 2160. Alternatively, at least one of the at least one transceiver may be the same as at least one of the at least one transceiver associated with the receiving unit 2160. The transceiving unit 2170 may communicate directly with at least one remote device 2175, or indirectly with at least one remote device 2175 employing network 2180. By way of example and not limitation, the remote device 2175 may be employed by the user, a remote operator, a medical professional, combinations thereof, and/or the like. The system 2100 may accept operational instructions from the remote device 2175. The system 2100 may communicate at least one notification to the remote device 2175. By way of example and not limitation, the at least one notification may include an alert, a message, streaming data, combinations thereof, and/or the like.

In an example, the system 2100 may include a processing unit 2120 and a tangible non-transitory computer readable medium 2150. The processing unit 2120 may include at least one processor. The computer readable medium 2150 may include instructions that cause the processing unit 2120 to receive at least one physiological signal 2165 at block 2151. The at least one physiological signal 2165 may be received from the receiving unit 2160. The computer readable medium 2150 may include instructions that cause the processing unit 2120 to detect an arousal of at least one characteristic of at least one treatment resistant mood disorder through employment of an estimation method at block 2152. The estimation method may be based at least in part on at least one of the at least one physiological signal 2165. The computer readable medium 2150 may include instructions that cause the processing unit 2120 to create a notification based at least in part on the arousal at block 2153. The computer readable medium 2150 may include instructions that cause the processing unit 2120 to communicate the notification to the at least one remote device 2175 employing the transceiving unit 2170 at block 2154. The computer readable medium 2150 may include instructions that cause the processing unit 2120 to detect a change in the arousal of the at least one characteristic at block 2155. The computer readable medium 2150 may include instructions that cause the processing unit 2120 to create the notification based at least in part on the change in the arousal at block 2156.

In an example, a sensor signal (e.g., 2135) and a physiological signal (e.g., 2165) may be the same. Alternatively, a physiological signal (e.g., 2165) may be the baseband signal contained within a sensor signal (e.g., 2135). The at least one physiological signal (e.g., 2165) may include a heart rate signal, an electrocardiogram (ECG) signal, an electroencephalographic (EEG) signal, combinations thereof, and/or the like. The at least one physiological signal (e.g., 2165) may include at least one data stream including measurements of heart beat, cortical potential, skin conductance response, laser Doppler shift, position, impedance pneumography potential, temperature, combinations thereof, and/or the like. By way of example and not limitation, position may include chest position, chest displacement, chest movement, combinations thereof, and/or the like.

In an example, the at least one physiological sensor (e.g., 2130) may include a heart rate sensor, at least one scalp electrode, at least one skin conductance electrode, at least one photodetector, at least one avalanche photodiode, a respiration rate sensor, at least one thermistor, at least one thermometer, at least one thermocouple, combinations thereof, and/or the like. The heart rate sensor may measure heart rate electrically and/or optically. The heart rate sensor may measure Heart Rate Variability (HRV). Physiological sensors may measure HRV, and may be coupled to a chest strap and/or a wrist band. A chest strap and/or wrist band may be further coupled to at least one additional physiological sensor (e.g., 2130) that measures, for example, breathing rate, galvanic skin response, skin temperature, combinations thereof, and/or the like. The at least one photodetector may measure laser Doppler shift. Similarly, the at least one avalanche photodiode may measure laser Doppler shift. The at least one respiration rate sensor may include at least one impedance pneumography electrode, at least one capacitive sensor, at least one piezoelectric sensor, at least one servo, an acoustic transducer, an inclinometer, an accelerometer, combinations thereof, and/or the like. Alternatively, respiration rate may be estimated from HRV and/or a photoplethysmography (PPG). The physiological sensor (e.g., 2130) may measure sympathetic tone. The sympathetic tone may be relative to previous measurements. The physiological sensor (e.g., 2130) may measure parasympathetic tone. The parasympathetic tone may be relative to previous measurements. The physiological sensor (e.g., 2130) may be wearable. The physiological sensor (e.g., 2130) may communicate data in more than one time scale. Data communicated from the physiological sensor (e.g., 2130) may be recorded in a fixed time scale, in more than one time scale, in one adjustable time scale, in a plurality of adjustable time scales, combinations thereof, and/or the like. The physiological sensor (e.g., 2130) may include a tattoo-based sensor or a skin-applied electrochemical sensor.

In an example, the at least one physiological property may be associated with the autonomic nervous system (ANS). The at least one physiological property may include heart rate, heart rate variability, brain activity, skin conductance, blood flow, respiration rate, core temperature, skin temperature, combinations thereof, and/or the like. Heart rate may, for example, be estimated or determined from an ECG signal and/or a PPG signal. HRV may, for example, be estimated or determined from an ECG signal. HRV may be estimated or determined through employment of at least one RR signal, at least one High Frequency (HF) signal, at least one Low Frequency (LF) signal, at least one LF/HF Ratio, combinations thereof, and/or the like. Brain activity may, for example, be estimated or determined from at least one EEG signal. Skin conductance may, for example, be estimated or determined from a galvanic skin response. Blood flow may, for example, be estimated or determined from a laser Doppler velocimetry. Respiration rate may, for example, be estimated or determined from an impedance pneumograph.

In an example, the at least one characteristic may include stress, fear, pain, anxiety, depression, combinations thereof, and/or the like. An example of stress is a Post-Traumatic Stress Syndrome (PTSD) event experienced by the user. According to some of the various embodiments, the at least one characteristic may be confirmed and/or associated with feedback from the user. A confirmation and/or feedback from by the user may be associated with a distinct feature in at least one of the at least one physiological signal (e.g., 2165). The confirmation and/or feedback may be associated with at least one result from the estimation method.

In an example, the estimation method may include at least one Orthogonal Matching Pursuit algorithm, at least one Basis Pursuit algorithm, at least one Bayesian statistical model, at least one Bayesian inference algorithm, at least one stochastic search algorithm, at least one hidden Markov model, at least one neural network, at least one kernel method algorithm, at least one particle filter, at least one deep learning algorithm, combinations thereof, and/or the like. The estimation method may be based at least in part on spectral analysis of at least one Fourier transform of at least one of the at least one physiological signal (e.g., 2165). For example, HRV may be analyzed in the frequency domain. The frequencies of interest may be divided into three major bands: the very low frequency (VLE) may, for example, include a range of 0.003-0.04 Hz; the low frequency (LF) may, for example, include a range of 0.04-0.15 Hz; and the high frequency (HF) may, for example, include a range of 0.15-0.4 Hz. According to some of the various embodiments, the estimation method may be based at least in part on at least one wavelet transform coefficient of at least one of the at least one physiological signal (e.g., 2165). The at least one Fourier transform and the at least one wavelet transform coefficient may be based on the same physiological signal (e.g., 2165).

In an example, the estimation method may include logistic regression. The estimation method may include binary prediction (e.g., Bayesian logistic regression) and/or at least one single index model. The estimation method may include full information for model-fitting. Model fitting may be employed to train prediction algorithms. Prediction algorithms may employ full information as a baseline or control for prediction and/or partial information. The partial information may be unobtrusive. The estimation method may include at least one inference engine. The estimation method may include at least one distribution estimator. The estimation method may include a state model including at least one unobservable process. The estimation method may include at least one filter that removes artifacts.

In an example, the estimation method may be based at least in part on at least one previous arousal, at least one previous physiological signal, combinations thereof, and/or the like. The estimation method may be based at least in part on a history of arousal, a history of at least one physiological signal, combinations thereof, and/or the like. The estimation method may be based at least in part on at least one preference of the user. The preference may be based at least in part on characteristics that are physical, physiological, neurological, combinations thereof, and/or the like. The preference may be based at least in part on a history of arousal, a history of at least one physiological signal, combinations thereof, and/or the like. The estimation method may be based at least in part on a result of at least one previous estimation method.

In an example, the estimation method may be based at least in part on data from at least one training phase. The at least one training phase may include monitoring the at least one characteristic. The data may include a history of arousal, a history of at least one physiological signal, combinations thereof, and/or the like. The data may include at least one feedback and/or at least one confirmation from the user.

In an example, system 2100 may further include at least one accelerometer. The at least one accelerometer may measure proper acceleration (g-force) on at least one axis. The system 2100 may further include a motion sensor. The system 2100 may further include at least one microphone. The at least one microphone may capture audio of a user and/or a surrounding environment. The system 2100 may further include at least one camera. The at least one camera may capture audio of a user and/or a surrounding environment.

In an example, system 2100 may further include at least one biofuel cell. The at least one biofuel cell may power system 2100. In an example, at least a portion of the system 2100 may be a System on a Chip (SoC). The system 2100 may further include signal conditioning circuitry. The system 2100 may further include integrated power management circuitry. The system 2100 may be wearable.

Figure 14:
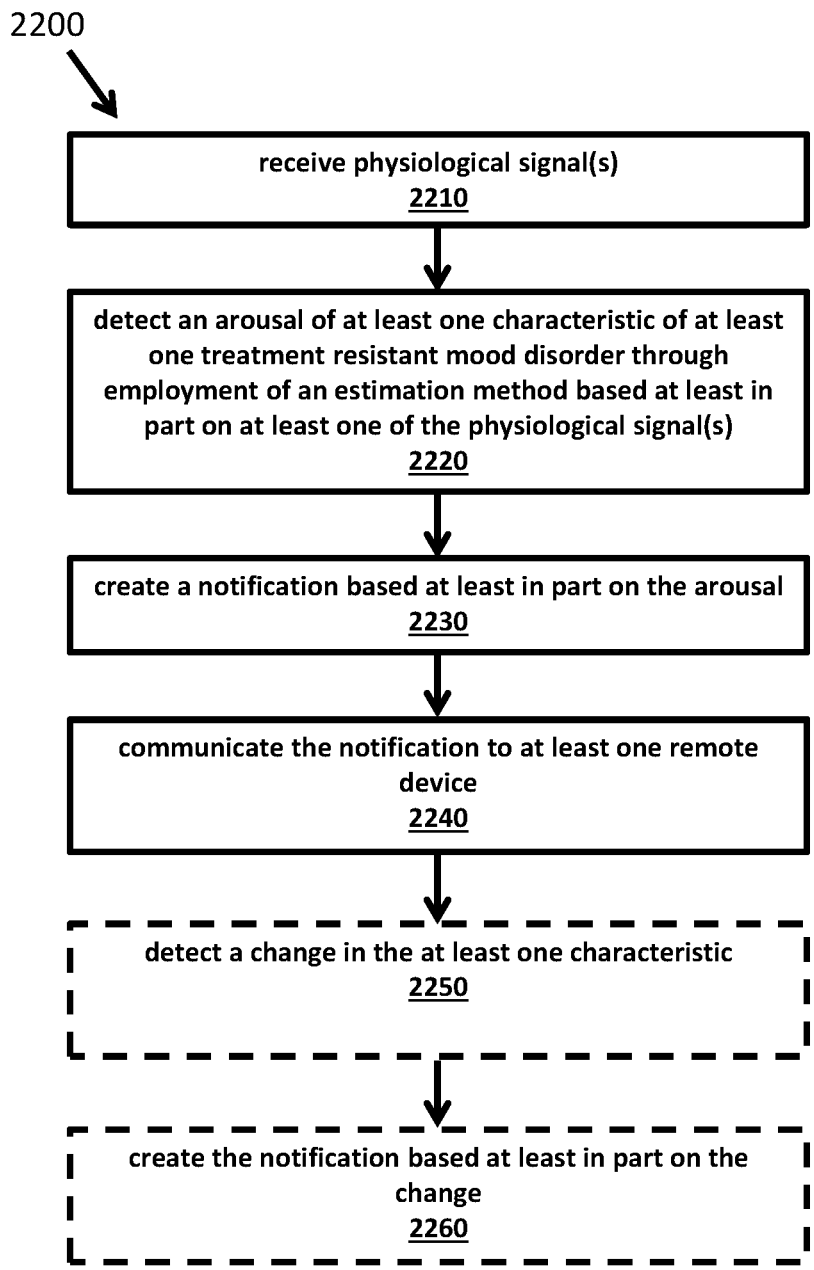
FIG. 14 is an example flow diagram of mood detection and notification according to an example of the present disclosure.

FIG. 14 is an example flow diagram 2200 of mood detection and notification according to an example of the present disclosure. Although the example flow diagram is described with reference to the flowchart illustrated in FIG. 14, it will be appreciated that many other methods of performing the acts associated with the flow diagram may be used. For example, the order of some of the blocks may be changed, certain blocks may be combined with other blocks, and some of the blocks described are optional.

The flow diagram 2200 in FIG. 14 begins when at least one physiological signal may be received at block 2210. An arousal of at least one characteristic of at least one treatment resistant mood disorder may be detected at block 2120. The arousal may be detected through employment of an estimation method. The estimation method may be based at least in part on at least one of the at least one physiological signal. A notification may be created at block 2230. The notification may be based at least in part on the arousal. The notification may be communicated at block 2240. The notification may be communicated to at least one remote device. A change in the arousal of the at least one characteristic may be detected at block 2250. Alternatively, a change in the at least one characteristic may be detected. A notification may be created at block 2260. The notification may be based at least in part on the change.

In an example, the at least one characteristic may be confirmed by the user. Detecting an arousal of at least one characteristic of at least one treatment resistant mood disorder may be based at least in part on a first physiological signal and/or a plurality of physiological signals. Detecting an arousal may be verified by a second physiological signal and/or a plurality of additional physiological signals.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Many of the elements described in the disclosed embodiments may include computer instructions. At least a portion of the computer instructions may be implemented as modules. A module is defined here as an isolatable element that performs a defined function and has a defined interface to other elements. The modules described in this disclosure may be implemented in hardware, a combination of hardware and software, firmware, wetware (i.e. hardware with a biological element) or a combination thereof, all of which are behaviorally equivalent. For example, modules may be implemented using computer hardware in combination with software routine(s) written in a computer language (Java, HTML, XML, PHP, Python, ActionScript, JavaScript, Ruby, Prolog, SQL, VBScript, Visual Basic, Perl, C, C++, Objective-C or the like). Additionally, it may be possible to implement modules using physical hardware that incorporates discrete or programmable analog, digital and/or quantum hardware. Examples of programmable hardware include: computers, microcontrollers, microprocessors, application-specific integrated circuits (ASICs), field programmable gate arrays (FPGAs), and complex programmable logic devices (CPLDs). Computers, microcontrollers and microprocessors are programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, the above mentioned technologies may be used in combination to achieve the result of a functional module.

Some embodiments may employ processing hardware. Processing hardware may include a processing unit, computer equipment, embedded systems, machines and/or the like. The processing hardware may execute instructions. The instructions may be stored on a machine-readable medium. According to some embodiments, the machine-readable medium (e.g., automated data medium) may be a medium that stores data in a machine-readable format that may be accessed by an automated sensing device. Examples of machine-readable media include: magnetic disks, cards, tapes, and drums, flash memory, memory cards, electrically erasable programmable read-only memory (EEPROM), solid state drives, optical disks, barcodes, magnetic ink characters, and/or the like.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments. In particular, it should be noted that, for example purposes various embodiments have been described as communicating with at least one remote device. Persons skilled in the art will recognize that systems communicating with remote devices may vary from a traditional system/device relationship over a network such as the Internet. For example, a system may be collective based: portable equipment, broadcast equipment, virtual, application(s) distributed over a broad combination of computing sources, part of a cloud, combinations thereof, and/or the like. Similarly, for example, a remote device may be a user based client, portable equipment, broadcast equipment, virtual, application(s) distributed over a broad combination of computing sources, part of a cloud, combinations thereof, and/or the like. Additionally, it should be noted that, for example purposes, several of the various embodiments were described as including instructions. However, one skilled in the art will recognize that many various languages and frameworks may be employed to build and use embodiments of the present disclosure.

In addition, it should be understood that any figures that highlight any functionality and/or advantages, are presented for example purposes only. The disclosed architecture is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112. Claims that do not expressly include the phrase "means for" or "step for" are not to be interpreted under 35 U.S.C. 112.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member may be referred to and claimed individually or in any combination with other members of the group or any other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the present disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

EXAMPLES

Various aspects of the subject matter described herein are set out in the following numbered examples.

Example 1

A method comprising: receiving at least one physiological signal, each transmitted from a physiological sensor configured to measure at least one physiological property of a user; detecting an arousal of at least one characteristic of at least one treatment resistant mood disorder through employment of an estimation method based at least in part on at least one of the at least one physiological signal; selecting a value for at least one of a plurality of stimulation parameters based at least in part on at least one of the at least one physiological signal; and producing a first electric field based at least in part on the arousal, the first electric field configured to stimulate at least a portion of a nerve of the user transcutaneously, and based at least in part on at least some of the plurality of stimulation parameters.

Example 2

The method according to Example 1, wherein the nerve is a median nerve.

Example 3

The method according to Example 1, wherein the nerve is a vagus nerve.

Example 4

The method according to Example 1, wherein the at least one physiological signal includes at least one of a heart rate signal, an electrocardiogram signal, and an electroencephalographic signal.

Example 5

The method according to Example 1, wherein the at least one physiological signal includes at least one data stream comprising measurements of at least one of the following: heart beat; cortical potential; skin conductance response; laser Doppler shift; position; impedance pneumography potential; and temperature.

Example 6

The method according to Example 1, wherein the physiological sensor comprises at least one of the following: heart rate sensor; at least one scalp electrode; at least one skin conductance electrode; at least one photodetector; at least one avalanche photodiode; a respiration rate sensor; at least one thermistor; at least one thermometer; and at least one thermocouple.

Example 7

The method according to Example 1, wherein the physiological sensor is configured to measure sympathetic tone.

Example 8

The method according to Example 1, wherein the physiological sensor is configured to measure parasympathetic tone.

Example 9

The method according to Example 1, wherein the physiological sensor is wearable.

Example 10

The method according to Example 1, wherein the at least one physiological property comprises heart rate variability.

Example 11

The method according to Example 1, wherein the at least one physiological property comprises at least one of the following: heart rate; heart rate variability; brain activity; skin conductance; blood flow; respiration rate; core temperature; and skin temperature.

Example 12

The method according to Example 1, wherein the at least one characteristic comprises at least one of the following: stress; fear; pain; anxiety; and depression.

Example 13

The method according to Example 1, wherein the estimation method comprises at least one of the following: Orthogonal Matching Pursuit algorithm; Basis Pursuit algorithm; Bayesian statistical model; Bayesian inference algorithm; stochastic search algorithm; hidden Markov model; neural network; kernel method algorithm; particle filter; and deep learning algorithm.

Example 14

The method according to Example 1, wherein the estimation method is based at least in part on spectral analysis of at least one Fourier transform of at least one of the at least one physiological signal, and at least one wavelet transform coefficient of at least one of the at least one physiological signal.

Example 15

The method according to Example 1, wherein the estimation method is based at least in part on an Orthogonal Matching Pursuit algorithm, and a Basis Pursuit algorithm.

Example 16

The method according to Example 1, wherein the estimation method is based at least in part on a Bayesian inference algorithm.

Example 17

The method according to Example 1, wherein at least one of the plurality of stimulation parameters comprises at least one of the following: target location for stimulation on a body of the user; at least one stimulation pulse frequency; at least one stimulation pulse amplitude; maximum open circuit voltage; at least one stimulation pulse width; maximum allowable skin temperature; at least one stimulation pulse repetition rate for a number of stimulation pulses; at least one duty cycle of stimulation pulses; a number of stimulation pulses in a group; a number of stimulation pulse groups each comprising consistent pulse repetition rates; a number of stimulation pulse groups, at least two of the stimulation pulse groups comprising distinct pulse repetition rates; stimulation pulse group ramp up time; duration of stimulation treatment; and frequency of stimulation treatment.

Example 18

The method according to Example 1, further comprising: detecting a change in the arousal of the at least one characteristic; and producing a second electric field based at least in part on the change in the arousal.

Example 19

The method according to Example 1, further comprising monitoring the at least one characteristic in response to the first electric field.

Example 20

The method according to Example 1, further comprising: monitoring the at least one characteristic in response to the first electric field; detecting a change in the at least one characteristic; and adjusting at least one of the plurality of stimulation parameters, the adjusting based at least in part on the change in the at least one characteristic.

Example 21

The method according to Example 2, further comprising selecting the value for at least one of the plurality of stimulation parameters based at least in part on at least one physical attribute of the user comprising at least one of the following: gender; age; height; weight; wrist girth; at least one baseline autonomic tone; and at least one baseline inflammation level Example 22

The method according to Example 3, further comprising selecting the value for at least one of the plurality of stimulation parameters based at least in part on at least one physical attribute of the user comprising at least one of the following: gender; age; height; weight; neck girth; at least one baseline autonomic tone; and at least one baseline inflammation level.

Example 23

A system comprising: at least one storage device configured to store a plurality of stimulation parameters; at least one physiological sensor, each configured to measure at least one physiological property of a user; a receiving unit configured to receive at least one sensor signal each communicated from one of the at least one physiological sensor; at least one stimulation device, each comprising an electric circuit and configured to provide transcutaneous nerve stimulation; a tangible non-transitory computer readable medium comprising instructions configured to cause a processing unit to: receive at least one physiological signal from the receiving unit; detect an arousal of at least one characteristic of at least one treatment resistant mood disorder through employment of an estimation method based at least in part on at least one of the at least one physiological signal; select a value for at least one of the plurality of stimulation parameters, the value based at least in part on at least one of the at least one physiological signal; and communicate stimulation instructions to at least one of the at least one stimulation device, the stimulation instructions based at least in part on the arousal and at least some of the plurality of stimulation parameters Example 24

The system according to Example 23, wherein the at least one stimulation device is configured to stimulate a median nerve in a wrist of the user Example 25

The system according to Example 23, wherein the at least one stimulation device is configured to stimulate a vagus nerve in a neck of the user.

Example 26

The system according to Example 23, wherein the at least one stimulation device is configured to stimulate a vagus nerve in an ear of the user.

Example 27

The system according to Example 23, further comprising a transceiving unit configured to communicate with at least one remote device.

Example 28

A method comprising: receiving at least one baseline physiological signal, each transmitted from a physiological sensor configured to measure at least one physiological property of a user; producing an electric signal configured to stimulate at least a portion of a nerve of the user transcutaneously, the electric signal based at least in part on at least some of a plurality of stimulation parameters; estimating at least one estimated intermodulation distortion through employment of at least one model for non-linear behavior, the model based at least in part on at least one of the at least one baseline physiological signal, and the electric signal; receiving at least one stimulated physiological signal, each transmitted from the physiological sensor configured to measure the at least one physiological property of the user after receiving transcutaneous nerve stimulation based at least in part on the electric signal; detecting at least one measured intermodulation distortion in at least one of the at least one stimulated physiological signal; calculating a difference between at least one of the at least one estimated intermodulation distortion and at least one of the at least one measured intermodulation distortion; and selecting a value for at least one of the plurality of stimulation parameters based at least in part on the difference.

Example 29

The method according to Example 28, wherein the nerve is a median nerve.

Example 30

The method according to Example 28, wherein the nerve is a vagus nerve.

Example 31

The method according to Example 28, wherein the at least one baseline physiological signal and the at least one stimulated physiological signal each comprises at least one of a heart rate signal, an electrocardiogram signal, and an electroencephalographic signal.

Example 32

The method according to Example 28, wherein the at least one baseline physiological signal and the at least one stimulated physiological signal each comprises at least one data stream comprising measurements of at least one of the following: heart beat; cortical potential; skin conductance response; laser Doppler shift; position; impedance pneumography potential; and temperature.

Example 33

The method according to Example 28, wherein the physiological sensor comprises at least one of the following: a heart rate sensor; at least one scalp electrode; at least one skin conductance electrode; at least one photodetector; at least one avalanche photodiode; a respiration rate sensor; at least one thermistor; at least one thermometer; and at least one thermocouple.

Example 34

The method according to Example 28, wherein the physiological sensor is configured to measure sympathetic tone.

Example 35

The method according to Example 28, wherein the physiological sensor is configured to measure parasympathetic tone.

Example 36

The method according to Example 28, wherein the physiological sensor is wearable.

Example 37

The method according to Example 28, wherein the at least one physiological property comprises at least one of the following: heart rate; heart rate variability; brain activity; skin conductance; blood flow; respiration rate; core temperature; and skin temperature.

Example 38

The method according to Example 28, wherein at least one of the at least one measured intermodulation distortion is associated with at least one of the following characteristics of a treatment resistant mood disorder: stress; fear; pain; anxiety; and depression.

Example 39

The method according to Example 28, wherein the at least one of the plurality of stimulation parameters comprises at least one of the following: target location for stimulation on a body of the user; at least one stimulation pulse frequency; at least one stimulation pulse amplitude; maximum open circuit voltage; at least one stimulation pulse width; maximum allowable skin temperature; at least one stimulation pulse repetition rate for a number of stimulation pulses; at least one duty cycle of stimulation pulses; a number of stimulation pulses in a group; a number of stimulation pulse groups each comprising consistent pulse repetition rates; a number of stimulation pulse groups, at least two of the stimulation pulse groups comprising distinct pulse repetition rates; stimulation pulse group ramp up time; duration of stimulation treatment; and frequency of stimulation treatment.

Example 40

The method according to Example 28, further comprising selecting the value for at least one of the plurality of stimulation parameters based at least in part on at least one physical attribute of the user comprising at least one of the following: gender; age; height; weight; wrist girth; neck girth; at least one baseline autonomic tone; and at least one baseline inflammation level.

Example 41

The method according to Example 28, further comprising filtering at least one of the at least one stimulated physiological signal, the filtering based at least in part on at least one frequency component of the electric signal.

Example 42

A method comprising: producing an electric signal configured to stimulate at least a portion of a nerve of a user transcutaneously, the electric signal based at least in part on at least some of a plurality of stimulation parameters; receiving at least one stimulated physiological signal, each of the at least one stimulated physiological signal transmitted from a physiological sensor configured to measure at least one physiological property of the user; detecting at least one measured intermodulation distortion in at least one of the at least one stimulated physiological signal; and selecting a value for at least one of the plurality of stimulation parameters based at least in part on at least one of the at least one measured intermodulation distortion.

Example 43

The method according to Example 42, wherein the nerve is a median nerve.

Example 44

The method according to Example 42, wherein the nerve is a vagus nerve.

Example 45

The method according to Example 42, further comprising removing at least a portion of the electric signal from the at least one stimulated physiological signal through employment of at least one of a signal processing method, and a signal analysis method.

Example 46

The method according to Example 42, further comprising filtering at least one of the at least one stimulated physiological signal, the filtering based at least in part on at least one frequency component of the electric signal.

Example 47

A system comprising: at least one storage device configured to store a plurality of stimulation parameters; at least one physiological sensor, each configured to measure at least one physiological property of a user; a receiving unit configured to receive at least one stimulated sensor signal each communicated from one of the at least one physiological sensor; at least one stimulation device, each comprising an electric circuit and configured to provide transcutaneous nerve stimulation; a tangible non-transitory computer readable medium comprising instructions configured to cause a processing unit to: communicate stimulation instructions to at least one of the at least one stimulation device, the stimulation instructions based at least in part on at least some of the plurality of stimulation parameters. receive at least one stimulated physiological signal from the receiving unit; detect at least one measured intermodulation distortion in at least one of the at least one stimulated physiological signal; select a value for at least one of the plurality of stimulation parameters based at least in part on at least one of the at least one measured intermodulation distortion.

Example 48

The system according to Example 47, wherein the at least one stimulation device is configured to stimulate a median nerve in a wrist of the user.

Example 49

The system according to Example 47, wherein the at least one stimulation device is configured to stimulate a vagus nerve in a neck of the user.

Example 50

The system according to Example 47, wherein the at least one stimulation device is configured to stimulate a vagus nerve in an ear of the user.

Example 51

The system according to Example 47, further comprising a transceiving unit configured to communicate with at least one remote device.

Example 52

A system comprising: a processing unit; at least two pairs of electrodes attached to at least one wearable material; at least two electric circuits, each coupled to a pair of the at least two pairs of electrodes and configured for transcutaneous nerve stimulation; a receiving unit configured to receive at least one physiological signal each communicated from a physiological sensor configured to measure at least one physiological property of a user; and a tangible non-transitory computer readable medium comprising instructions configured to cause the processing unit to: select one pair of the at least two pairs of electrodes based at least in part on at least one of the at least one physiological signal; create stimulation instructions; and communicate the stimulation instructions to one of the at least two electric circuits coupled to the one pair of the at least two pairs of electrodes.

Example 53

The system according to Example 52, further comprising a wristband comprising the at least one wearable material.

Example 54

The system according to Example 52, further comprising a bracelet comprising the at least one wearable material.

Example 55

The system according to Example 52, further comprising a watch band comprising the at least one wearable material.

Example 56

The system according to Example 52, wherein at least some of the at least two pairs of electrodes are configured to stimulate a median nerve in a wrist of the user.

Example 57

The system according to Example 52, further comprising a scarf comprising the at least one wearable material.

Example 58

The system according to Example 52, further comprising a collar comprising the at least one wearable material.

Example 59

The system according to Example 52, further comprising a tie comprising the at least one wearable material.

Example 60

The system according to Example 52, wherein at least some of the at least two pairs of electrodes are configured to stimulate a vagus nerve in a neck of the user.

Example 61

The system according to Example 52, wherein at least some of the at least two pairs of electrodes are configured to stimulate a vagus nerve in an ear of the user.

Example 62

The system according to Example 52, wherein the at least one physiological signal comprises at least one of a heart rate, an electrocardiogram signal, and an electroencephalographic signal.

Example 63

The system according to Example 52, wherein the at least one physiological signal comprises at least one data stream comprising measurements of at least one of the following: heart beat; cortical potential; skin conductance response; laser Doppler shift; position; impedance pneumography potential; and temperature.

Example 64

The system according to Example 52, wherein the physiological sensor comprises at least one of the following: a heart rate sensor; at least one scalp electrode; at least one skin conductance electrode; at least one photodetector; at least one avalanche photodiode; a respiration rate sensor; at least one thermistor; at least one thermometer; and at least one thermocouple.

Example 65

The system according to Example 52, wherein the physiological sensor is configured to measure sympathetic tone.

Example 66

The system according to Example 52, wherein the physiological sensor is configured to measure parasympathetic tone.

Example 67

The system according to Example 52, wherein the physiological sensor is wearable.

Example 68

The system according to Example 52, wherein the at least one physiological property comprises heart rate variability.

Example 69

The system according to Example 52, wherein the at least one physiological property comprises at least one of the following: heart rate; heart rate variability; brain activity; skin conductance; blood flow; respiration rate; core temperature; and skin temperature.

Example 70

The system according to Example 52, wherein the stimulation instructions are based at least in part on a plurality of stimulation parameters.

Example 71

The system according to Example 52, wherein the instructions are further configured to cause the processing unit to: detect an arousal of at least one characteristic of at least one treatment resistant mood disorder through employment of an estimation method based at least in part on at least one of the at least one physiological signal; and communicate the stimulation instructions based at least in part on the arousal.

Example 72

The system according to Example 52, further comprising a transceiving unit configured to communicate with at least one remote device.

Example 73

The system according to Example 52, further comprising at least one biofuel cell configured to power the system.

Example 74

A system comprising: a processing unit; at least two pairs of electrodes attached to at least one wearable material; at least two electric circuits, each coupled to a pair of the at least two pairs of electrodes and configured for transcutaneous nerve stimulation; at least one ultrasonic transducer attached to the at least one wearable material; a tangible non-transitory computer readable medium comprising instructions configured to cause the processing unit to: estimate a location of at least a portion of at least one vagus nerve fiber of a user employing the at least one ultrasonic transducer; select one pair of the at least two pairs of electrodes based at least in part on the estimate of the location; create stimulation instructions; and communicate the stimulation instructions to one of the at least two electric circuits coupled to the one pair of the at least two pairs of electrodes.

Example 75

The system according to Example 74, further comprising a scarf comprising the at least one wearable material.

Example 76

The system according to Example 74, further comprising a collar comprising the at least one wearable material.

Example 77

The system according to Example 74, further comprising a tie comprising the at least one wearable material.

Example 78

The system according to Example 74, wherein the at least one ultrasonic transducer is flexible.

Example 79

The system according to Example 74, wherein the at least one ultrasonic transducer comprises at least one array of transducers.

Example 80

The system according to Example 74, wherein the stimulation instructions are based at least in part on a plurality of stimulation parameters.

Example 81

The system according to Example 74, wherein the instructions are further configured to cause the processing unit to: estimate a depth of at least the portion of the at least one vagus nerve fiber of the user employing at least one of the at least one ultrasonic transducer; and create additional stimulation instructions based at least in part on the estimate of the depth.

Example 82

The system according to Example 74, further comprising a transceiving unit configured to communicate with at least one remote device.

Example 83

The system according to Example 74, further comprising at least one biofuel cell configured to power the system.

Example 84

A system comprising: a processing unit; at least one pair of electrodes attached to at least one wearable material; at least one electric circuit, each coupled to one of the at least one pair of electrodes and configured for transcutaneous nerve stimulation; at least one ultrasonic transducer attached to the at least one wearable material; a tangible non-transitory computer readable medium comprising instructions configured to cause the processing unit to: estimate a depth of at least a portion of at least one vagus nerve fiber of a user employing the at least one ultrasonic transducer; create stimulation instructions based at least in part on the estimate of the depth; and communicate the stimulation instructions to one of the at least one electric circuit.

Example 85

The system according to Example 84, wherein the stimulation instructions are based at least in part on a plurality of stimulation parameters.

Example 86

A method comprising: estimating a location of at least a portion of at least one vagus nerve fiber of a user employing at least one ultrasonic transducer attached to at least one wearable material; selecting one pair of at least two pairs of electrodes based at least in part on the estimate of the location, the at least two pairs of electrodes attached to the at least one wearable material; and producing an electric field employing the one pair of the at least two pairs of electrodes, the electric field based at least in part on at least some of a plurality of stimulation parameters, and configured to stimulate at least the portion of the at least one vagus nerve fiber of the user transcutaneously.

Example 87

The method according to Example 86, further comprising: estimating a depth of at least the portion of the at least one vagus nerve fiber of the user employing at least one of the at least one ultrasonic transducer; and selecting a value for at least one of the plurality of stimulation parameters based at least in part on the estimate of the depth.

Example 88

A method comprising: estimating a depth of at least a portion of at least one vagus nerve fiber of a user employing at least one ultrasonic transducer attached to at least one wearable material; selecting a value for at least one of a plurality of stimulation parameters based at least in part on the estimate of the depth; and producing an electric field employing one pair of at least one pair of electrodes, the electric field based at least in part on the at least one of the plurality of stimulation parameters, and configured to stimulate at least the portion of the at least one vagus nerve fiber of the user transcutaneously.

Example 89

A system comprising: a processing unit; a plurality of ultrasonic transducers attached to at least one wearable material; a tangible non-transitory computer readable medium comprising instructions configured to cause the processing unit to: estimate a location of at least one nerve fiber of a user employing at least one of the plurality of ultrasonic transducers; select at least one ultrasonic transducer for stimulation from the plurality of ultrasonic transducers based at least in part on the estimate of the location; create stimulation instructions; and communicate the stimulation instructions to the at least one ultrasonic transducer for stimulation.

Example 90

The system according to Example 89, further comprising a scarf comprising the at least one wearable material.

Example 91

The system according to Example 89, further comprising a collar comprising the at least one wearable material.

Example 92

The system according to Example 89, further comprising a tie comprising the at least one wearable material.

Example 93

The system according to Example 89, further comprising a wristband comprising the at least one wearable material.

Example 94

The system according to Example 89, further comprising an article of clothing comprising the at least one wearable material.

Example 95

The system according to Example 89, further comprising a wrap comprising the at least one wearable material.

Example 96

The system according to Example 89, further comprising an adhesive patch comprising the at least one wearable material.

Example 97

The system according to Example 89, wherein the plurality of ultrasonic transducers are flexible.

Example 98

The system according to Example 89, wherein the plurality of ultrasonic transducers are at least a part of at least one array of transducers.

Example 99

The system according to Example 89, wherein the at least one nerve fiber comprises at least one of the following: at least one vagus nerve fiber; at least one median nerve fiber; at least one splanchnic nerve fiber; and at least one splenic nerve fiber.

Example 100

The system according to Example 89, wherein the stimulation instructions are based at least in part on a plurality of stimulation parameters.

Example 101

The system according to Example 89, wherein the instructions are further configured to cause the processing unit to: estimate a depth of the at least one nerve fiber of the user employing at least one of the plurality of ultrasonic transducers; and create additional simulation instructions based at least in part on the estimate of the depth of the at least one nerve fiber.

Example 102

The system according to Example 89, further comprising at least one biofuel cell configured to power the system.

Example 103

The system according to Example 89, further comprising a transceiving unit configured to communicate with at least one remote device.

Example 104

A system comprising: a processing unit; a plurality of electrodes attached to at least one wearable material and configured for electroencephalography recording; a plurality of ultrasonic transducers attached to the at least one wearable material; a tangible non-transitory computer readable medium comprising instructions configured to cause the processing unit to: detect a response in at least one brain activity of a user to at least one ultrasonic stimulation, the response based at least in part on at least one signal communicated from at least one of the plurality of electrodes; select at least one ultrasonic transducer for stimulation from the plurality of ultrasonic transducers based at least in part on the response; create stimulation instructions; and communicate the stimulation instructions to the at least one ultrasonic transducer for stimulation.

Example 105

The system according to Example 104, wherein the plurality of electrodes are configured for dry sensing.

Example 106

The system according to Example 104, further comprising a helmet liner comprising the at least one wearable material.

Example 107

The system according to Example 104, further comprising a hat liner comprising the at least one wearable material.

Example 108

The system according to Example 104, further comprising a cap liner comprising the at least one wearable material.

Example 109

The system according to Example 104, wherein the plurality of ultrasonic transducers are configured for dry stimulation.

Example 110

The system according to Example 104, wherein the response is detected through employment of an estimation method based on at least one of the at least one signal and comprising at least one of the following: Orthogonal Matching Pursuit algorithm; Basis Pursuit algorithm; Bayesian statistical model; Bayesian inference algorithm; stochastic search algorithm; hidden Markov model; neural network; kernel method algorithm; particle filter; and deep learning algorithm.

Example 111

The system according to Example 104, wherein the plurality of ultrasonic transducers are configured to stimulate at least one of the following: at least a portion of a vagus nerve of the user transcutaneously; at least a portion of a median nerve of the user transcutaneously; at least a portion of a splanchnic nerve of the user transcutaneously; at least a portion of a splenic nerve of the user transcutaneously; at least a portion of a dorsolateral prefrontal cortex transcranially; at least a portion of an anterior cingulate transcranially; at least a portion of a ventromedial prefrontal cortex transcranially; and at least a portion of an amygdala transcranially.

Example 112

The system according to Example 104, wherein the instructions are further configured to cause the processing unit to: detect a change in the response in at least one of the at least one brain activity; and create additional stimulation instructions based at least in part on the change in the response.

Example 113

The system according to Example 104, wherein the system is powered by energy harvested from the at least one brain activity.

Example 114

The system according to Example 104, further comprising at least one biofuel cell configured to power the system.

Example 115

A system comprising: a processing unit; a plurality of electrodes attached to at least one wearable material and configured for electroencephalography recording; a plurality of ultrasonic transducers attached to the at least one wearable material; a tangible non-transitory computer readable medium comprising instructions configured to cause the processing unit to: detect a response in at least one brain activity of a user to at least one ultrasonic stimulation, the response based at least in part on at least one signal communicated from at least one of the plurality of electrodes; select a value for at least one of a plurality of ultrasonic pulse parameters based at least in part on the response; create stimulation instructions based at least in part on the at least one of the plurality of ultrasonic pulse parameters; and communicate the stimulation instructions to at least one of the plurality of ultrasonic transducers for stimulation.

Example 116

The system according to Example 115, wherein the at least one of the plurality of ultrasonic pulse parameters comprises at least one of the following: target location for stimulation on a body of the user; ultrasonic pulse center frequency; ultrasonic pulse amplitude; ultrasonic pulse intensity; ultrasonic pulse duration; local ultrasonic pulse repetition frequency; global ultrasonic pulse repetition frequency; duty cycle of ultrasonic pulses; ultrasonic spatial pulse length; a number of ultrasonic pulses in a group; a number of ultrasonic pulse groups each with consistent pulse repetition rates; a number of ultrasonic pulse groups, at least two of the ultrasonic pulse groups comprising distinct pulse repetition rates; ultrasonic pulse ramp up time; ultrasonic pulse damping; relative phase of at least one ultrasonic pulse; relative amplitude of at least one ultrasonic pulse; duration of ultrasonic treatment; frequency of ultrasonic treatment; deactivation pulse center frequency; deactivation pulse amplitude; deactivation pulse intensity; deactivation pulse duration; deactivation pulse repetition frequency; and duration of deactivation treatment.

Example 117

The system according to Example 115, wherein the value is based at least in part on at least one physical attribute of the user comprising one of the following: gender; age; height; weight; neck girth; wrist girth; chest girth; waist girth; at least one baseline autonomic tone; and at least one baseline inflammation level.

Example 118

The system according to Example 115, wherein the plurality of ultrasonic transducers are configured to stimulate at least one of the following: at least a portion of a vagus nerve of the user transcutaneously; at least a portion of a median nerve of the user transcutaneously; at least a portion of a splanchnic nerve of the user transcutaneously; at least a portion of a splenic nerve of the user transcutaneously; at least a portion of a dorsolateral prefrontal cortex transcranially; at least a portion of an anterior cingulate transcranially; at least a portion of a ventromedial prefrontal cortex transcranially; and at least a portion of an amygdala transcranially.

Example 119

A method comprising: receiving at least one physiological signal, each transmitted from a physiological sensor configured to measure at least one physiological property of a user; detecting an arousal of at least one characteristic of at least one treatment resistant mood disorder through employment of an estimation method based at least in part on at least one of the at least one physiological signal; selecting a value for at least one of a plurality of ultrasonic pulse parameters based at least in part on at least one of the at least one physiological signal; and producing at least one ultrasonic pulse based at least in part on the arousal and at least some of the plurality of ultrasonic pulse parameters.

Example 120

The method according to Example 119, wherein the at least one physiological signal comprises at least one of a heart rate signal, an electrocardiogram signal, and an electroencephalographic signal.

Example 121

The method according to Example 119, wherein the at least one physiological signal comprises at least one data stream comprising measurements of at least one of the following: heart beat; cortical potential; skin conductance response; laser Doppler shift; position; impedance pneumography potential; and temperature.

Example 122

The method according to Example 119, wherein the physiological sensor comprises at least one of the following: a heart rate sensor; at least one scalp electrode; at least one skin conductance electrode; at least one photodetector; at least one avalanche photodiode; a respiration rate sensor; at least one thermistor; at least one thermometer; and at least one thermocouple.

Example 123

The method according to Example 119, wherein the physiological sensor is configured to measure sympathetic tone.

Example 124

The method according to Example 119, wherein the physiological sensor is configured to measure parasympathetic tone.

Example 125

The method according to Example 119, wherein the physiological sensor is wearable.

Example 126

The method according to Example 119, wherein the at least one physiological property comprises heart rate variability.

Example 127

The method according to Example 119, wherein the at least one physiological property comprises at least one of the following: heart rate; heart rate variability; brain activity; skin conductance; blood flow; respiration rate; core temperature; and skin temperature.

Example 128

The method according to Example 119, wherein the at least one characteristic comprises at least one of the following: stress; fear; pain; anxiety; and depression.

Example 129

The method according to Example 119, wherein the estimation method comprises at least one of the following: Orthogonal Matching Pursuit algorithm; Basis Pursuit algorithm; Bayesian statistical model; Bayesian inference algorithm; stochastic search algorithm; hidden Markov model; neural network; kernel method algorithm; particle filter; and deep learning algorithm.

Example 130

The method according to Example 119, wherein the estimation method is based at least in part on spectral analysis of at least one Fourier transform of at least one of the at least one physiological signal and at least one wavelet transform coefficient of at least one of the at least one physiological signal.

Example 131

The method according to Example 119, wherein the estimation method is based at least in part on an Orthogonal Matching Pursuit algorithm and a Basis Pursuit algorithm.

Example 132

The method according to Example 119, wherein the estimation method is based at least in part on a Bayesian inference algorithm.

Example 133

The method according to Example 119, wherein the at least one of the plurality of ultrasonic pulse parameters comprises at least one of the following: target location for stimulation on a body of the user; ultrasonic pulse center frequency; ultrasonic pulse amplitude; ultrasonic pulse intensity; ultrasonic pulse duration; local ultrasonic pulse repetition frequency; global ultrasonic pulse repetition frequency; duty cycle of ultrasonic pulses; ultrasonic spatial pulse length; a number of ultrasonic pulses in a group; a number of ultrasonic pulse groups each with consistent pulse repetition rates; a number of ultrasonic pulse groups, at least two of the ultrasonic pulse groups comprising distinct pulse repetition rates; ultrasonic pulse ramp up time; ultrasonic pulse damping; relative phase of at least one ultrasonic pulse; relative amplitude of at least one ultrasonic pulse; duration of ultrasonic treatment; frequency of ultrasonic treatment; deactivation pulse center frequency; deactivation pulse amplitude; deactivation pulse intensity; deactivation pulse duration; deactivation pulse repetition frequency; and duration of deactivation treatment.

Example 134

The method according to Example 119, further comprising: detecting a change in the arousal of the at least one characteristic; and producing an additional at least one ultrasonic pulse based at least in part on the change in the arousal.

Example 135

The method according to Example 119, further comprising monitoring the at least one characteristic in response to the at least one ultrasonic pulse.

Example 136

The method according to Example 119, further comprising: monitoring the at least one characteristic in response to the at least one ultrasonic pulse; detecting a change in the at least one characteristic; and adjusting at least one of the plurality of ultrasonic pulse parameters, the adjusting based at least in part on the change in the at least one characteristic.

Example 137

The method according to Example 119, further comprising selecting the value for at least one of the plurality of ultrasonic pulse parameters based at least in part on at least one physical attribute of the user comprising at least one of the following: gender; age; height; weight; neck girth; wrist girth; chest girth; waist girth; at least one baseline autonomic tone; and at least one baseline inflammation level.

Example 138

The method according to Example 119, wherein the at least one ultrasonic pulse is configured to stimulate at least one of the following at least a portion of a vagus nerve of the user transcutaneously; at least a portion of a median nerve of the user transcutaneously; at least a portion of a splanchnic nerve of the user transcutaneously; at least a portion of a splenic nerve of the user transcutaneously; at least a portion of a dorsolateral prefrontal cortex transcranially; at least a portion of an anterior cingulate transcranially; at least a portion of a ventromedial prefrontal cortex transcranially; and at least a portion of an amygdala transcranially.

Example 139

A system comprising: at least one storage device configured to store a plurality of ultrasonic pulse parameters; at least one physiological sensor, each configured to measure at least one physiological property of a user; a receiving unit configured to receive at least one sensor signal each communicated from the at least one physiological sensor; at least one stimulation device, each comprising an ultrasonic transducer; a tangible non-transitory computer readable medium comprising instructions configured to cause a processing unit to: receive at least one physiological signal from the receiving unit; detect an arousal of at least one characteristic of at least one treatment resistant mood disorder through employment of an estimation method based at least in part on at least one of the at least one physiological signal; select a value for at least one of the plurality of ultrasonic pulse parameters based at least in part on at least one of the at least one physiological signal; and communicate stimulation instructions to the at least one stimulation device, the stimulation instructions based at least in part on the arousal and at least some of the plurality of ultrasonic pulse parameters.

Example 140

The system according to Example 139, wherein the at least one stimulation device is configured for dry stimulation.

Example 141

The system according to Example 139, further comprising a transceiving unit configured to communicate with at least one remote device.

Example 142

The system according to Example 139, wherein the at least one stimulation device is configured to stimulate at least one of the following: at least a portion of a vagus nerve of the user transcutaneously; at least a portion of a median nerve of the user transcutaneously; at least a portion of a splanchnic nerve of the user transcutaneously; at least a portion of a splenic nerve of the user transcutaneously; at least a portion of a dorsolateral prefrontal cortex transcranially; at least a portion of an anterior cingulate transcranially; at least a portion of a ventromedial prefrontal cortex transcranially; and at least a portion of an amygdala transcranially.

Example 143

The system according to Example 139, further comprising at least one biofuel cell configured to power the system.

Example 144

A system comprising: a processing unit; a receiving unit configured to receive at least one sensor signal each communicated from a physiological sensor configured to measure at least one physiological property of a user; a transceiving unit configured to communicate with at least one remote device; and a tangible non-transitory computer readable medium comprising instructions configured to cause the processing unit to: receive at least one physiological signal from the receiving unit; detect an arousal of at least one characteristic of at least one treatment resistant mood disorder through employment of an estimation method based at least in part on at least one of the at least one physiological signal; create a notification based at least in part on the arousal; and communicate the notification to the at least one remote device employing the transceiving unit.

Example 145

The system according to Example 144, wherein the at least one physiological signal comprises at least one of a heart rate signal, an electrocardiogram signal, and an electroencephalographic signal.

Example 146

The system according to Example 144, wherein the at least one physiological signal comprises at least one data stream comprising measurements of at least one of the following: heart beat; cortical potential; skin conductance response; laser Doppler shift; position; impedance pneumography potential; and temperature.

Example 147

The system according to Example 144, wherein the physiological sensor comprises at least one of the following: a heart rate sensor; at least one scalp electrode; at least one skin conductance electrode; at least one photodetector; at least one avalanche photodiode; a respiration rate sensor; at least one thermistor; at least one thermometer; and at least one thermocouple.

Example 148

The system according to Example 144, wherein the physiological sensor is configured to measure sympathetic tone.

Example 149

The system according to Example 144, wherein the physiological sensor is configured to measure parasympathetic tone.

Example 150

The system according to Example 144, wherein the physiological sensor is wearable.

Example 151

The system according to Example 144, wherein the at least one physiological property comprises heart rate variability.

Example 152

The system according to Example 144, wherein the at least one physiological property comprises at least one of the following: heart rate; heart rate variability; brain activity; skin conductance; blood flow; respiration rate; core temperature; and skin temperature.

Example 153

The system according to Example 144, wherein the at least one characteristic comprises at least one of the following: stress; fear; pain; anxiety; and depression.

Example 154

The system according to Example 144, wherein the estimation method comprises at least one of the following: Orthogonal Matching Pursuit algorithm; Basis Pursuit algorithm; Bayesian statistical model; Bayesian inference algorithm; stochastic search algorithm; hidden Markov model; neural network; kernel method algorithm; particle filter; and deep learning algorithm.

Example 155

The system according to Example 144, wherein the estimation method is based at least in part on spectral analysis of at least one Fourier transform of at least one of the at least one physiological signal and at least one wavelet transform coefficient of at least one of the at least one physiological signal.

Example 156

The system according to Example 144, wherein the estimation method is based at least in part on an Orthogonal Matching Pursuit algorithm and a Basis Pursuit algorithm.

Example 157

The system according to Example 144, wherein the estimation method is based at least in part on a Bayesian inference algorithm.

Example 158

The system according to Example 144, wherein the instructions are further configured to cause the processing unit to: detect a change in the arousal of the at least one characteristic; and create an additional notification based at least in part on the change in the arousal.

Example 159

The system according to Example 144, further comprising at least one biofuel cell configured to power the system.

Example 160

A method comprising: receiving at least one physiological signal each communicated from a physiological sensor configured to measure at least one physiological property of a user; detecting an arousal of at least one characteristic of at least one treatment resistant mood disorder through employment of an estimation method based at least in part on at least one of the at least one physiological signal; creating a notification based at least in part on the arousal; communicating the notification to at least one remote device; detecting a change in the at least one characteristic; and creating an additional notification based at least in part on the change.

What is claimed is:

1. A method comprising:
   receiving at least one physiological signal, each transmitted from a physiological sensor configured to measure at least one physiological property of a user;
   producing a first electric field configured to stimulate at least a portion of a median nerve of the user transcutaneously;
   detecting an arousal of at least one characteristic of at least one treatment resistant mood disorder through employment of an estimation method based at least in part on spectral analysis of at least one Fourier transform of at least one of the at least one physiological signal;
   selecting a value for at least one of a plurality of stimulation parameters based at least in part on at least one of the at least one physiological signal; and
   producing a second electric field based at least in part on the arousal, the second electric field configured to stimulate the same portion of the median nerve of the user transcutaneously as the first electric field, and based at least in part on at least some of the plurality of stimulation parameters wherein stimulation begins after detection of an increase in an existing arousal and stimulation stops after detection of a decrease in an existing arousal.

2. The method according to claim 1, wherein the at least one physiological signal includes at least one of a heart rate signal, an electrocardiogram signal, and an electroencephalographic signal.

3. The method according to claim 1, wherein the at least one physiological signal includes at least one data stream comprising measurements of at least one of the following: heart beat; cortical potential; skin conductance response; laser Doppler shift; position; impedance pneumography potential; and temperature.

4. The method according to claim 1, wherein the physiological sensor comprises at least one of the following: a heart rate sensor; at least one scalp electrode; at least one skin conductance electrode; at least one photodetector; at least one avalanche photodiode; a respiration rate sensor; at least one thermistor; at least one thermometer; and at least one thermocouple.

5. The method according to claim 1, wherein the physiological sensor is configured to measure sympathetic tone.

6. The method according to claim 1, wherein the physiological sensor is configured to measure parasympathetic tone.

7. The method according to claim 1, wherein the physiological sensor is wearable.

8. The method according to claim 1, wherein the at least one physiological property comprises at least one of the following: heart rate; heart rate variability; brain activity; skin conductance; blood flow; respiration rate; core temperature; and skin temperature.

9. The method according to claim 1, wherein the at least one characteristic comprises at least one of the following: stress; fear; pain; anxiety; and depression.

10. The method according to claim 1, wherein the estimation method comprises at least one of the following: Orthogonal Matching Pursuit algorithm; Basis Pursuit algorithm; Bayesian statistical model; Bayesian inference algorithm; stochastic search algorithm; hidden Markov model; neural network; kernel method algorithm; particle filter; and deep learning algorithm.

11. The method according to claim 1, wherein at least one of the plurality of stimulation parameters comprises at least one of the following: target location for stimulation on a body of the user; at least one stimulation pulse frequency; at least one stimulation pulse amplitude; maximum open circuit voltage; at least one stimulation pulse width; maximum allowable skin temperature; at least one stimulation pulse repetition rate for a number of stimulation pulses; at least one duty cycle of stimulation pulses; a number of stimulation pulses in a group; a number of stimulation pulse groups each comprising consistent pulse repetition rates; a number of stimulation pulse groups, at least two of the stimulation pulse groups comprising distinct pulse repetition rates; stimulation pulse group ramp up time; duration of stimulation treatment; and frequency of stimulation treatment.

12. The method according to claim 1, further comprising monitoring the at least one characteristic in response to the first electric field.

13. The method according to claim 1, further comprising:
   monitoring the at least one characteristic in response to the first electric field;
   detecting a change in the at least one characteristic; and
   adjusting at least one of the plurality of stimulation parameters, the adjusting based at least in part on the change in the at least one characteristic.

14. The method according to claim 1, further comprising selecting the value for at least one of the plurality of stimulation parameters based at least in part on at least one physical attribute of the user comprising at least one of the following: gender; age; height; weight; wrist girth; at least one baseline autonomic tone; and at least one baseline inflammation level.

15. A system comprising:
   at least one storage device configured to store a plurality of stimulation parameters;

at least one physiological sensor, each configured to measure at least one physiological property of a user;

a receiving unit configured to receive at least one sensor signal each communicated from one of the at least one physiological sensor;

at least one stimulation device, each comprising an electric circuit and configured to provide transcutaneous nerve stimulation wherein a first electric field and a second electric field are produced and configured to stimulate a same portion of a median nerve;

a tangible non-transitory computer readable medium comprising instructions configured to cause a processing unit to:

receive at least one physiological signal from the receiving unit;

detect an arousal of at least one characteristic of at least one treatment resistant mood disorder through employment of an estimation method based at least in part on spectral analysis of at least one Fourier transform of at least one of the at least one physiological signal;

select a value for at least one of the plurality of stimulation parameters, the value based at least in part on at least one of the at least one physiological signal; and communicate stimulation instructions to at least one of the at least one stimulation device, the stimulation instructions based at least in part on the arousal and at least some of the plurality of stimulation parameters wherein stimulation begins after detection of an increase in an existing arousal and stimulation stops after detection of a decrease in an existing arousal.

16. The system according to claim 15, further comprising a transceiving unit configured to communicate with at least one remote device.

17. A method comprising:

receiving at least one physiological signal, each transmitted from a physiological sensor configured to measure at least one physiological property of a user;

producing a first ultrasonic pulse configured to stimulate at least a portion of a median nerve of the user transcutaneously;

detecting an arousal of at least one characteristic of at least one treatment resistant mood disorder through employment of an estimation method based at least in part on spectral analysis of at least one Fourier transform of the at least one physiological signal;

selecting a value for at least one of a plurality of ultrasonic pulse parameters based at least in part on at least one of the at least one physiological signal; and producing a second ultrasonic pulse based at least in part on the arousal and at least some of the plurality of ultrasonic pulse parameters;

wherein the second ultrasonic pulse is configured to stimulate the same portion of the median nerve of the user transcutaneously as the first electric field; and wherein stimulation begins after detection of an increase in an existing arousal and stimulation stops after detection of a decrease in an existing arousal.

* * * * *